(12) United States Patent
Tillekeratne et al.

(10) Patent No.: US 9,469,656 B2
(45) Date of Patent: Oct. 18, 2016

(54) HDAC INHIBITORS AS ANTI-CANCER AGENTS

(71) Applicant: The University of Toledo, Toledo, OH (US)

(72) Inventors: L. M. Viranga Tillekeratne, Toledo, OH (US); Jehad Almaliti, Toledo, OH (US); Ayad Al-Hamashi, Toledo, OH (US); Pravin Bhansali, Toledo, OH (US)

(73) Assignee: The University of Toledo, Toldeo, OH (US)

( * ) Notice: Subject to any disclaimer, the term of this patent is extended or adjusted under 35 U.S.C. 154(b) by 72 days.

(21) Appl. No.: 14/712,341

(22) Filed: May 14, 2015

(65) Prior Publication Data

US 2015/0329560 A1 Nov. 19, 2015

Related U.S. Application Data

(60) Provisional application No. 61/993,608, filed on May 15, 2014.

(51) Int. Cl.
| | | |
|---|---|---|
| A01N 43/42 | (2006.01) |
| A61K 31/44 | (2006.01) |
| C07D 498/18 | (2006.01) |
| C07D 498/08 | (2006.01) |
| A61K 31/425 | (2006.01) |

(52) U.S. Cl.
CPC ........... *C07D 498/18* (2013.01); *A61K 31/425* (2013.01); *C07D 498/08* (2013.01)

(58) Field of Classification Search
CPC ......................... C07D 498/18; A61K 31/425
See application file for complete search history.

(56) References Cited

U.S. PATENT DOCUMENTS 8,217,076 B2 * 7/2012 Williams ............. C07D 498/18
514/539

* cited by examiner

*Primary Examiner* — Wu-Cheng Winston Shen
*Assistant Examiner* — Jean Cornet
(74) *Attorney, Agent, or Firm* — MacMillan, Sobanski & Todd, LLC

(57) ABSTRACT

Largazole analogs, methods of making the same, and methods of using the same, are described.

19 Claims, 45 Drawing Sheets
(29 of 45 Drawing Sheet(s) Filed in Color)

| | MDA-MB-231 (Cancer cell line) | NMuMG (Normal cell line) | U2OS (Cancer cell line) | NIH3T3 (Normal cell line) |
|---|---|---|---|---|
| Largazole | 7.7 nM | 122 nM | 55 nM | 480 nM |
| Paclitaxel | 7.0 nM | 5.9 nM | 12 nM | 6.4 nM |
| Actinomycin D | 0.5 nM | 0.3 nM | 0.8 nM | 0.4 nM |
| Doxorubicin | 310 nM | 63 nM | 220 nM | 47 nM |

FIG. 1B

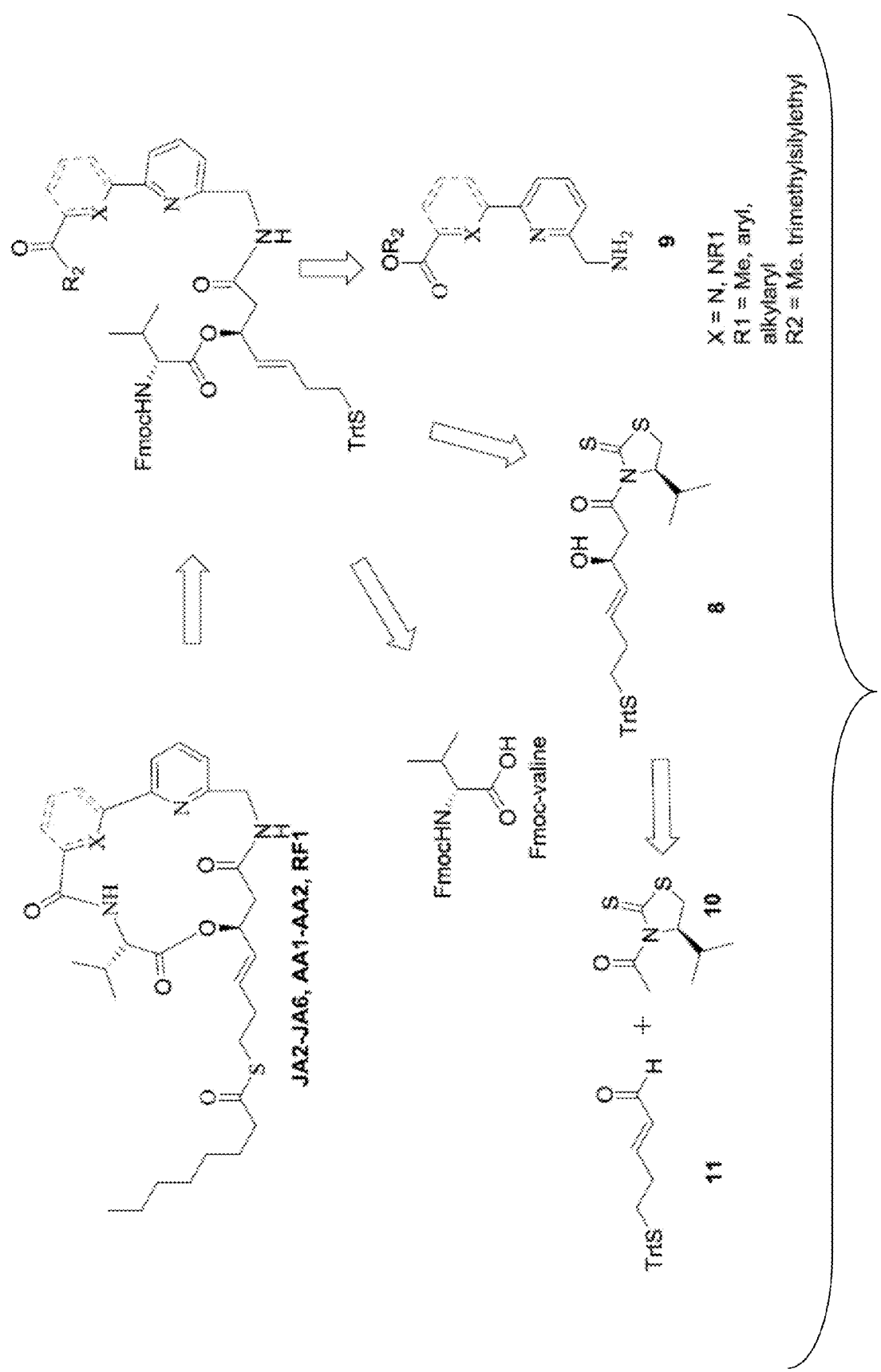
FIG. 5 – Scheme 1

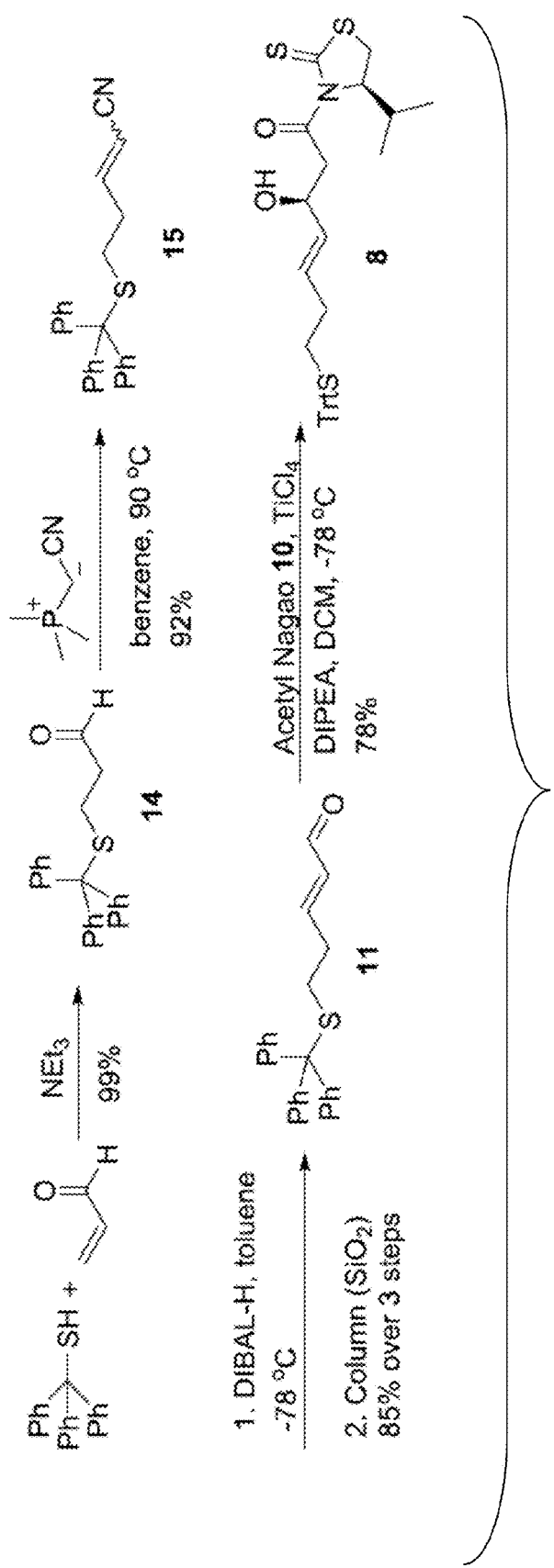
FIG. 6 – Scheme 2

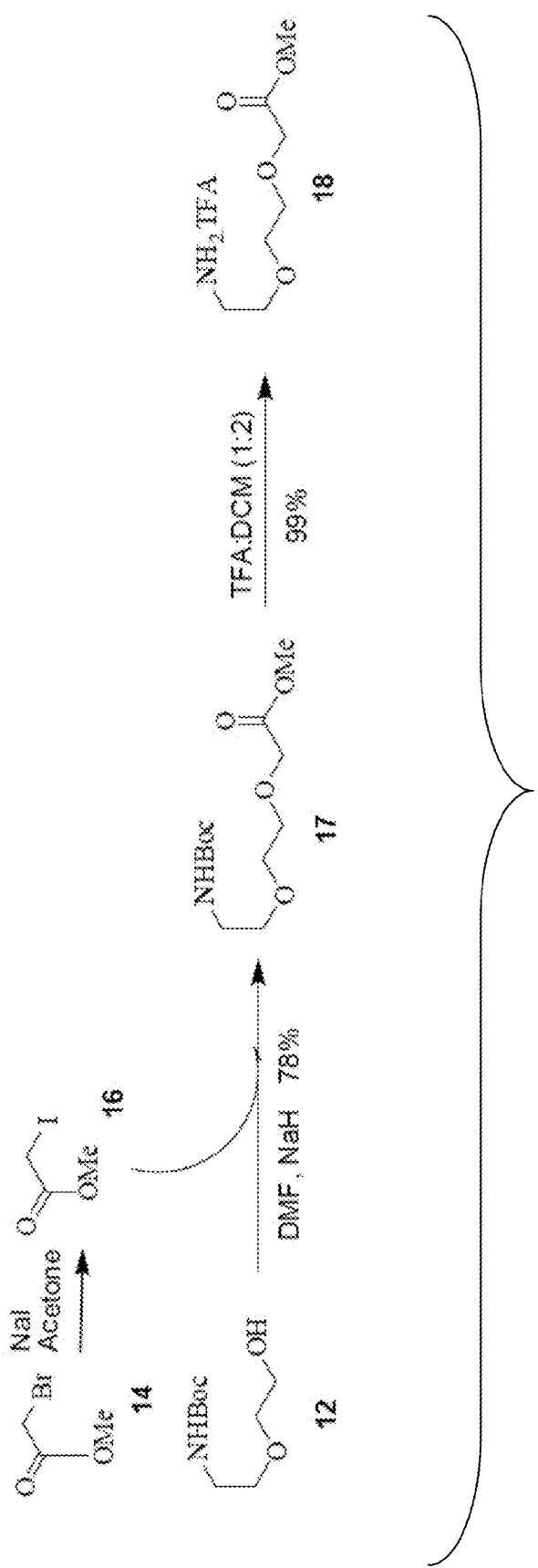
FIG. 7 – Scheme 3

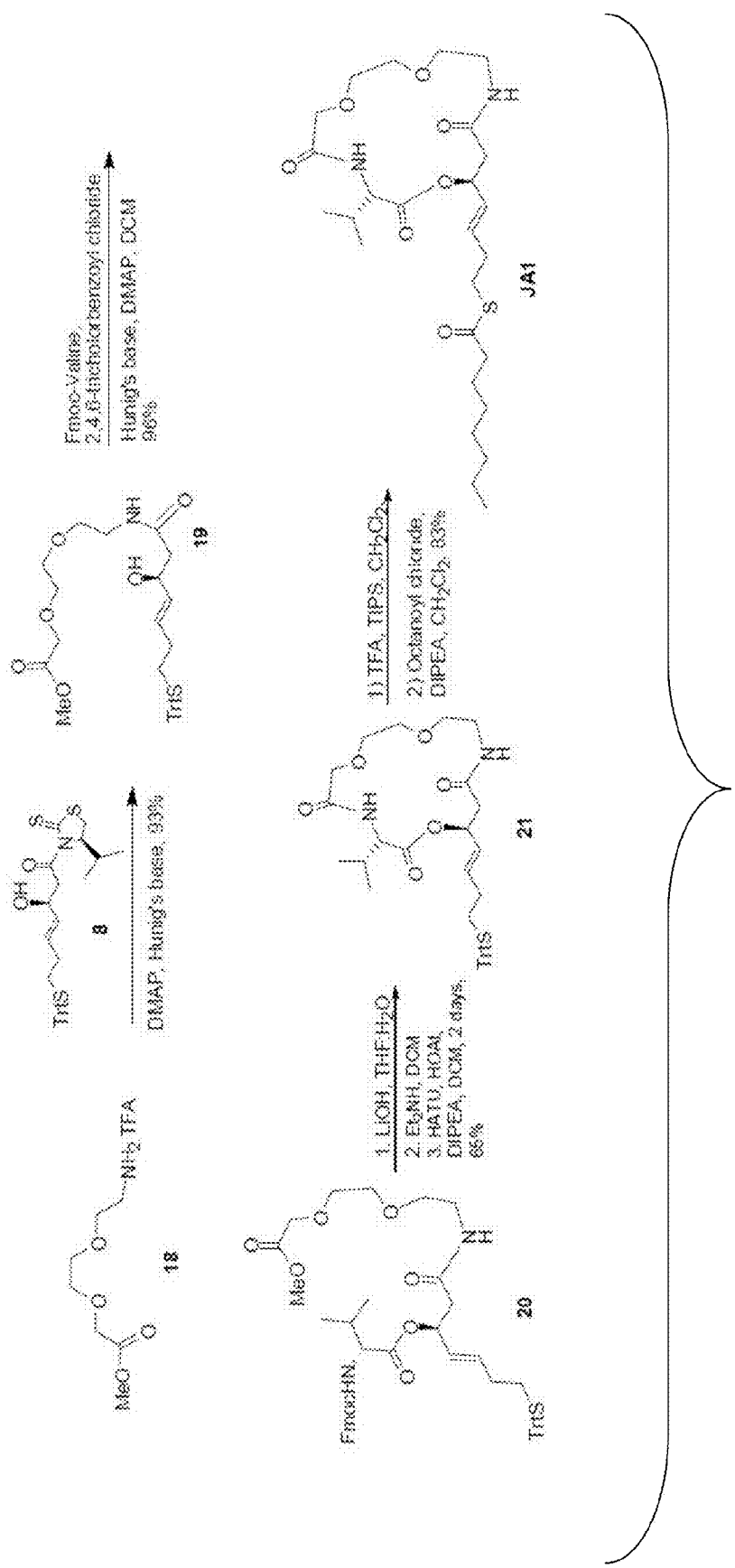
FIG. 8 – Scheme 4

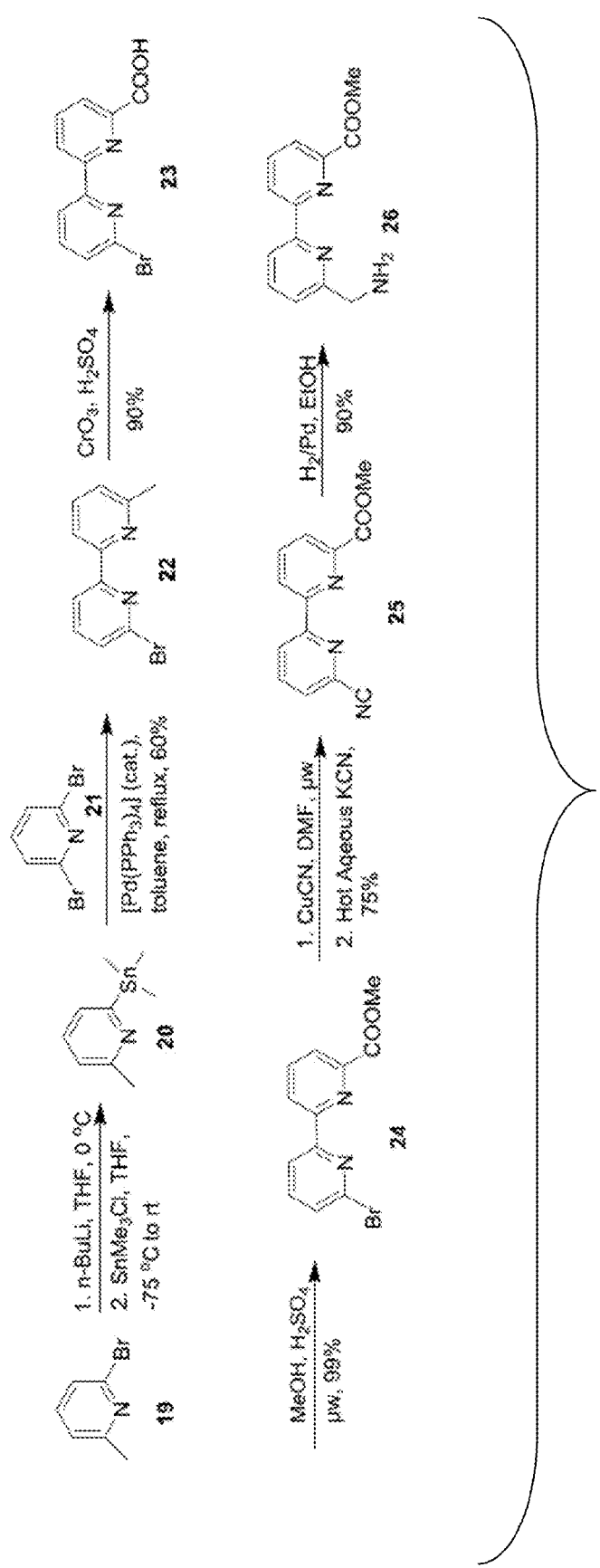
FIG. 9 – Scheme 5

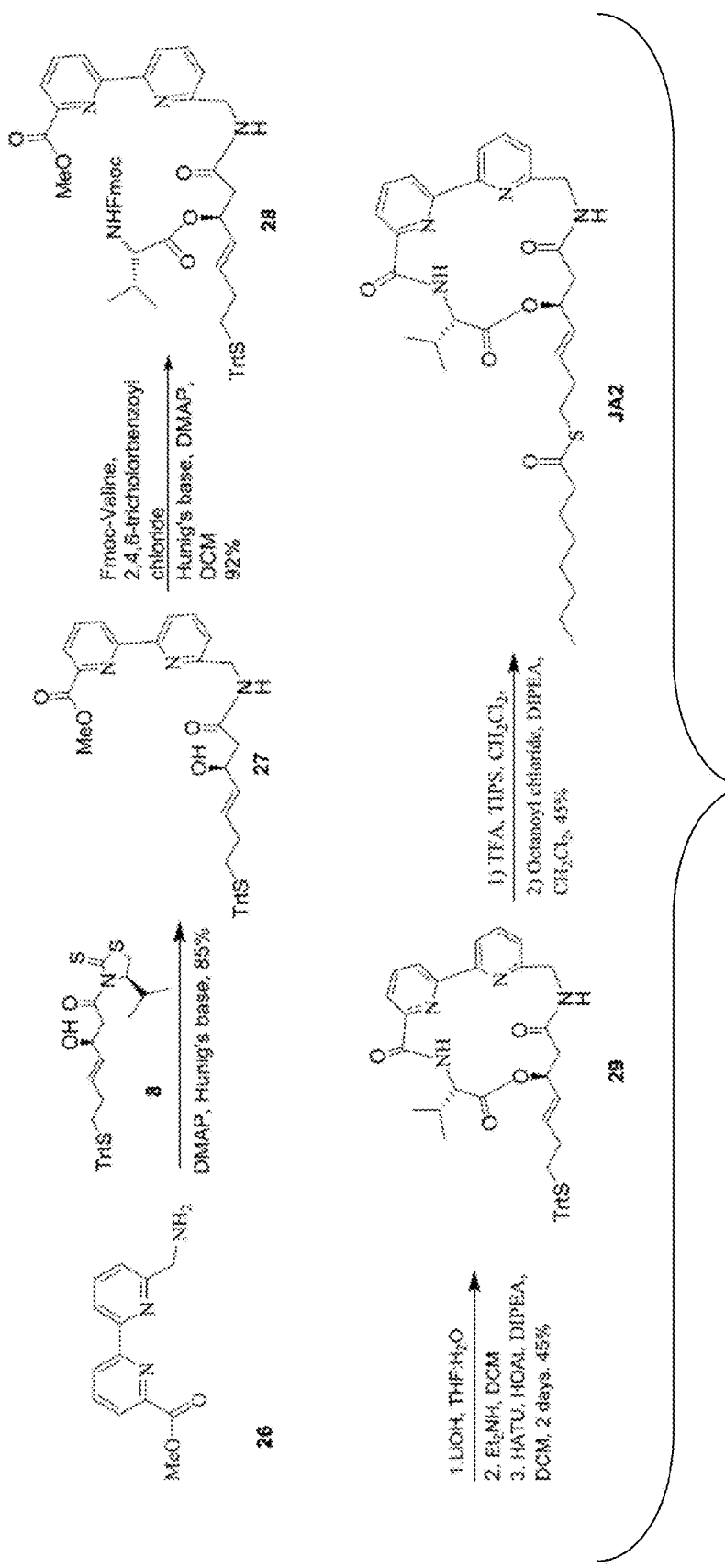
FIG. 10- Scheme 6

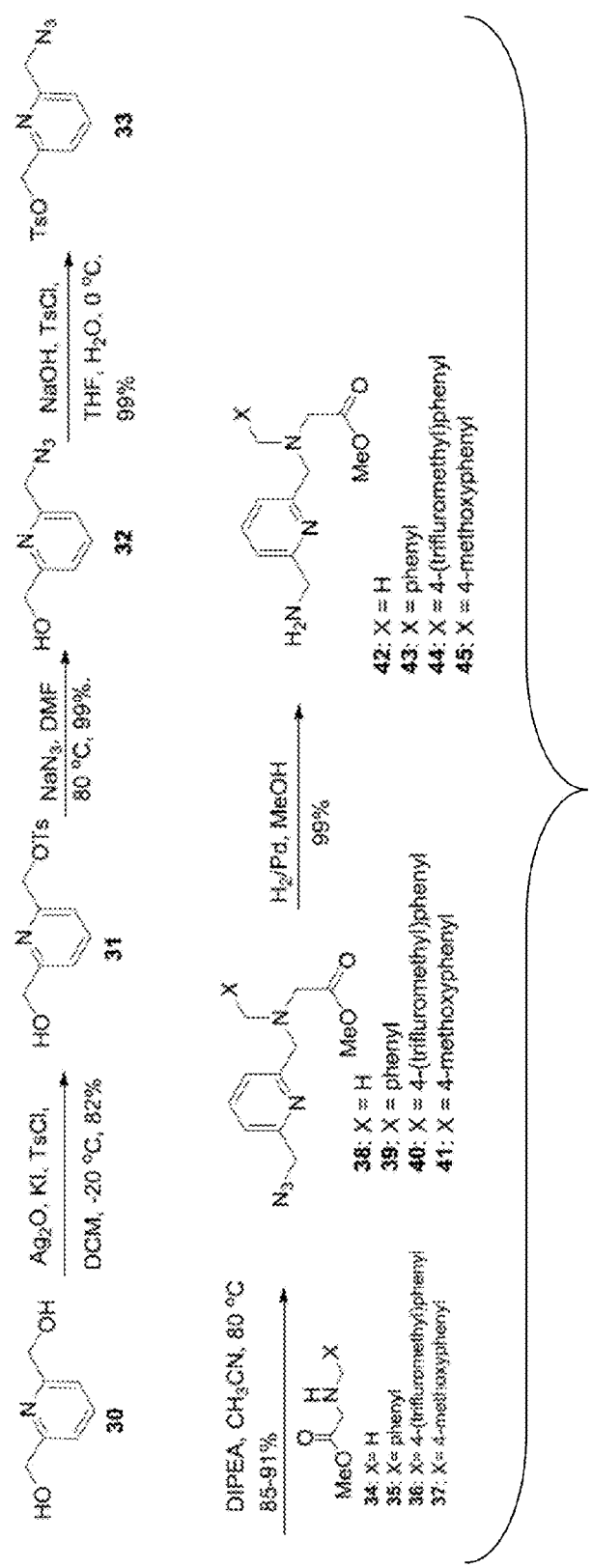
FIG. 11 – Scheme 7

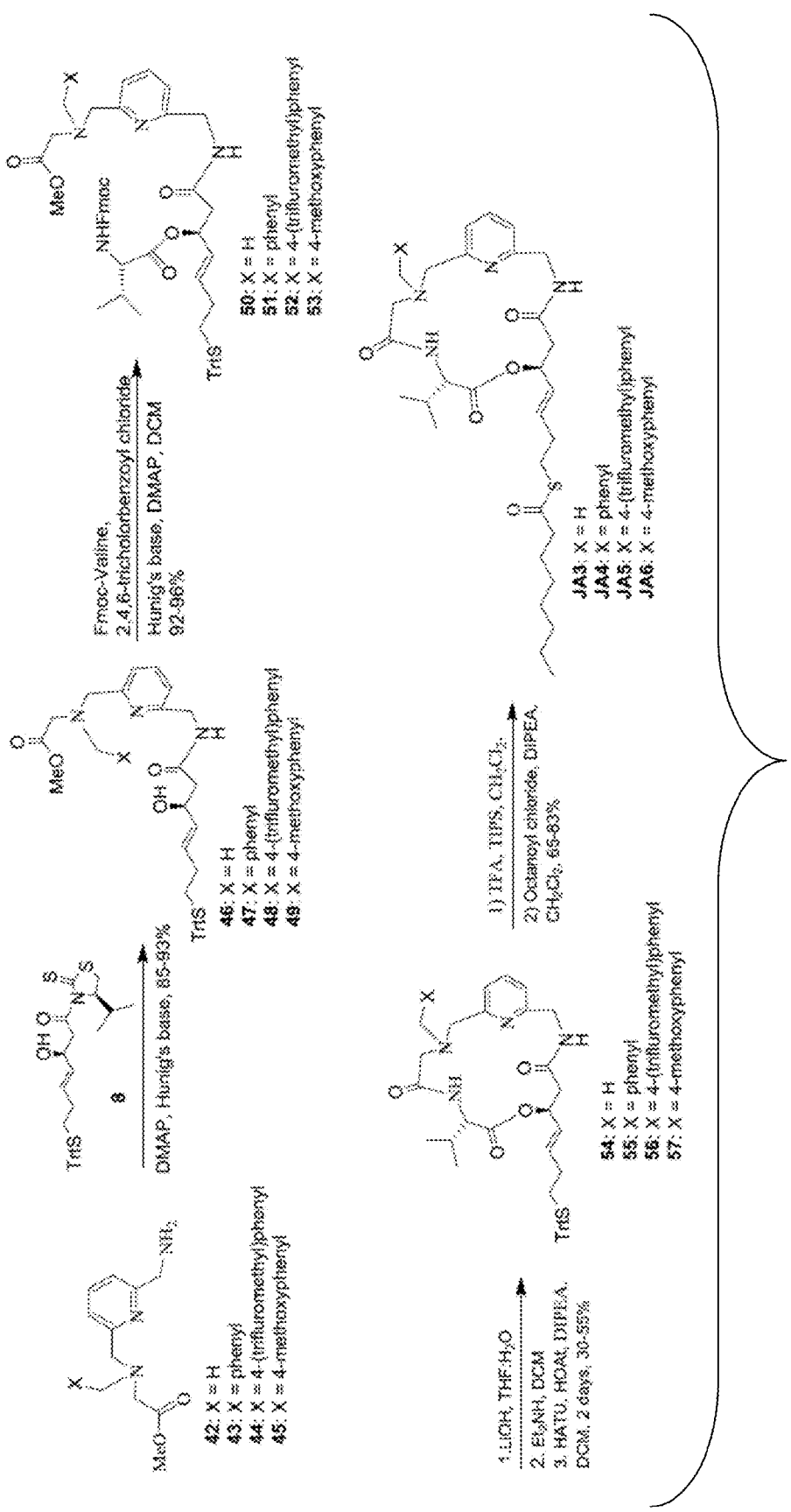
FIG. 12 – Scheme 8

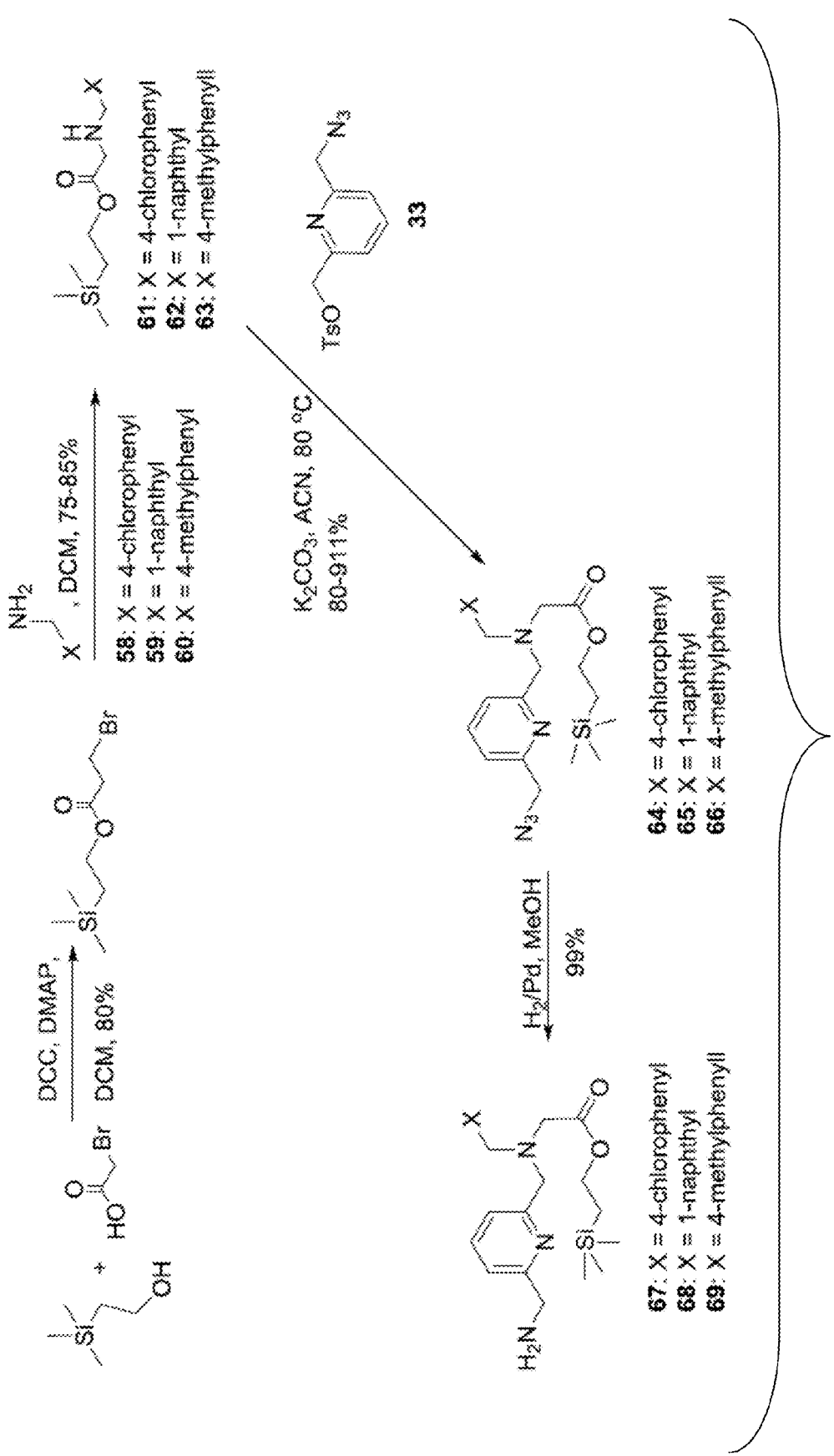
FIG. 13 – Scheme 9

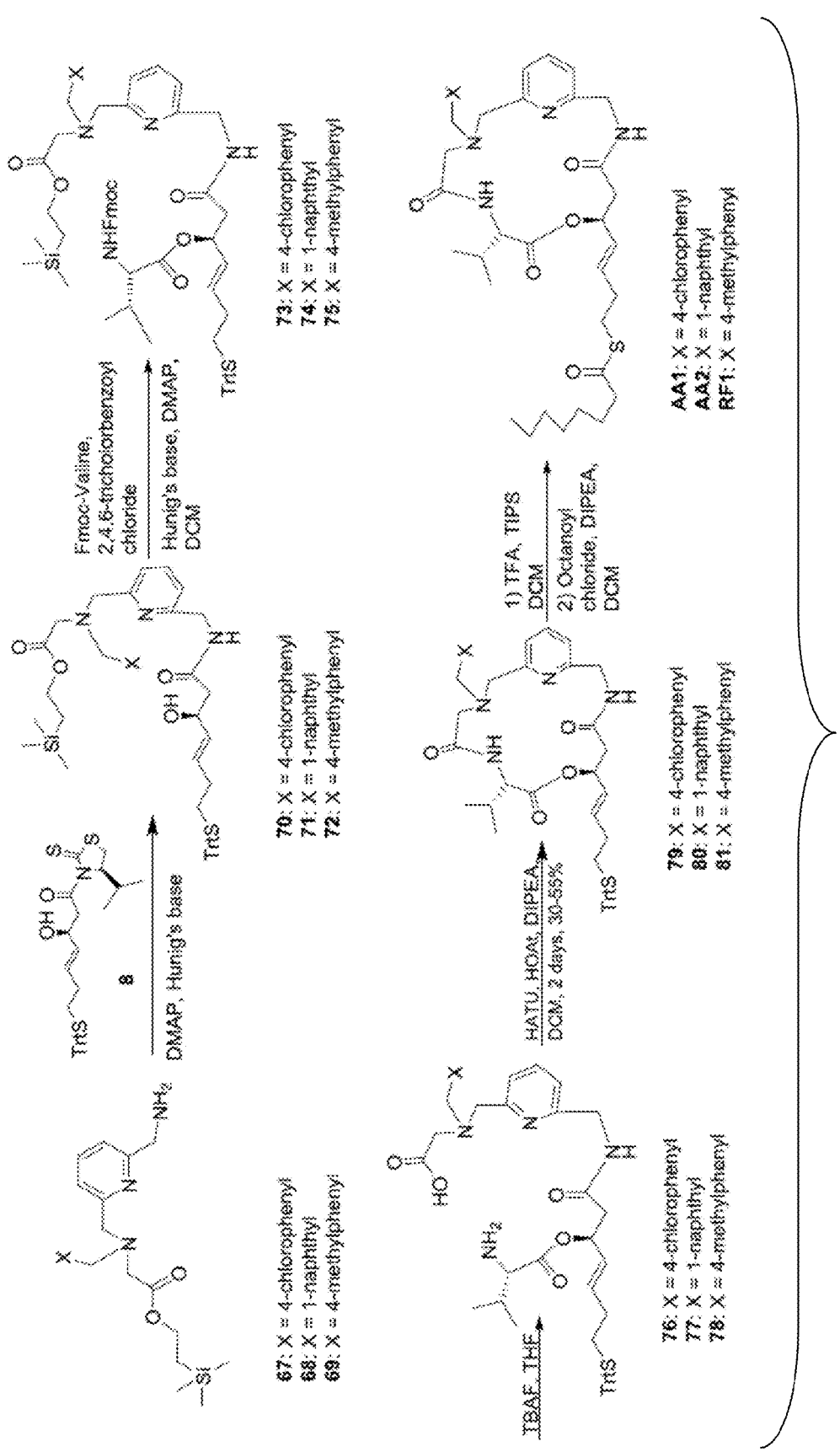
FIG. 14 – Scheme 10

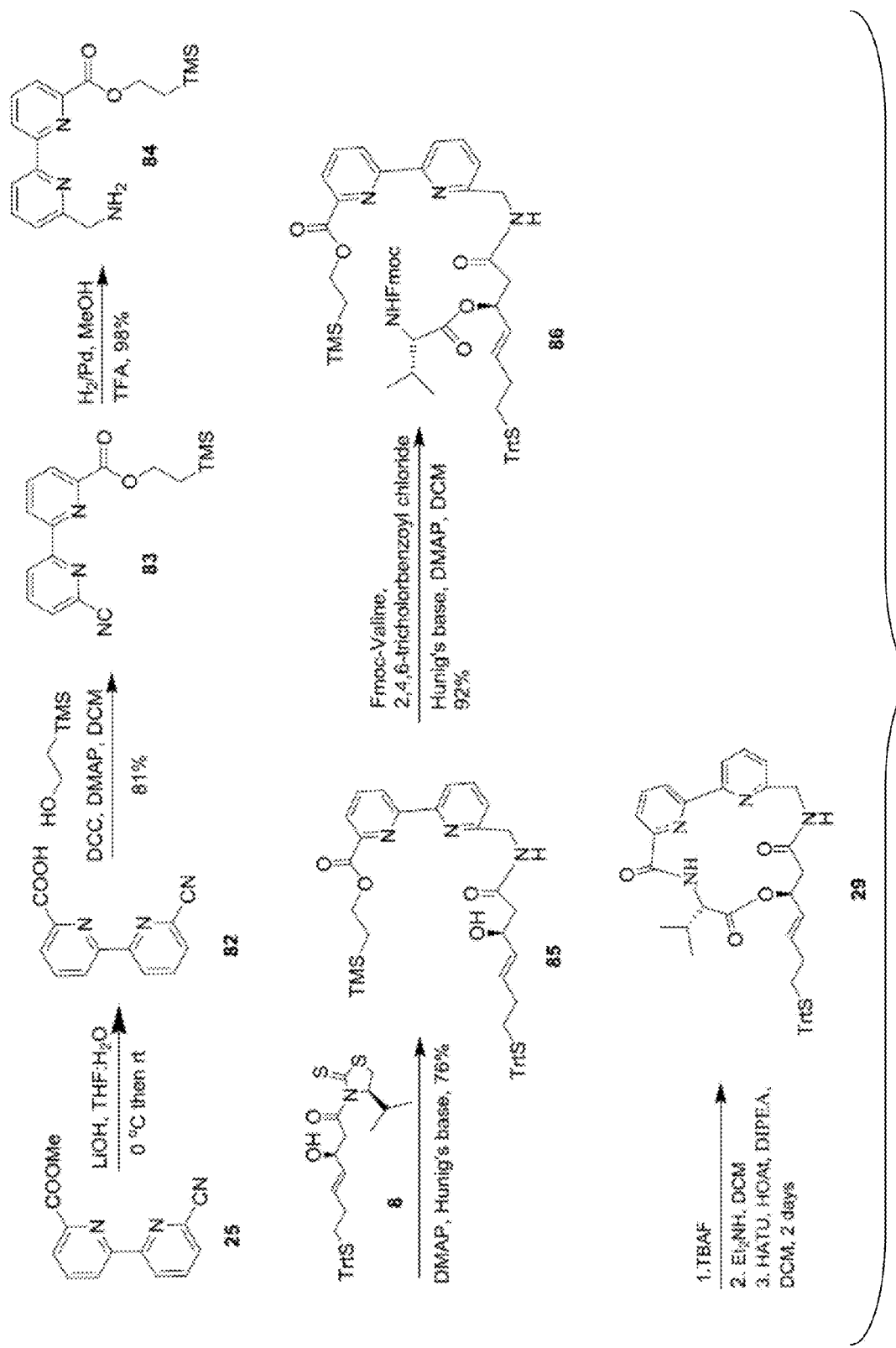
FIG. 15 – Scheme 11

HDAC INHIBITORS AS ANTI-CANCER AGENTS

RELATED APPLICATIONS

This application claims priority to U.S. Provisional Application Ser. No. 61/993,608 filed under 35 U.S.C. §111(b) on May 15, 2014, the disclosure of which is incorporated herein by reference in its entirety.

STATEMENT REGARDING FEDERALLY SPONSORED RESEARCH

This invention was made with no government support. The government has no rights in this invention.

BACKGROUND OF THE INVENTION

Cancer remains the second most common cause of death, accounting for nearly 1 out of every 4 deaths in the United States. It is estimated that more than 1.7 million new cases of cancer will be diagnosed in the United States in the year 2014 alone.

Aberrant epigenetic silencing of tumor suppressor genes is believed to result in tumorigenesis. Aberrant epigenetic silencing could occur as a result of changes in covalent modification of histone proteins. Enzymatic modifications such as acetylation, methylation, and phosphorylation of the lysine side chains in the N-terminus of histones regulate the access to DNA by transcriptional factors, thereby regulating gene expression. Histone acetylation is modulated by two protein families, histone acetyltransferases (HATs) and histone deacetylases (HDACs).

Histone deacetylases (HDACs) are a family of enzymes that catalyzes the de-acteylation of lysine amino acid side chains of histones in chromatin. HDACs remove the acetyl group from lysine residues of histone proteins to form a transcriptionally inactive condensed form of chromatin. This results in a closed, transcriptionally inactive chromatin state, which can result in silencing of tumor suppressor genes and promoting cancer initiation and/or progression. Thus, HDACs play an important role in gene expression. Inhibition of HDACs may be used to reactivate these undesirably silenced genes in the epigenetic regulation of gene expression without changing DNA sequences for developing anti-cancer agents.

HDAC proteins are a family of at least 18 enzymes classified into four groups based on their size, cellular localization, active catalytic site numbers, and homology to yeast HDAC proteins: class I includes HDAC 1, -2, -3, and -8; class IIa includes HDAC4, -5, -7, and -9; class IIb includes HDAC6 and -10; class III includes sirtuin proteins; and class IV includes HDAC11.

HDAC inhibitors reactivate silent tumor suppressor genes, resulting in cancer cell apoptosis. HDAC inhibitors block tumor cell proliferation by inducing cell differentiation, cell cycle arrest, and/or apoptosis, and these compounds make up some of the therapies currently approved or in clinical trials for cancer chemotherapy. Class I HDAC isoforms are regarded as promising cancer targets. Two HDAC inhibitors, suberoylanilide hydroxamic acid (SAHA, Vorinostat), and FK228 (romidepsin), have been approved by the USFDA for the treatment of cutaneous T-cell lymphoma (CTCL). The compound SAHA, with a hydroxamic acid moiety as the metal binding domain, is a pan-inhibitor of HDACs, non-selective for all HDAC isoforms. FK228 is a class I selective inhibitor. The metal binding domain of FK228 is a thiol masked as a cyclic disulfide bond with a cysteine residue of the depsipeptide core. A number of other HDAC inhibitors are in different stages of clinical studies. However, there is a need for isoform-selective or class-selective inhibitors for higher therapeutic potential and reduced side effects. There is also a need for the development of more potent HDAC inhibitors, as well as HDAC inhibitors not prone to drug resistance. It would also be useful to synthesize selective HDAC inhibitors that are useful as probes to determine the physiological/pathogenic role of individual HDAC isoforms.

SUMMARY OF THE INVENTION

Provided herein is a compound having the structural formula of Formula XV:

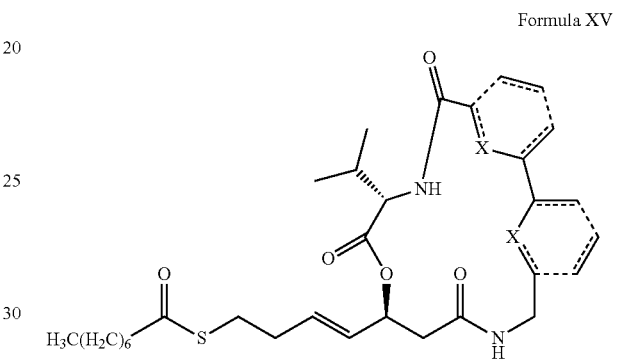

Formula XV wherein dashed lines represent bonds that may be present or absent; and each X is independently O, N, or $NR_1$, wherein $R_1$ is selected from the group consisting of methyl, aryl, alkaryl, hydrogen, and ether. Also provided are salts, stereoisomers, racemates, prodrugs, solvates, and hydrates thereof. In certain embodiments, the dashed lines are present.

In certain embodiments, the compound has the structural formula of Formula I:

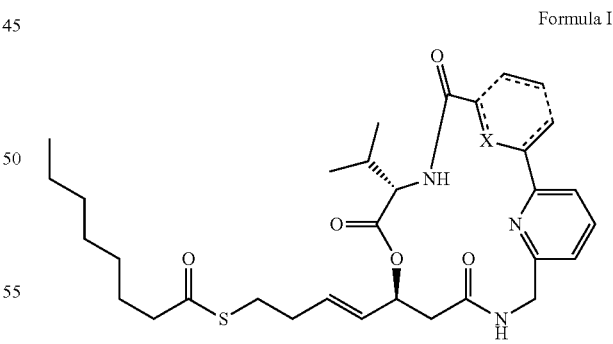

Formula I wherein dashed lines represent bonds that may be present or absent; X is either N or $NR_1$; and $R_1$ is selected from the group consisting of: methyl, aryl, alkaryl, hydrogen, and ether. Also provided are salts, stereoisomers, racemates, prodrugs, solvates, and hydrates thereof. In certain embodiments, the dashed lines are present.

In certain embodiments, $NR_1$ is selected from the group consisting of methylamino-, benzylamino-, and 4-(trifluoromethyl)benzylamino-. In certain embodiments, the dashed lines are present, and X is N. In certain embodiments, the dashed lines are absent, and NR$_1$ is methylamino-. In certain embodiments, the dashed lines are absent, and NR$_1$ is benzylamino-. In certain embodiments, the dashed lines are absent, and NR$_1$ is 4-(trifluromethyl)benzylamino-.

In certain embodiments, the compound has the structural formula of Formula IV:

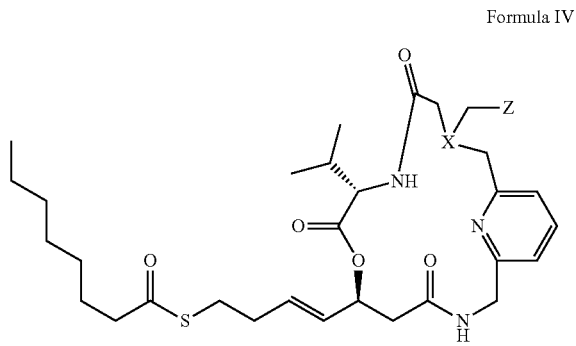

Formula IV wherein Z is selected from the group consisting of H, phenyl, 4-methoxyphenyl, 4-(trifluromethane)phenyl, 4-chlorophenyl, 1-napthyl, and 4-methylphenyl. In particular embodiments of Formula IV, X is N and Z is selected from the group consisting of 4-chlorophenyl, 1-napthyl, and 4-methylphenyl.

In certain embodiments, the compound consists essentially of Formula V:

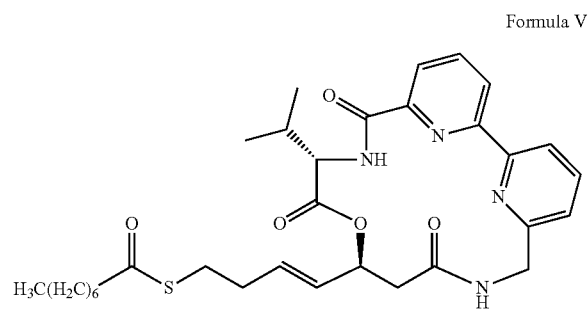

Formula V

In certain embodiments, the compound consists essentially of Formula VI:

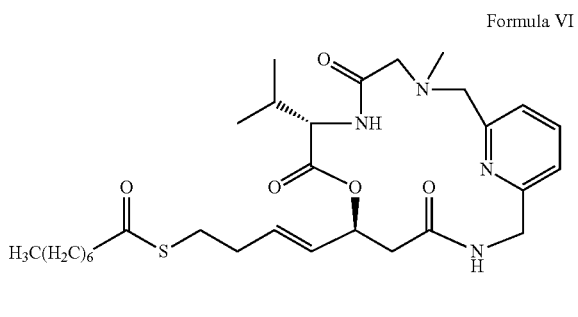

Formula VI

In certain embodiments, the compound consists essentially of Formula VII:

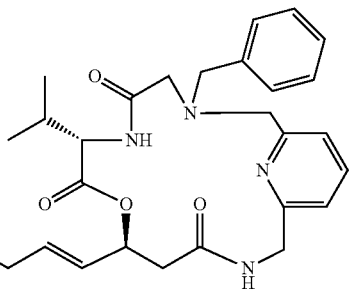

Formula VII

In certain embodiments, the compound consists essentially of Formula VIII:

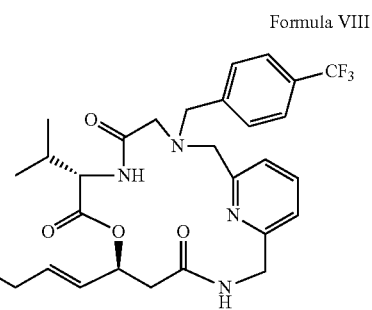

Formula VIII

In certain embodiments, the compound consists essentially of Formula VIX:

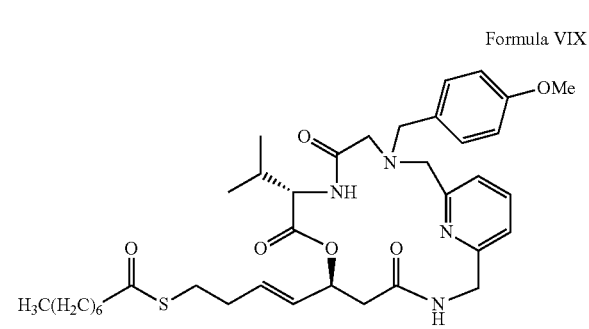

Formula VIX

In certain embodiments, the compound consists essentially of Formula X:

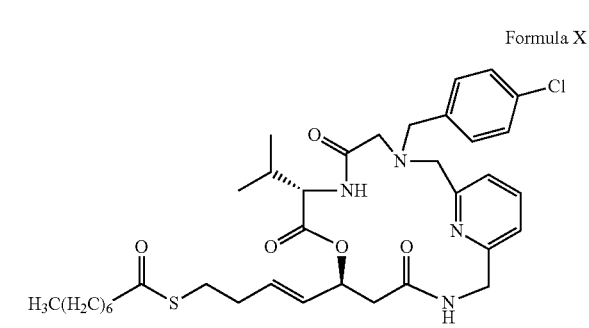

Formula X

In certain embodiments, the compound consists essentially of Formula XI:

Formula XI

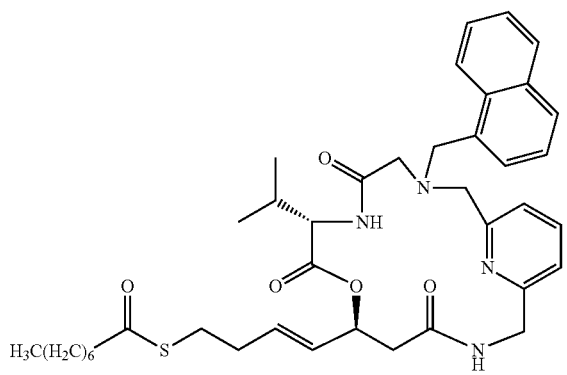

In certain embodiments, the compound consists essentially of Formula XII:

Formula XII

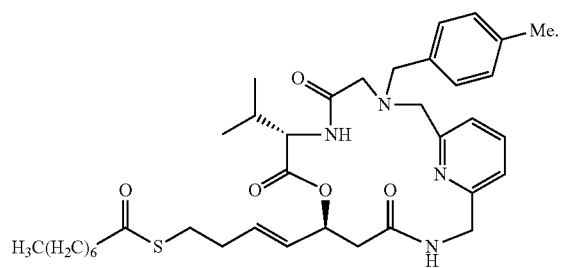

In certain embodiments, the compound consists essentially of Formula II:

Formula II

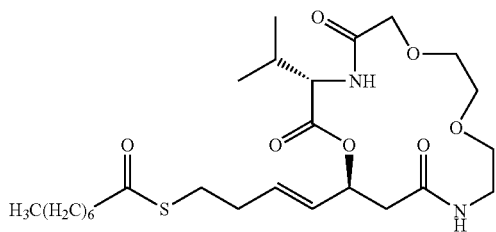

Also provided are salts, stereoisomers, racemates, prodrugs, solvates, and hydrates thereof.

Further provided is a pharmaceutical composition comprising an effective amount of a compound described herein and a pharmaceutically acceptable excipient, diluent, or carrier. In certain embodiments, the effective amount is from about 5 µM to about 10 µM. In certain embodiments, the compound is a compound of Formula V.

Further provided is a method of making a largazole analogue, the method comprising the steps of effecting an aldol reaction between an aldehyde and acetyl Nagao compound to produce an alcohol fragment, transferring an acyl group from the alcohol fragment to an amine to produce an alcohol intermediate, esterifying the alcohol intermediate with Fmoc-valine to produce a precursor, macrolactamizing the precursor to produce a cyclized intermediate having a trityl group, removing the trityl group to produce a thiol, and esterifying the thiol to produce a largazole analogue.

In certain embodiments, the aldehyde is produced by a Michael addition of triphenylmethanethiol to acrolein to produce an aldehyde intermediate, followed by reaction of the aldehyde intermediate with (cyanomethyl)triphenylphosphorane. In certain embodiments, the aldehyde is isomerized prior to the aldol reaction. In certain embodiments, the acyl transfer is conducted in the presence of DMAP. In certain embodiments, the esterification comprises Yamaguchi esterification conditions, and the precursor is acyclic. In certain embodiments, the macrolactamizing comprises methyl ester hydrolysis, Fmoc removal, and cyclization to a macrocyclic depsipeptide ring. In certain embodiments, the trityl group is removed with TFA. In certain embodiments, the thiol esterification is conducted in the presence of octanoyl chloride, Hunig's base, and DMAP.

In certain embodiments, the amine is produced by a method comprising the steps of reacting an amine alcohol with Boc anhydride to obtain a N-protected alcohol, alkylating the N-protected alcohol with methyl iodoacetate to produce a N-protected ester, and deprotecting the N-protected ester to produce an amine ester.

In certain embodiments, the amine is produced by a method comprising the steps of reacting 2-bromo-6-methylpyridine with Bu—Li and trimethyltin chloride to produce a trimethyltin intermediate, subjecting the trimethyltin intermediate to Stille coupling with a pyridine to produce a bipyridine intermediate, oxidizing the bipyridine intermediate to produce a carboxylic acid, reacting the carboxylic acid with methanol to produce a methyl ester, reacting the methyl ester with potassium cyanide and Cu(I) cyanide to produce a nitrile, and reducing the nitrile by hydrogenation to produce a methyl amine.

In certain embodiments, the amine is produced by a method comprising the steps of treating a suspension of a pyridine, silver oxide, and potassium iodide with tosyl chloride to produce a mono-tosylated product; heating the mono-tosylated product with sodium azide to produce an azide; tosylating the azide to produce a tosylated azide; displacing the tosyl group of the tosylated azide with an amine precursor to produce a tertiary amine azide; and reducing the tertiary amine azide to produce an amine.

In certain embodiments, the amine is produced by a method comprising the steps of esterifying a bromoacetic acid with 2-trimethylsilylethyl alcohol to produce an ester, reacting the ester with a substituted benzyl amine and a naphthylmethyl amine to produce a nucleophilic substitution product, reacting the nucleophilic substitution product with tosyl azide to produce a tertiary amine azide, and reducing the tertiary amine azide to produce a primary amine.

In certain embodiments, the amine is produced by a method comprising the steps of hydrolyzing a cyano methyl ester to produce a cyano carboxylic acid, converting the cyano carboxylic acid to a cyano trimethylsilylethyl ester, and reducing the cyano trimethylsilylethyl ester to produce an amine.

Further provided is a method of making a largazole analogue, the method comprising the steps of removing Fmoc and trimethylsilyethyl protecting groups from an acyclic intermediate simulteanously to produce an unprotected acyclic intermediate, cycling the unprotected acyclic intermediate to produce a cyclized intermediate having at rityl group, removing the trityl group with TFA to produce a thiol, drying the thiol azeotropically with toluene to produce a dried thiol, and esterifying the dried thiol with octanoyl chloride in the presence of Hunig's base and DMAP to produce a largazole analogue. In certain embodiments, the acyclic intermediate is produced by esterifying an intermediate with Fmoc-valine to obtain an acyclic intermediate. In particular embodiments, the intermediate is produced by subjecting a primary amine to acyl transfer to produce an intermediate. In particular embodiments, the primary amine is produced by reducing an azide group of an amine to obtain a primary amine. In particular embodiments, the amine is produced by reacting a nucleophilic substitution product with tosylate to produce a tertiary amine. In particular embodiments, the nucleophilic substitution product is produced by reacting an ester with a substituted benzyl amine and 1-(aminomethyl)-naphthalene to produce a nucleophilic substitution product. In particular embodiments, the ester is produced by esterifying bromoacetic acid with 2-trimethylsilylethyl alcohol to produce an ester.

Further provided is a method of inhibiting cell proliferation, the method comprising administering to cells an effective amount of a compound disclosed herein, and inhibiting proliferation of the cells. In certain embodiments, the cells are human cells. In certain embodiments, the cells are cancer cells. In certain embodiments, the effective amount of the compound is about 10 μM. In particular embodiments, the cancer is selected from the group consisting of leukemia, non-small cell lung cancer, colon cancer, CNS cancer, melanoma, ovarian cancer, renal cancer, prostate cancer, and breast cancer. In particular embodiments, the cancer is colon cancer and the compound consists essentially of a compound having the structural formula of Formula VI:

Formula VI

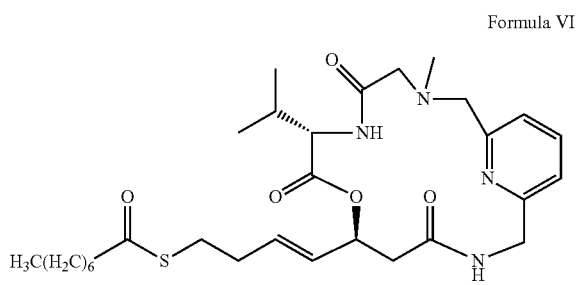

In particular embodiments, the compound consists essentially of a compound having the structural formula of Formula V:

Formula V

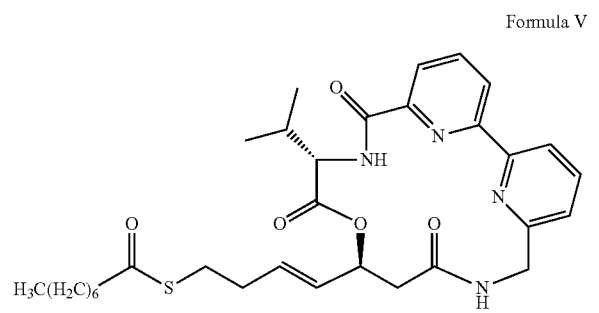

In particular embodiments, the compound consists essentially of a compound having the structure formula of Formula V, and the cancer is either melanoma or renal cancer.

In particular embodiments, the cancer is colon cancer and the compound consists essentially of a compound having the structural formula of Formula II:

Formula II

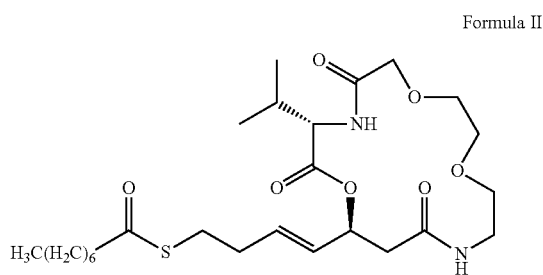

Further provided is a kit for making a largazole analogue, the kit comprising a first container housing an alcohol fragment, a second container housing an amine, and a third container housing one or more reagents selected from the group consisting of DMAP, Hunig's base, Fmoc-valine, TFA, and TIPS.

BRIEF DESCRIPTION OF THE DRAWING

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

PRIOR ART FIGS. 1A-1B: Structural formula of HDAC inhibitor largazole (1, FIG. 1A), and a table showing the selectivity of largazole for cancer cells (FIG. 1B).

In FIG. 2B, the linker is depicted in blue, and the zinc binding moiety is depicted in red.

FIG. 5: Scheme 1, depicting the retrosynthetic analysis of largazole analogues JA1-JA6, AA1-AA2, and RF1.

FIG. 6: Scheme 2, depicting the synthesis of aldehyde 11 and alcohol 8.

FIG. 7: Scheme 3, depicting the synthesis of amine 18.

FIG. 8: Scheme 4, depicting the synthesis of analogue JA1.

FIG. 9: Scheme 5, depicting the synthesis of amine 26.

FIG. 10: Scheme 6, depicting the synthesis of analogue JA2.

FIG. 11: Scheme 7, depicting the synthesis of amines 42-45.

FIG. 12: Scheme 8, depicting the synthesis of analogues JA3-JA6.

FIG. 13: Scheme 9, depicting the synthesis of intermediates 67-69.

FIG. 14: Scheme 10, depicting the synthesis of analogues AA1, AA2, and RF1.

FIG. 15: Scheme 11, depicting an alternative, improved synthesis of intermediate 29.

Figure 22C:
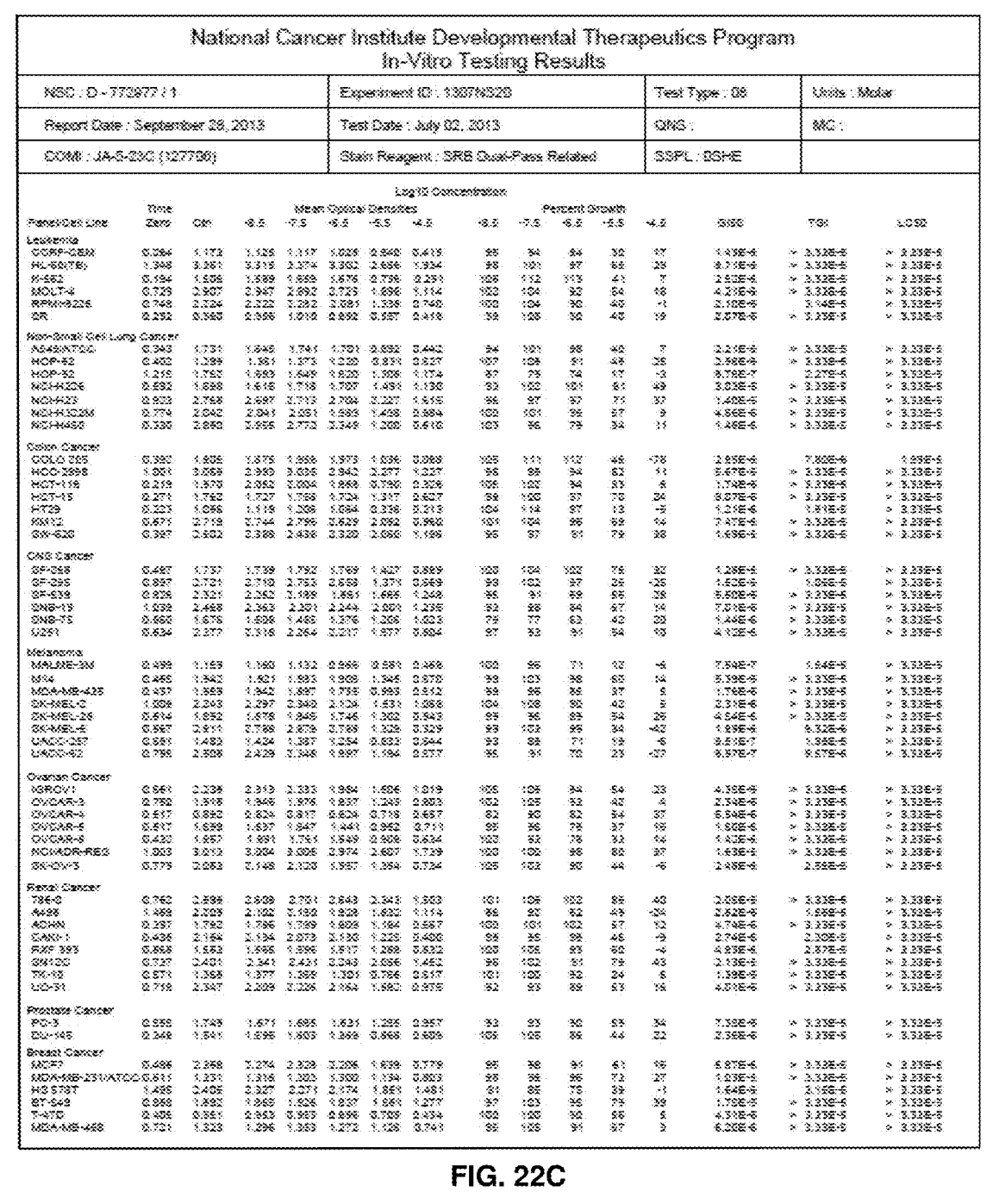

FIGS. 22A-22D: Results of dose response evaluation of JA1. FIG. 22A shows a graph of percentage growth versus $\log_{10}$ of sample concentration for all cell lines. FIG. 22B shows dose response curves for leukemia, non-small cell lung cancer, colon cancer, CNS cancer, melanoma, ovarian cancer, renal cancer, prostate cancer, and breast cancer cell lines. FIG. 22C shows in vitro testing results in leukemia, non-small cell lung cancer, colon cancer, CNS cancer, melanoma, ovarian cancer, renal cancer, prostate cancer, and breast cancer cell lines. FIG. 22D shows mean graphs of the in vitro testing results.

Figure 23C:
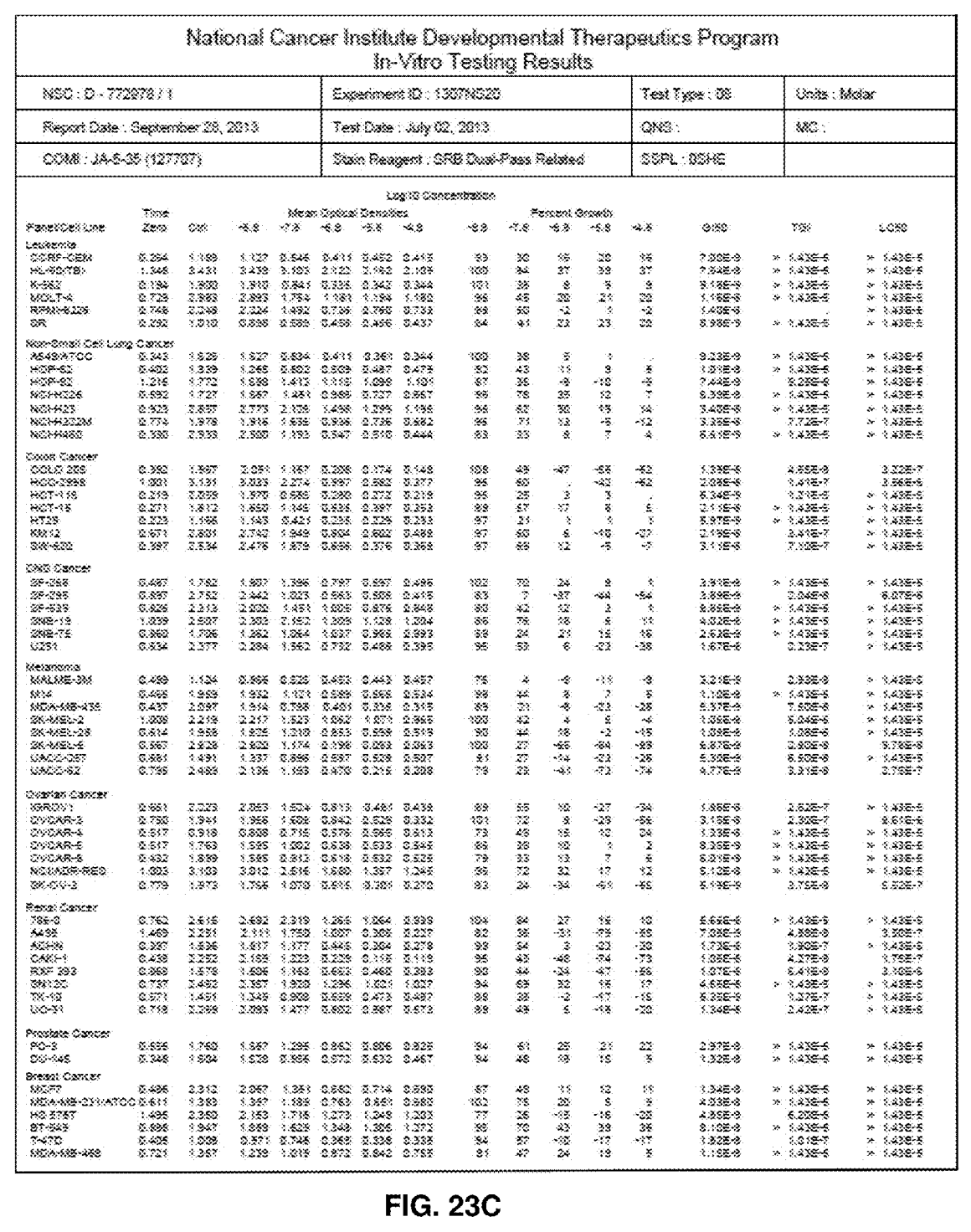

FIGS. 23A-23D: Results of dose response evaluation of JA2. FIG. 23A shows a graph of percentage growth versus $\log_{10}$ of sample concentration for all cell lines. FIG. 23B shows dose response curves for leukemia, non-small cell lung cancer, colon cancer, CNS cancer, melanoma, ovarian cancer, renal cancer, prostate cancer, and breast cancer cell lines. FIG. 23C shows in vitro testing results in leukemia, non-small cell lung cancer, colon cancer, CNS cancer, melanoma, ovarian cancer, renal cancer, prostate cancer, and breast cancer cell lines. FIG. 23D shows mean graphs of the in vitro testing results.

Figure 24C:
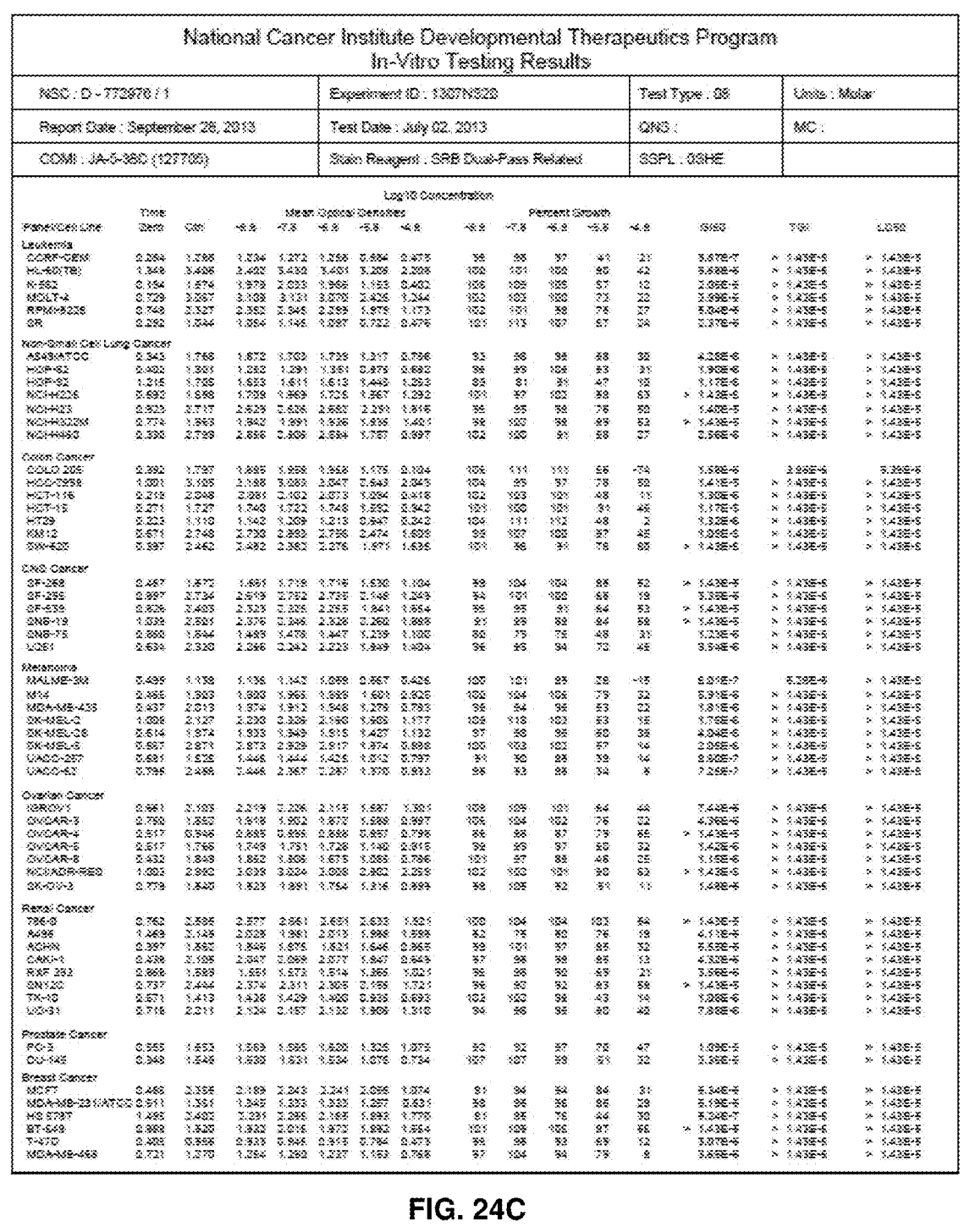

FIGS. 24A-24D: Results of dose response evaluation of JA3. FIG. 24A shows a graph of percentage growth versus $\log_{10}$ of sample concentration for all cell lines. FIG. 24B shows dose response curves for leukemia, non-small cell lung cancer, colon cancer, CNS cancer, melanoma, ovarian cancer, renal cancer, prostate cancer, and breast cancer cell lines. FIG. 24C shows in vitro testing results in leukemia, non-small cell lung cancer, colon cancer, CNS cancer, melanoma, ovarian cancer, renal cancer, prostate cancer, and breast cancer cell lines. FIG. 24D shows mean graphs of the in vitro testing results.

DETAILED DESCRIPTION OF THE INVENTION

Figure 1A:
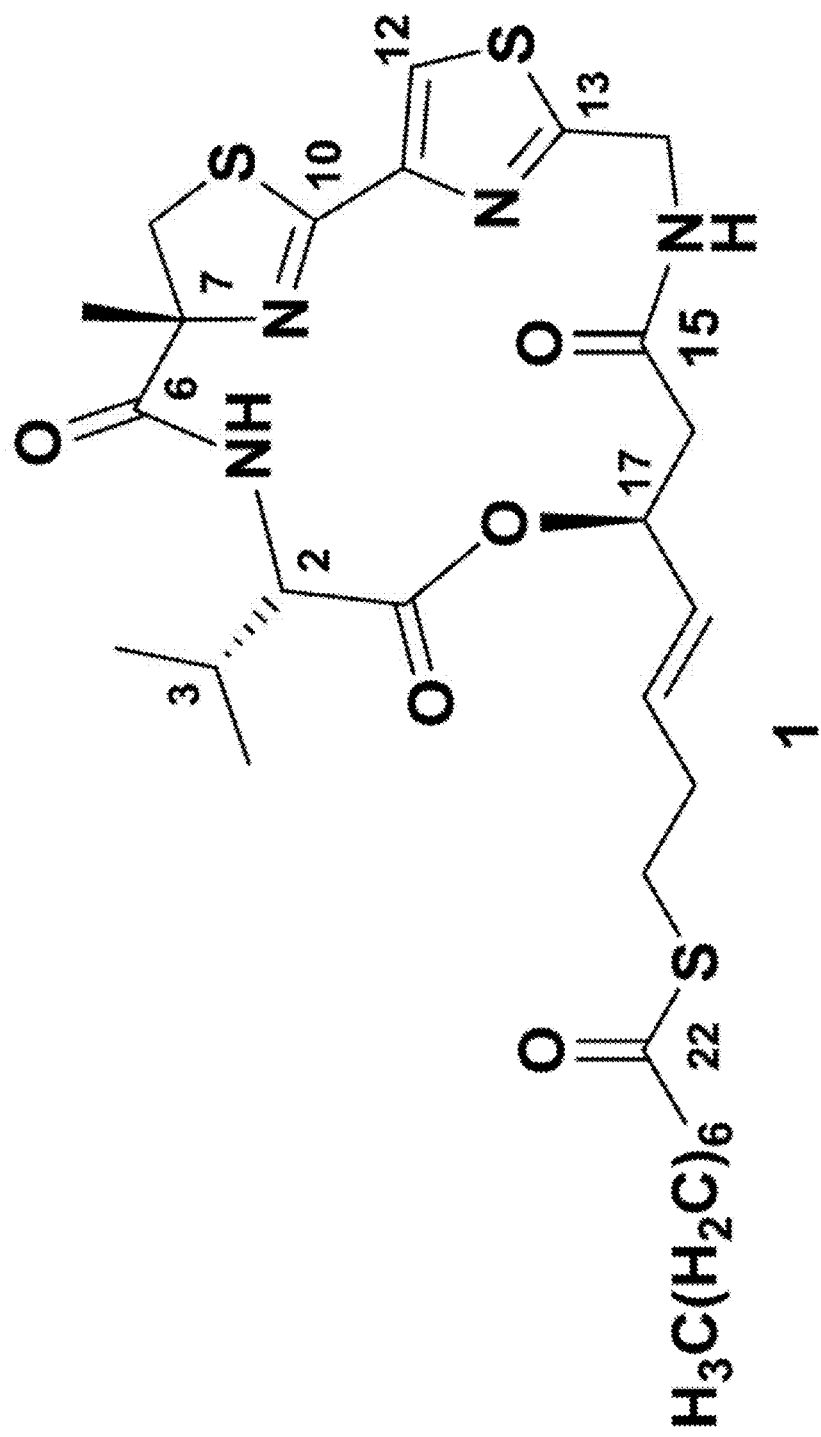

Throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this invention pertains.

DEFINITIONS

For convenience, various terms used herein are defined prior to further description of the various embodiments of the present disclosure.

Unless stereochemistry is specifically indicated, all stereoisomers of the compounds herein are included, as pure compounds as well as mixtures thereof.

The term "composition" as used herein is intended to encompass a product comprising the specified ingredients in the specified amounts, as well as any product that results, directly or indirectly, from combinations of the specified ingredients in the specified amounts.

The term "protecting group" as used herein refers to a group which is introduced onto a functional group in a compound and which modifies that functional group's chemical reactivity. Typically, the protecting group modifies the functional group's chemical activity in such a way that it renders the functional group chemically inert to the reaction conditions used when a subsequent chemical transformation is effected on the compound.

The term "alkyl" refers to monovalent alkyl groups having from 1 to 50 carbon atoms, preferably having from 1 to 10 carbon atoms, and more preferably having from 1 to 6 carbon atoms. This term is exemplified by groups such as methyl, ethyl, n-propyl, iso-propyl, n-butyl, iso-butyl, n-hexyl, and the like. "Substituted alkyl" refers to an alkyl group, preferably of from 1 to 10 carbon atoms, having from 1 to 3 substituents selected from the group consisting of alkoxy, substituted alkoxy, acyl, acylamino, amino, aminoacyl, aminocarboxy esters, cyano, cycloalkyl, halogen, hydroxyl, carboxyl, carboxylalkyl, oxyacyl, oxyacylamino, thiol, thioalkoxy, substituted thioalkoxy, aryl, heteroaryl, heterocyclic, aryloxy, thioaryloxy, heteroaryloxy, thioheteroaryloxy, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, and heterocyclic.

The term "aryl" refers to an unsaturated aromatic carbocyclic group, preferably of from 6 to 14 carbon atoms, having a single ring (e.g., phenyl) or multiple condensed rings (e.g., naphthyl or anthryl), preferably having from 1 to 3 rings. Preferred aryls include phenyl, naphthyl, and the like. Unless otherwise constrained by the definition for the aryl substituent, such aryl groups can optionally be substituted with from 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, heterocyclic, and the like. Preferred substituents include alkyl, alkoxy, halo, cyano, nitro, trihalomethyl, and thioalkoxy.

The term "alkaryl" refers to an aryl group with an alkyl substitution. Generally, alkaryl groups herein contain from 6 to 30 carbon atoms. The term "aralkyl" refers to alkylene-aryl groups preferably having from 1 to 10 carbon atoms in the alkylene moiety and from 6 to 10 carbon atoms in the aryl moiety. Such alkaryl groups are exemplified by benzyl, phenethyl, and the like.

The term "ether" refers to a compound having and R—O—R' group, where R and R' are each independently alkyl or aryl groups.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

It will be appreciated by one of ordinary skill in the art that asymmetric centers may exist in any of the compounds disclosed herein. Thus, the compounds and pharmaceutical compositions thereof may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents or organic compounds. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents or organic compounds. Combinations of substituents and variables envisioned are preferably those that result in the formation of stable compounds useful in the treatment, for example, of proliferative disorders including, but not limited to, cancer.

The term "stable" as used herein refers to compounds which possess stability sufficient to allow manufacture and which maintain the integrity of the compound for a sufficient period of time to be detected and preferably for a sufficient period of time to be useful for the purposes detailed herein.

The term "therapeutically effective amount" as used herein means that amount of active compound or pharmaceutical agent that elicits the biological or medicinal response in a tissue system, animal, or human that is being sought by a researcher, veterinarian, medical doctor, or other clinician, which includes alleviation of the symptoms of the disease or disorder being treated.

The term "pharmaceutically acceptable salt" means a salt of a compound. Suitable pharmaceutically acceptable salts of the compounds include acid addition salts which may, for example, be formed by mixing a solution of the compound with a solution of a pharmaceutically acceptable acid.

The term "pharmaceutically acceptable carrier" means a medium that is used to prepare a desired dosage form of the compound. A pharmaceutically acceptable carrier includes solvents, diluents, or other liquid vehicles; dispersion or suspension aids; surface active agents; isotonic agents; thickening or emulsifying agents; preservatives; solid binders; lubricants; and the like.

The abbreviation "HDAC" refers to a histone deacetylase. The abbreviation "HAT" refers to a histone acetyltransferase. The abbreviation "SAHA" refers to suberoylanilide hydroxamic acid. The abbreviation "HCT116" refers to a particular human colorectal carcinoma cell line. The abbreviation "HATU" refers to 2-(1H-azabenzotriazol-1-yl)-1,1,3,3-tetramethyluronium hexafluorophosphate. The abbreviation "HDACi" refers to a histone deacetylase inhibitor. The abbreviation "NMR" refers to nuclear magnetic resonance. The abbreviation "SAR" refers to structure-activity relationship. The abbreviation "TIPS" refers to triisopropylsilane. The abbreviation "TFA" refers to trifluoroacetic acid, and the abbreviation "TFAA" refers to trifluoroacetic anhydride. The abbreviation "HOAt" refers to 1-hydroxy-7-azabenzotriazole. The abbreviation "DMAP" refers to 4-dimethylaminopyridine. The abbreviation "MTS" refers to 3-(4,5-dimethylthiazol-2-yl)-5-(3-carboxymethoxy-phenyl)-2-(4-sulfophenyl)-2H-tetrazolium. The abbreviation "TLC" refers to thin layer chromatography. The abbreviation "CTCL" refers to cutaneous T-cell lymphoma. The term "Hunig's base" and the abbreviation DIPEA refer to N,N-diisopropylethylamine. The term "Fmoc" refers a fluorenylmethyloxycarbonyl group.

General Description

Aberrant epigenetic silencing of tumor suppressor genes can be reversed. This has resulted in the targeting of enzymes responsible for these modifications being one therapeutic approach in cancer. Mechanisms of epigenetic silencing include DNA methylation and modification of key residues of histone tails. Lysine residues of histone tails can be acetylated/deacetylated, which can alter gene expression. Histone acetylation status is regulated by two enzymes, histone acetyl transferases (HAT), which acetylate lysine tails of histone proteins, and histone deacetylases (HDAC), which deacetylate them.

HDAC inhibitor pharmacophores have three key structural elements: (a) a metal binding domain, which interacts with $Zn^{2+}$ ions in the active site; (b) a surface recognition cap group, which interacts with hydrophobic residues on the rim of the active site; and (c) a linker, which occupies a hydrophobic channel, positioning the zinc binding moiety and the cap group in binding orientation and mimicking the N-acetyl lysine side chain of histone. Any one, two, or three of these three sectors may be targeted for structural alteration to achieve HDAC class and/isoform selectivity. However, in accordance with the present disclosure, the surface recognition cap group is believed to be the most amenable for such modification because it interacts with a less conserved region of the enzyme. The three structural elements are highlighted in largazole, FK228, and SAHA molecules in FIG. 2B. Largazole (1, FIGS. 1A-1B), a compound that was isolated in 2008 from a marine *cyanobacterium* of the genus *Symploca*, is a class I selective anticancer agent with potent HDAC inhibitory activity. Largazole possesses significant selective activity against highly invasive transformed human mammary epithelial cells (MDA-MB-231) and transformed fibroblastic osteosarcoma (USOS) cells over normal cell lines (NMuMG and NIH353, respectively). (FIG. 1B.) In fact, largazole is more selective than most well known anti-cancer agents like paclitaxel and doxorubicin. The anticancer activity of largazole has been shown to be mediated through the inhibition of histone deacetylases.

Figure 2A:
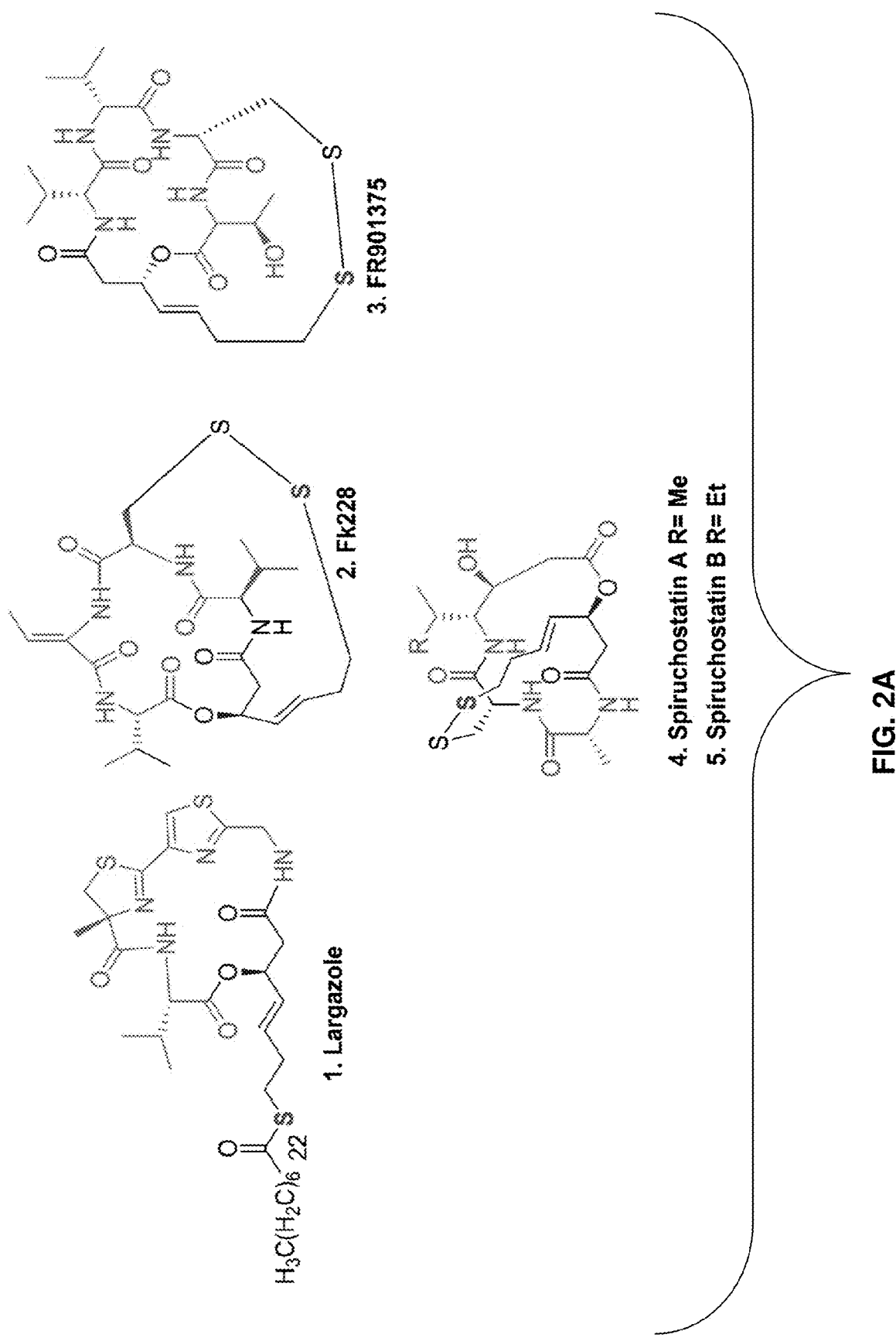
FIGS. 2A-2B: Structural formulas of various HDAC inhibitors (FIG. 2A), and a depiction of the structural binding elements of HDAC inhibitors largazole, FK228, and SAHA (FIG. 2B).
Figure 2B:
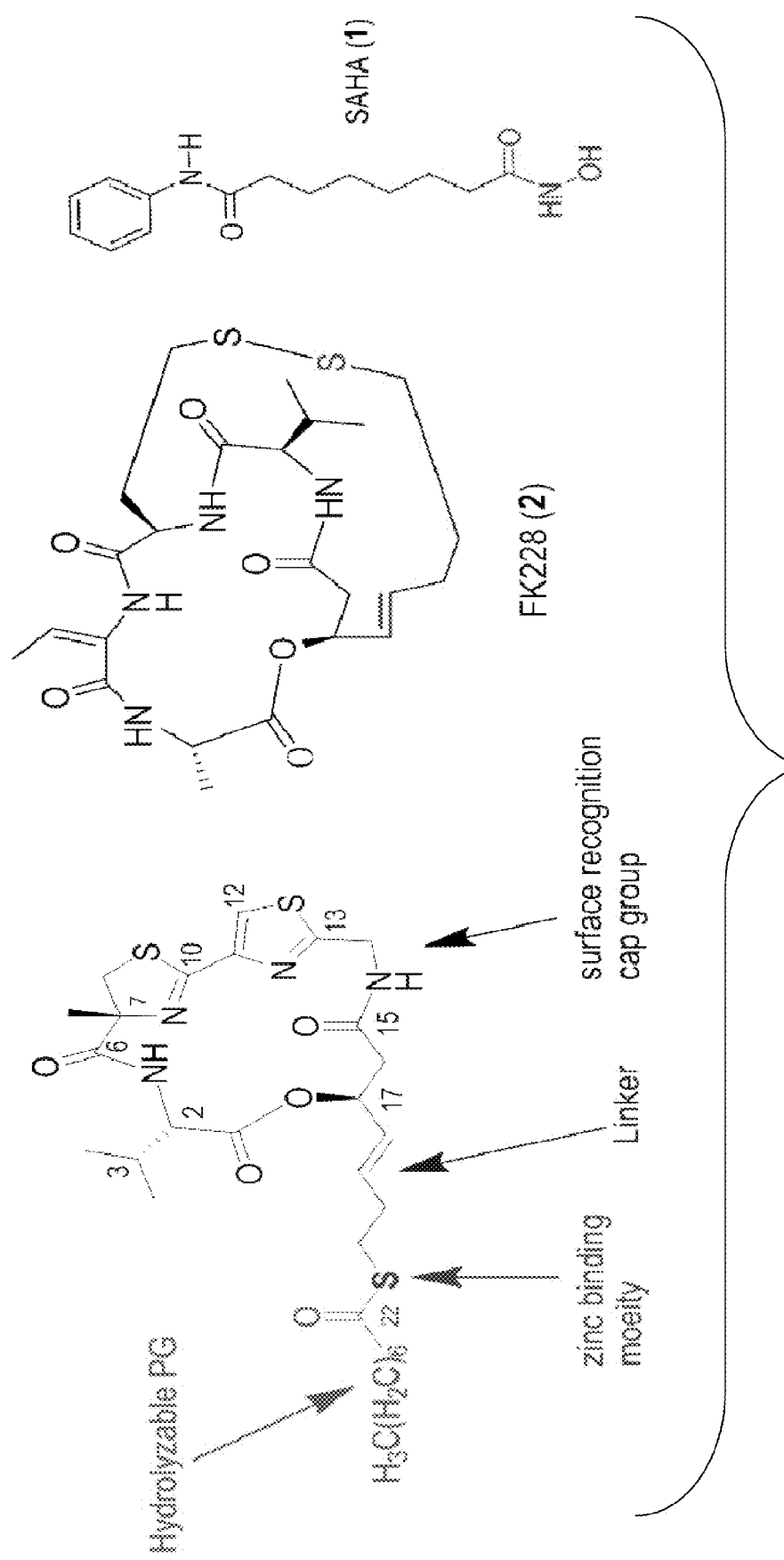

At least 18 different isoforms of human HDAC proteins have been identified, but their specific roles in cellular function and physiology are still not well understood. However, specific HDAC isoforms over-expressed in some types of cancer can be targeted to develop selective anticancer agents. The USFDA approved the pan HDACi SAHA (vorinostat) for the treatment of cutaneous T-cell lymphoma (CTCL) in 2006. A second drug, FK 228 (romidepsin), approved by the USFDA in 2009 for the same human condition, is a class I specific inhibitor of HDAC. Both molecules incorporate the essential structural features of HDAC inhibitors and consist of a metal binding domain, a surface recognition cap, and a hydrophobic linker (FIGS. 2A-2B.) The metal binding domain of SAHA is a strongly metal-chelating hydroxamic acid moiety while that of FK 228 is a thiol group generated by in situ reduction of a disulfide bridge. The large hydrophobic depsipeptide cap group of FK 228 may contribute to its more class I selective properties by interacting with less conserved regions located further away than those reachable by the smaller benzamide cap group of SAHA in the rim of the active site. Notably, tubacin and other related compounds with structural similarities to SAHA, but having a large cap group, are more selective for HDAC6 than HDAC1, underscoring the importance of the nature of the cap group in discriminating between the HDAC isoforms.

Largazole shares similar linker and zinc-binding groups with other related HDAC inhibitors such as FK228, FR901375, and spiruchostatins (FIG. 2). The zinc-binding thiol group in all of these HDAC inhibitors is masked in a prodrug form. Largazole's thioester group is hydrolyzed by cellular esterases (or lipases) to the free thiol, while in compounds 2, 3, and 4, the disulfide bridge gets reduced to free thiol by glutathione-mediated cellular reduction. Both largazole and FK228 are depispeptides, with the depsipeptide ring constituting the surface recognition cap group of both inhibitors. Both compounds also have identical linker groups and masked thiol groups as metal-binding motifs.

A number of largazole analogues have been synthesized, and their HDAC inhibitory activities have revealed some of its structure-activity relationship (SAR) requirements. Changes in all three sectors of the molecule have been effected. For example, largazole analogues incorporating multiple heteroatoms as the metal binding domain have been synthesized. As HDAC proteins are associated with many basic cellular processes, and aberrant HDAC activity is also linked to human disorders other than cancer, the effect of largazole on other disease states is also being explored. However, largazole has been reported to have no effect on the viability of rheumatoid arthritis synovial fibroblasts. Similarly, it inhibited the expression of HDAC1 and HDAC5, but enhanced HDAC6 in synovial fibroblasts. Largazole and its derivatives have been reported to selectively inhibit ubiquitin activation enzyme (E1), but largazole decreases liver fibrosis and angiogenesis by inhibiting transforming growth factor-β and vascular endothelial growth factor signaling.

The importance of thiol as the metal binding motif is evident from the lack or reduced activity of largazole analogues in which the thiol group is replaced with other groups such as benzamide, thiobenzamide, ketone, or esters functionalities, and with thioether-containing dual hetero atom combinations. For optimal activity, the linker between the metal binding motif and the depsipeptide ring has to be four atoms in length and should preferably have a trans vs cis double bond. Importantly, some structural alterations in the depsipeptide ring have been well tolerated. Replacement of sulfur atoms with oxygen atoms gives the oxazoline-oxazole analogue, which is equipotent with largazole, but the oxidation of the thizoline ring to the more stained thiazole-thiazole analogue results in reduced activity. Of note is the generation of the most potent HDACi known by replacing the thiazole ring with a pyridine ring. L-valine can be replaced with other amino acids without affecting affinity. Substitution of L-tyrosine, L-alanine, and glycine for L-valine is also well tolerated. The x-ray crystal structure of the largazole-HDAC8 complex shows that the valine side chain of largazole points directly out toward the solvent and has no effect on HDAC-largazole interaction. Therefore, without wishing to be bound by theory, the substitution of L-valine with other amino acids or even D-amino acids and disubstituted amino acids should be well tolerated provided they do not perturb the conformation of the macrocycle.

Figure 3:
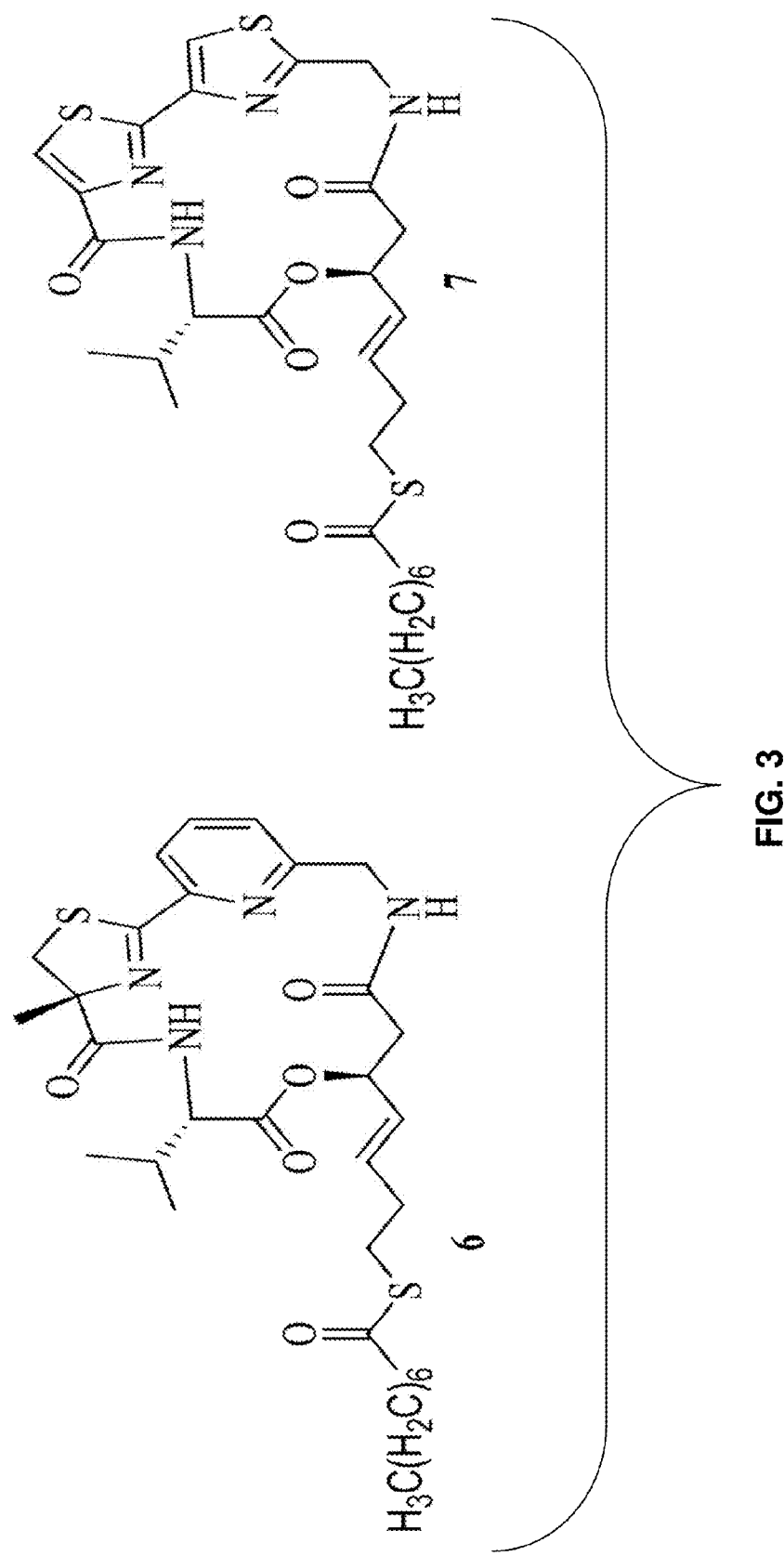
FIG. 3: Structural formulas of various largazole analogues.

The methyloxazoline-oxazole analogue of largazole shows slightly better activity than largazole. The HDAC8-largazole complex crystal structure shows that the 4-methylthiazoline-thiazole moiety interacts with the less conserved area in the rim of the binding pocket and faces toward the solvent. Bi-thiazole analogue 7, in which the thiazoline ring is replaced by a thiazole ring (FIG. 3), results in a 25-145-fold decrease in activity. The C-2 epimer of largazole retains reduced, but sub-micromolar, inhibitory potency against HDAC isoforms. However, the C-2 epimer has been found to be more potent than largazole in inhibiting the viability of prostate cancer cell lines LNCaP and PC-3, and both upregulate the expression of p21.

In accordance with the present disclosure, the lower sequence homology between different HDAC classes at the surface near the opening to the binding pocket can be exploited to design isoform-selective inhibitors. The region of the HDAC enzyme around the binding pocket consists of many grooves, which can be occupied differently by multiple cap groups to impact selectivity. This is underscored by the fact that the small cap group of SAHA interacts with the highly conserved region of the enzyme, and is unable to make contact with the variable region which is believed to be further away from the opening of the channel. The inability to interact with the variable region is believed to be responsible for its non-specificity. In contrast, the depsipeptide HDAC inhibitors (FK228, largazole) contain large and bulky recognition cap groups, which allow better interaction with the less conserved region of the surface area of the enzyme. Given that there are variations at the mouth of the active site of HDAC isoforms, structure-based modification of the largazole depsipeptide backbone can lead to molecules capable of isoform-specific inhibition, a thrust in HDAC inhibitor development.

Provided herein are largazole analogues with modifications in the depsipeptide ring. The depsipeptide ring of largazole constitutes the surface recognition cap group that interacts with the less conserved hydrophobic rim of the HDAC active site. In particular, provided herein are largazole analogues in which the thiazole-thiazoline moiety of the surface recognition cap group is replaced with other structural variants. In particular examples, the thiazole-thiazoline moiety is replaced with different aromatic and alkyl groups. The structure-activity relationship (SAR) requirements for potency and isoform selectivity have been investigated through these analogues. In certain embodiments, these largazole analogues are histone deacetylase inhibitors with potent anticancer activity. As a non-limiting example, replacing the sp$^3$ carbon at C7 of largazole with an sp$^2$ carbon is tolerated and leads to biologically active molecules. The skilled practitioner will recognize that particular modifications to the thiazole-thiazoline moiety other than those specifically described herein are nonetheless encompassed within the scope of the present disclosure.

Figure 4A:
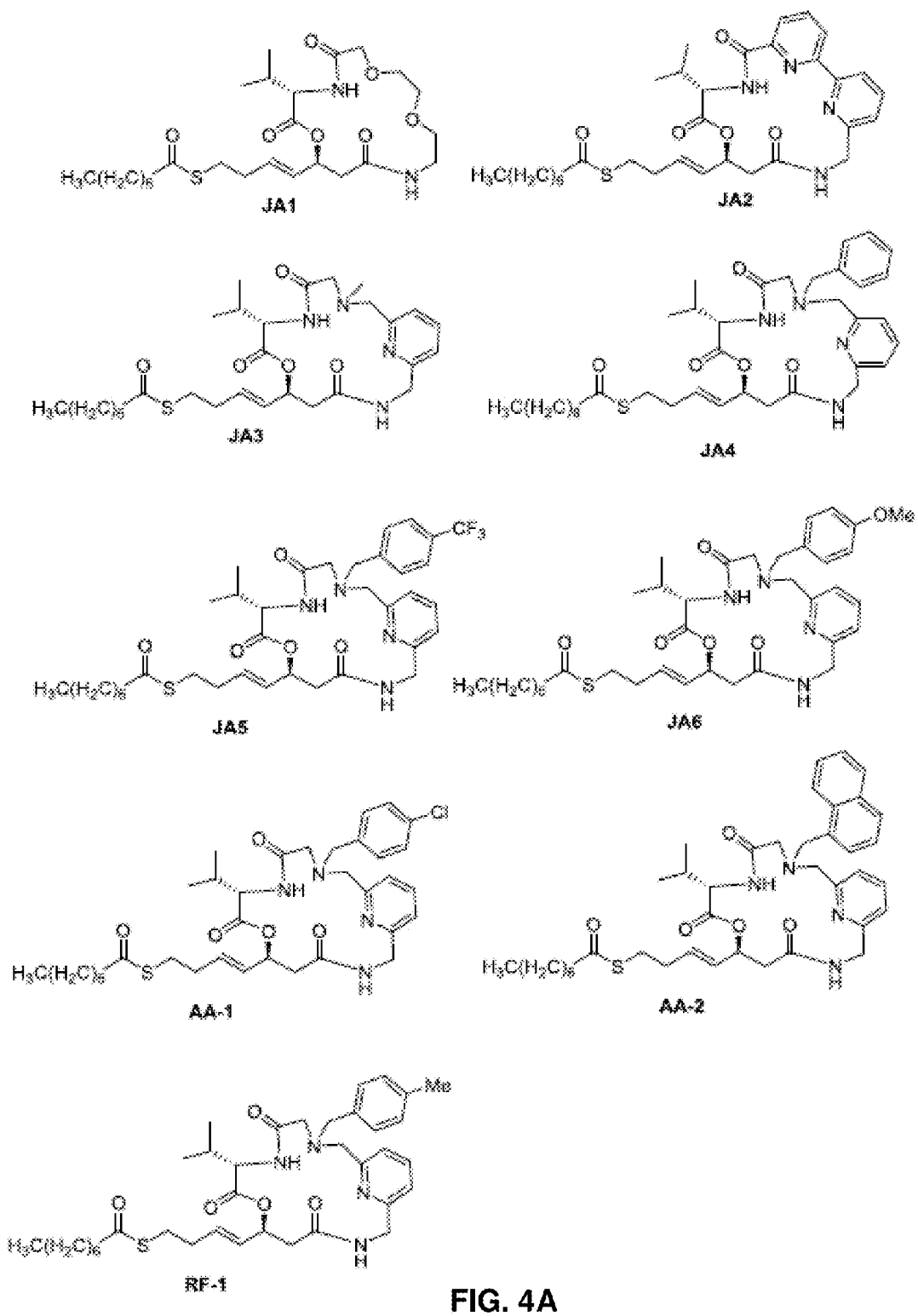
FIGS. 4A-4B: Structural formulas of analogues JA1, JA2, JA3, JA4, JA5, JA6, AA-1, AA-2, and RF-1 (FIG. 4A), and a depiction of analogues JA1-JA6 with the modified portion of the molecules shown in red (FIG. 4B).
Figure 4B:
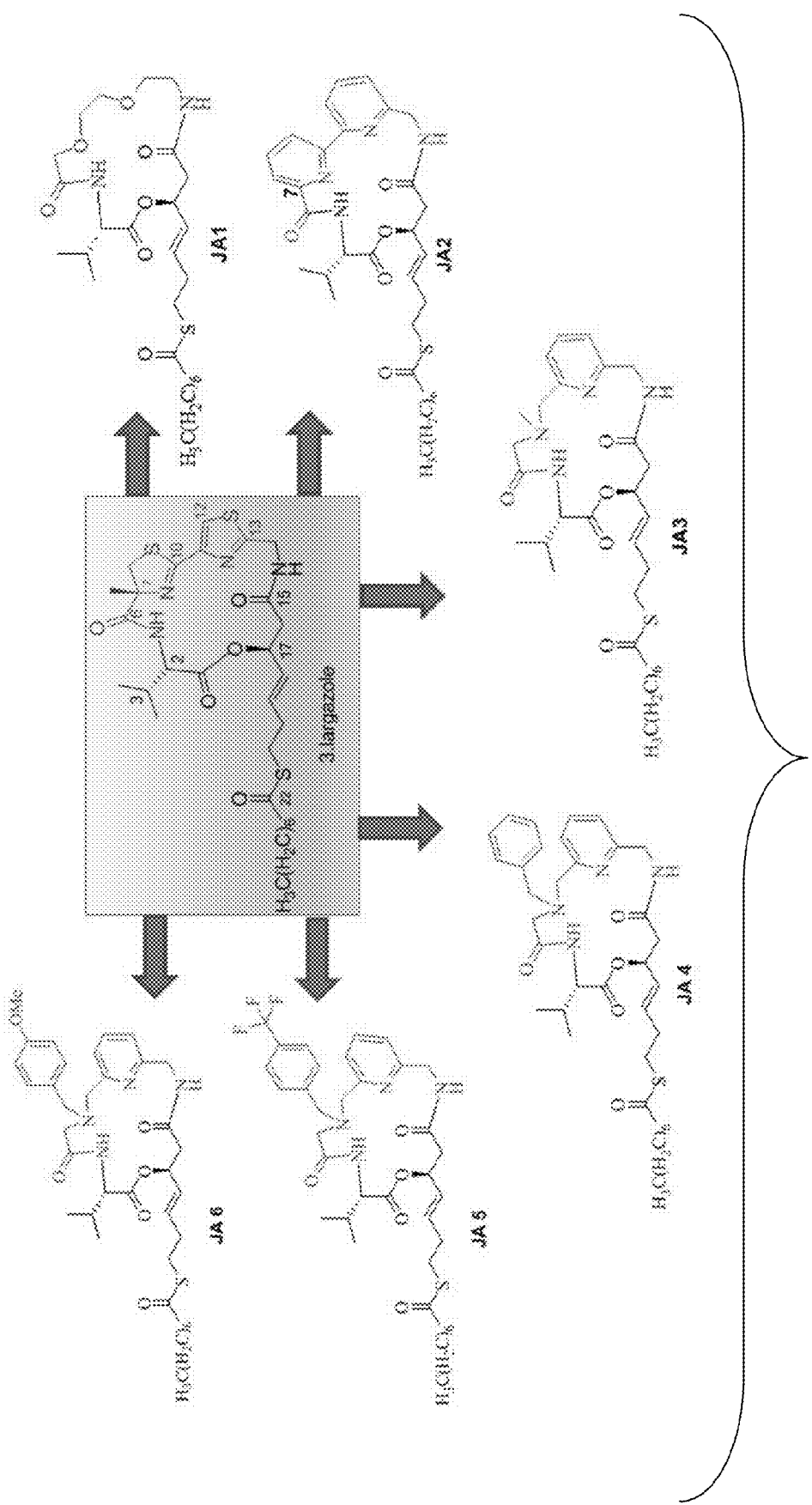
Figure 16:
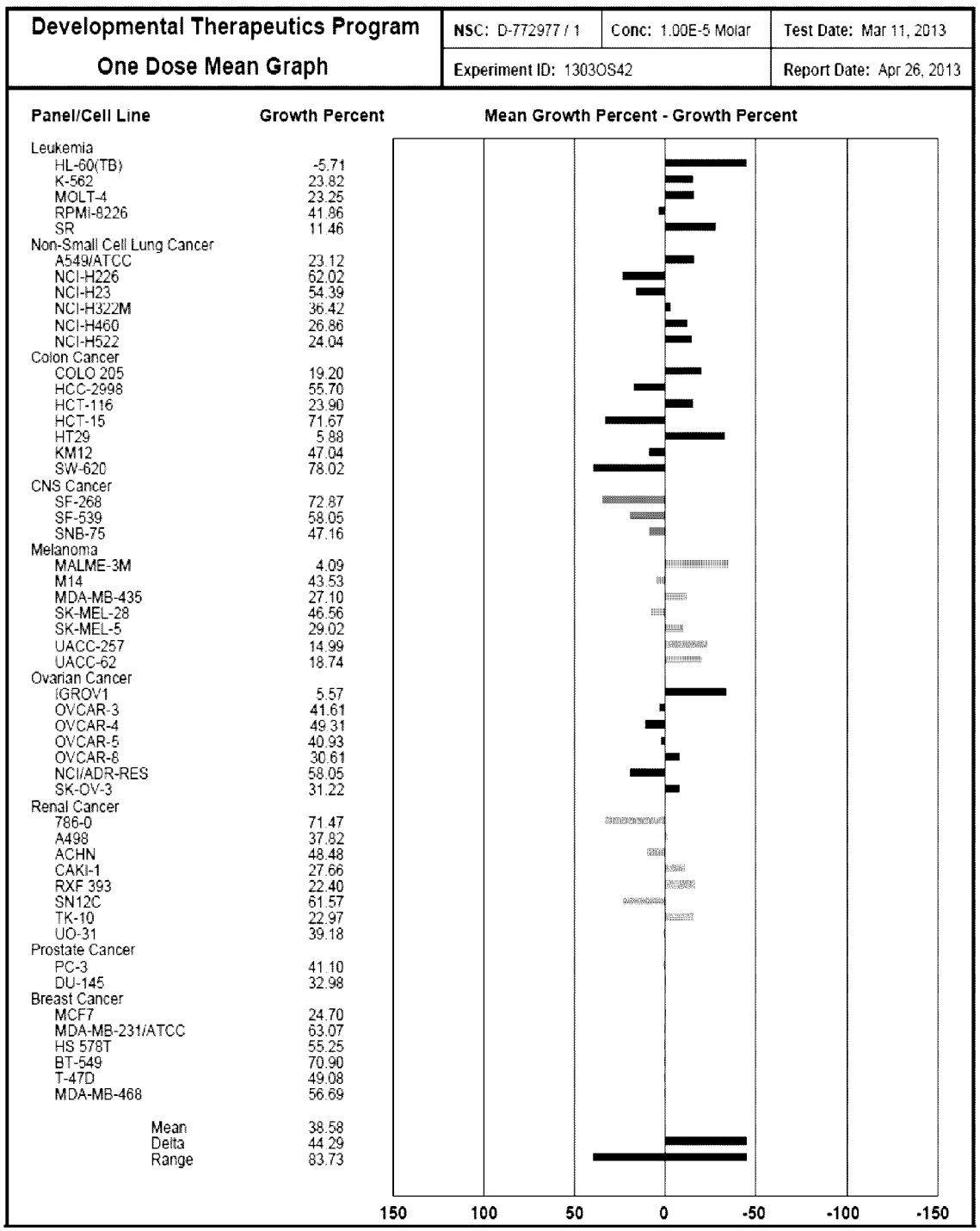
FIG. 16: Results of cell proliferation inhibition activity of JA1 at 10 μM in the NCI 60 cell line assay.
Figure 17:
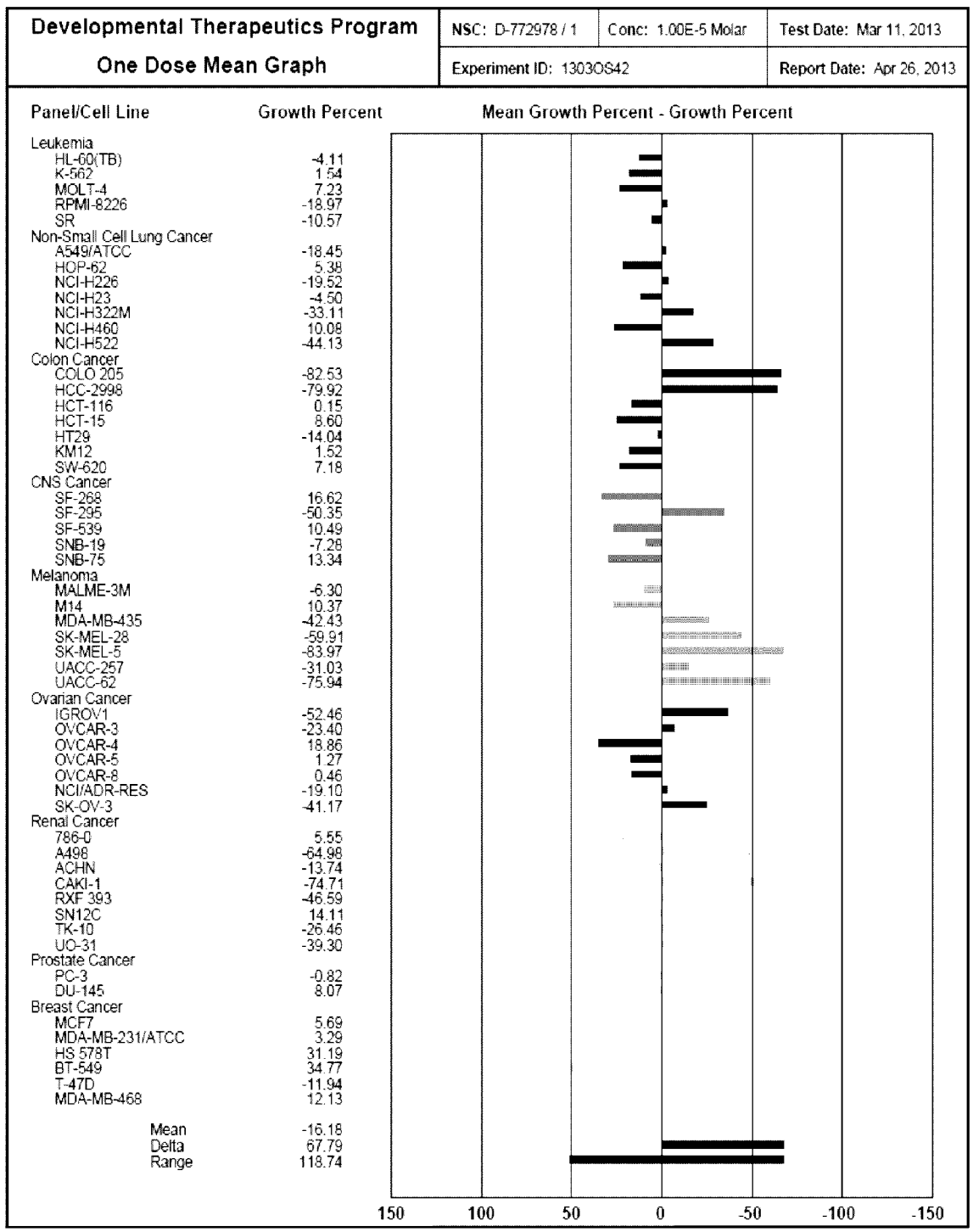
FIG. 17: Results of cell proliferation inhibition activity of JA2 at 10 μM in the NCI 60 cell line assay.
Figure 18:
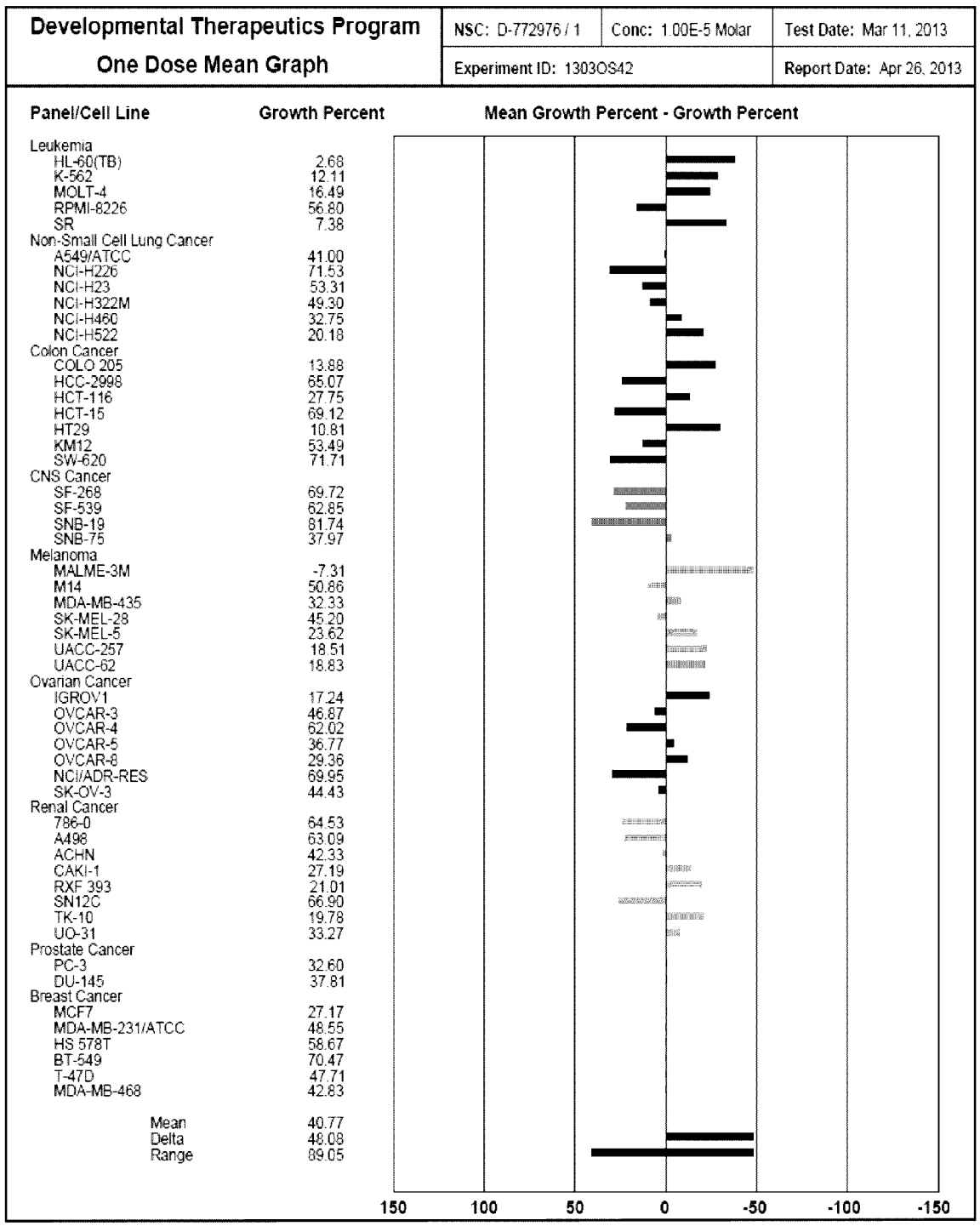
FIG. 18: Results of cell proliferation inhibition activity of JA3 at 10 μM in the NCI 60 cell line assay.
Figure 19:
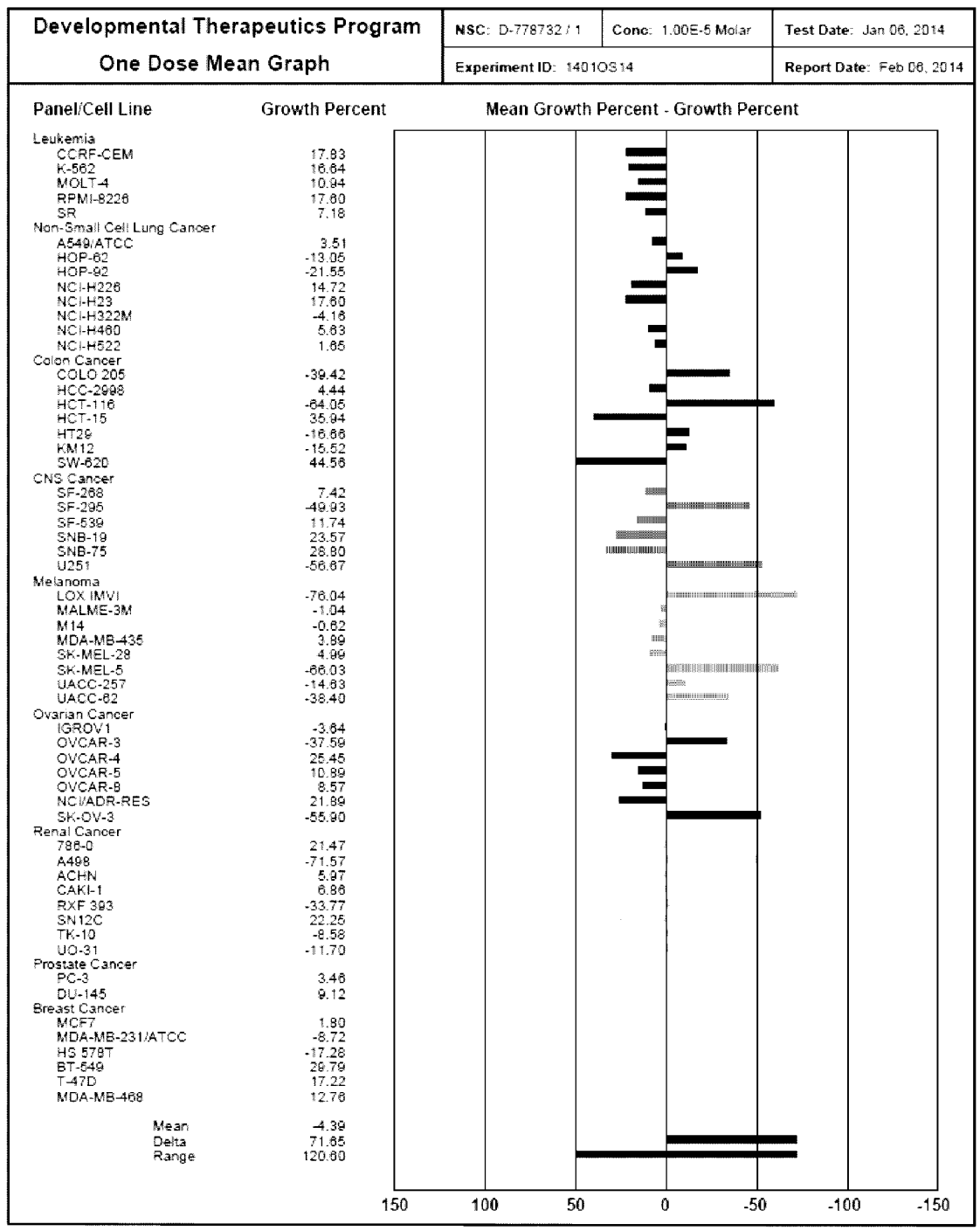
FIG. 19: Results of cell proliferation inhibition activity of JA4 at 10 μM in the NCI 60 cell line assay.
Figure 20:
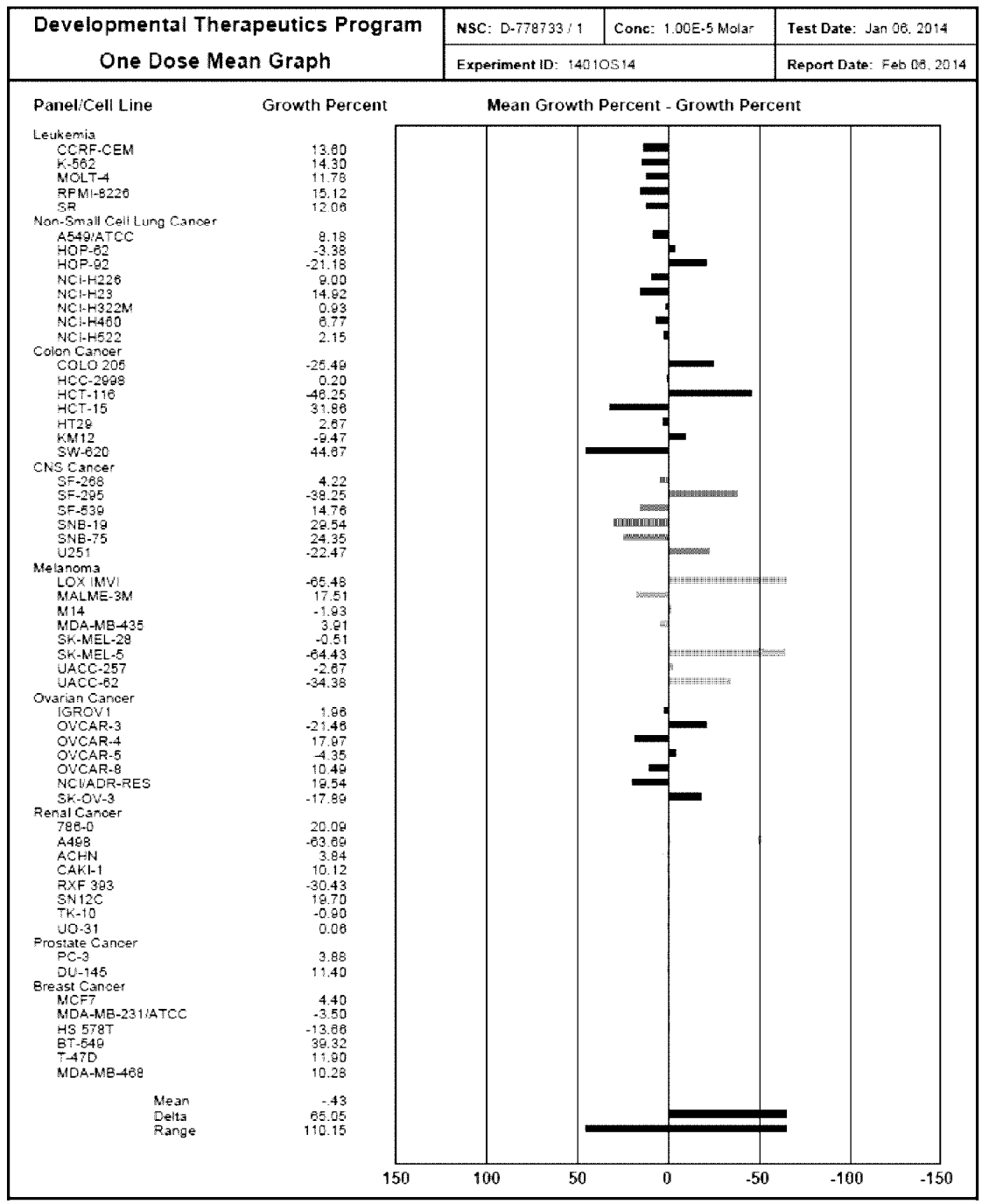
FIG. 20: Results of cell proliferation inhibition activity of JA5 at 10 μM in the NCI 60 cell line assay.
Figure 21:
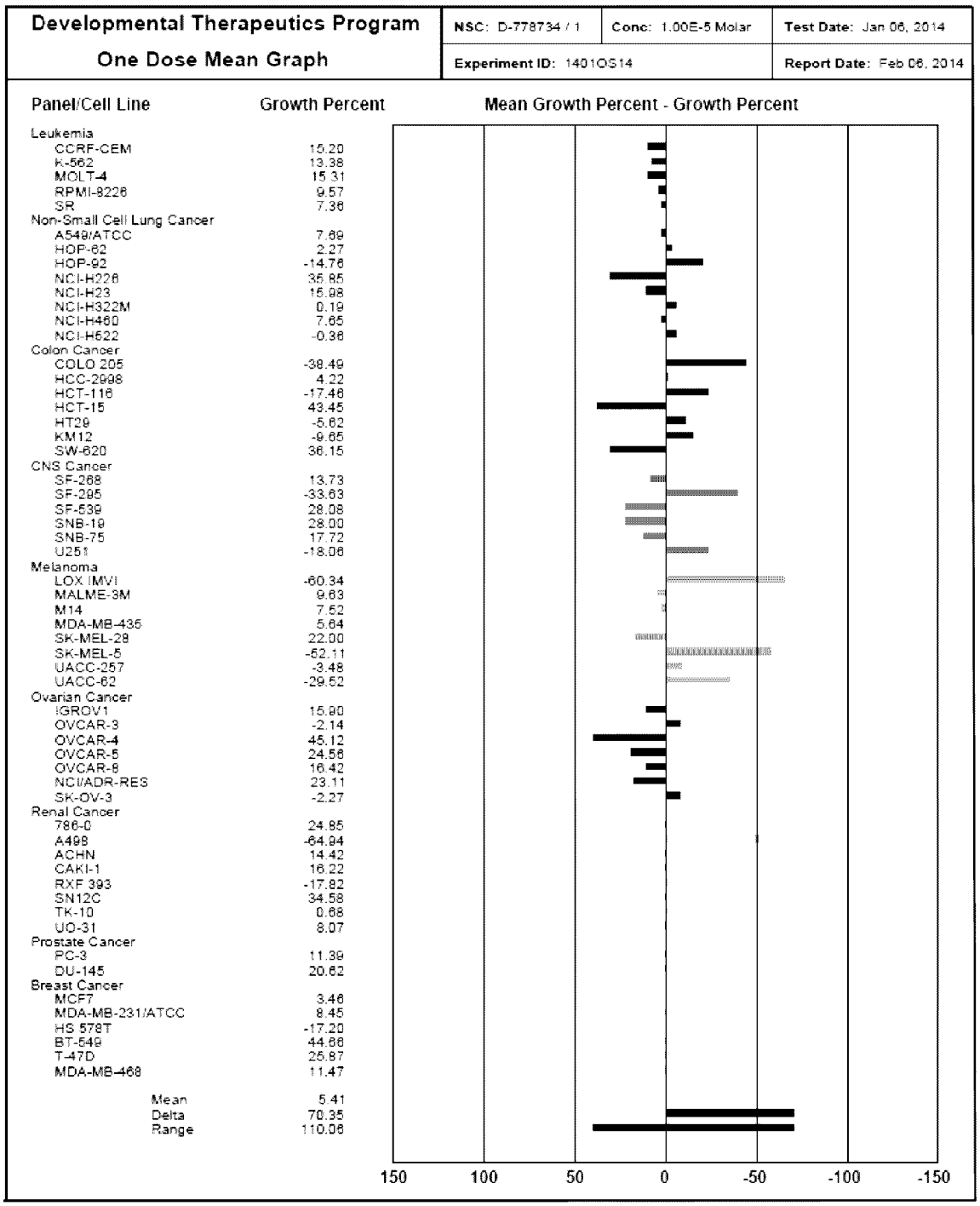
FIG. 21: Results of cell proliferation inhibition activity of JA6 at 10 μM in the NCI 60 cell line assay.

As described in the examples herein, several analogues with modified surface recognition cap groups were synthesized, using a general synthetic approach, and evaluated for their biological activity. As non-limiting examples, these analogues include compounds in which the thiazoline ring is replaced with a methylamine moiety, benzylamine, substituted benzylamine, or napthylmethyl amine group. In certain embodiments, these replacements provide for greater hydrophobic interaction with the HDAC enzyme. FIG. 4A shows the structural formulas of nine non-limiting, specific examples of such analogues. The synthesis and biological activity of many specific variants of largazole analogues with modifications in the surface recognition cap group are described, but the skilled practitioner will recognize that various other largazole analogues are within the scope of the present disclosure.

In certain embodiments, the analogues provided herein are depicted in FIG. 4A, and have the structural formula of Formula I or Formula II. Compounds of Formula I have the following structural formula:

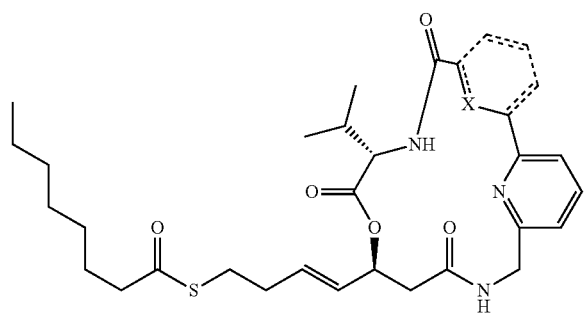

Formula I where dashed lines represent bonds that may be present or absent; X is either N or NR$_1$; and R$_1$ is selected from the group consisting of: methyl, aryl, alkaryl, hydrogen, and ether. The compound of Formula II is analogue JA1 and has the following structural formula:

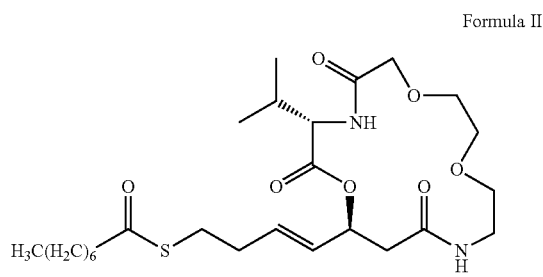

Formula II

When a compound has the structure of Formula I, the dashed lines are present, and X is N, the compound is analogue JA2. When a compound has the structure of Formula I, the dashed lines are absent, and NR$_1$ is methylamino-, the compound is analogue JA3. When a compound has the structure of Formula I, the dashed lines are absent, and NR$_1$ is benzylamino-, the compound is analogue JA4. When a compound has the structure of Formula I, the dashed lines are absent, and NR$_1$ is 4-(trifluromethyl)benzylamino-, the compound is analogue JA5. These analogues JA2-JA5 have the structural formulas denoted as Formula V, Formula VI, Formula VII, and Formula VIII, respectively.

Further included in compounds of Formula I are compounds having the structural formula of Formula IV:

Formula IV where Z is selected from the group consisting of phenyl, 4-methoxyphenyl, 4-(trifluromethane)phenyl, 4-chlorophenyl, 1-napthyl, and 4-methylphenyl. When a compound has the structural formula of Formula IV, X is N, and Z is 4-chlorophenyl, the compound is analogue AA1. When a compound has the structural formula of Formula IV, X is N, and Z is phenyl, the compound is analogue JA4. When a compound has the structural formula of Formula IV, X is N, and Z is 4-(trifluromethane)phenyl, the compound is analogue JA5. When a compound has the structural formula of Formula IV, and Z is 4-methoxyphenyl, the compound is analogue JA6. When a compound has the structural formula of Formula IV, and Z is 1-napthyl, the compound is analogue AA2. When a compound has the structural formula of Formula IV, and Z is 4-methylphenyl, the compound is analogue RF1.

Understanding how these compounds affect cellular HDAC activity is important. Therefore, the biological effects of all these analogues were evaluated. As described in the examples, the analogues JA1-JA6, AA1-AA2, and RF1 were tested in the NCI 60 cell line assay, which includes leukemia, non-small cell lung cancer, colon cancer, CNS cancer, melanoma, ovarian cancer, renal cancer, prostate cancer, and breast cancer cell lines. These analogues showed significant activity on several different cancer cell lines. Analogues JA1 and JA3 showed anti-proliferative activity equivalent to largazole at 5 µM concentration, while showing less inhibitory activity at lower concentrations. Analogue JA2 is the most potent analogue, with higher anti-proliferative activity compared to largazole at concentrations greater than 0.1 µM.

Methods of Making

Analogues JA2-JA6, AA1-AA2, and RF1

Scheme 1 (FIG. 5) shows a non-limiting example of a convergent synthetic approach usable for the synthesis of largazole analogues. The retrosynthetic analysis consists of acyl transfer from fragment 8 to amines 9, followed by Yamaguchi esterification with Fmoc-valine Macrolactamization followed by thio-esterification gives the target largazole analogues. The synthesis of the amine moieties 9 is described in more detail for each specific analogue.

Synthesis of Alcohol 8

The aldehyde 11 was prepared by an improved and more convenient procedure compared to previously reported methods. Aldehyde 14 was obtained by Michael addition of triphenylmethanethiol to acrolein using a previously developed procedure. Aldehyde 14 was reacted with (cyanomethyl)triphenylphosphorane in benzene under reflux at 90° C. to obtain the nitrile 15 (5:1, E:Z) (Scheme 2, FIG. 6). The nitrile mixture was reduced with DIBAL-H to obtain an E/Z mixture of the corresponding aldehyde 11, which was isomerized to the desired E isomer by slow passage through a silica column to obtain the E aldehyde 11 in 85% overall yield. Diastereoselective aldol reaction between the aldehyde 11 and acetyl Nagao auxillary 10, followed by flash chromatography purification of the diastereomeric mixture (6:1, S:R) on silica gel, gave the required diastereomer 8 in high yield (Scheme 2, FIG. 6). The S-configuration of the newly generated chiral center was confirmed by Mosher ester analysis.

Synthesis of Analogue JA1

The synthesis of amine 18 is shown in Scheme 3 (FIG. 7). 2-(2-Aminoethoxy)ethanol was reacted with Boc anhydride to obtain 12. Methyl bromoacetae was converted to methy iodoacete 16 by reaction with NaI and acetone (a Finkelstein reaction). The alcohol 12 was alkylated with methyl iodoacetate 16 in the presence of NaH in DMF to give the ester 17 in 78% yields. Removal of the Boc protecting group with trifluoroacetic acid/dichloromethane gave amine 18 as its TFA salt, which was used in the next step without purification.

Acyl transfer from 8 to amine 18 was carried out in the presence of DMAP to obtain alcohol 19 (Scheme 4, FIG. 8). It was esterified with Fmoc-L-valine using Yamaguchi esterification conditions to afford the acyclic precursor 20 in 96% yield. Following methyl ester hydrolysis with aqueous LiOH and Fmoc group removal with diethylamine, cyclization to the macrocyclic depsipeptide ring was achieved using HOAt, HATU, and Hunig's base to give intermediate 21 in 65% yield over the last 3 steps. After the TFA-induced removal of the trityl group, the resulting thiol was dried azeotropically with toluene and esterified with octanoyl chloride in the presence of Hunig's base and DMAP. The desired product was purified by reversed phase chromatography on $C_{18}$ in acetonitrile/water to obtain analogue JA1 in 83% yield over 2 steps.

Synthesis of Bi-pyridine Analogue JA2

Commercially available 2-bromo-6-methylpyridine was reacted with Bu—Li, followed by trimethyltin chloride to obtain the corresponding trimethyltin intermediate, which was subjected to Stille coupling with 2,6-dibromopyridine in the presence of $Pd(PPh_3)_4$ catalyst to give 6-bromo-6'-methyl-2,2'-bipyridine 22. A modified John's oxidation procedure using chromium oxide in concentrated sulfuric acid converted 22 to the carboxylic acid 23 in high yields (90%) (Scheme 5, FIG. 9). The reaction mixture was worked up with cold ice water to precipitate out the carboxylic acid. Carboxylic acid 23 was converted to the methyl ester 24 by reaction with methanol and sulfuric acid. Reaction of 24 with potassium cyanide in the presence of CuCN under microwave heating gave the corresponding nitrile 25 in high yield. Nitrile 25 was reduced to the methyl amine 26 by hydrogenation using palladium (5% Pd/C) as a catalyst.

The final stage of the synthesis of analogue JA2 is shown in Scheme 6 (FIG. 10). Acyl transfer from 8 to amine 26 in the presence of Hunig's base and DMAP gave 27. Alcohol 27 was esterified with Fmoc-L-valine under Yamaguchi esterification conditions to afford the acyclic precursor 28 in 92% yield. Following hydrolysis of the methyl ester group with lithium hydroxide and removal of the Fmoc group with diethylamine, cyclization using HOAt, HATU, and Hunig's base gave the macrocyclic depsipeptide 29 in 45% yield over the last 3 steps. Removal of the trityl group with TFA followed by thioesterification of the resulting thiol with octanoyl chloride in the presence of Hunig's base and DMAP afforded analogue JA2 in 45% yield over 2 steps. An alternative procedure for preparing JA2 is further disclosed herein.

Synthesis of Fragments 43-46

A dichloromethane suspension of 2,6-dihydroxymethyl pyridine 30, silver oxide, and potassium iodide was treated with tosyl chloride at −20° C. (Scheme 7, FIG. 11) to give predominantly the mono-tosylated product 31 with a trace amount of di-tosylated product. Mono-tosylated product 31 was separated by passing through a pad of silica gel in dicholormethane and was converted to azide 32 by heating with sodium azide in DMF. Tosylation of 32 using tosyl chloride and sodium hydroxide gave product 33 in almost quantitative yield. Nucleophilic displacement of the tosyl group with the appropriate amines was achieved by heating 33 and the respective amines 34-37 in the presence of potassium carbonate as base. The tertiary amines 38-41 were reduced with $H_2$/Pd to give amines 42-45 in almost quantitative yield.

Synthesis of Analogues JA3-JA6

The synthesis of analogues JA3-JA6 is shown in Scheme 8 (FIG. 12). Acyl transfer from 8 to the amines 42-45 was carried out in the presence of DMAP to obtain amides 46-49. The amides 46-49 were esterified with Fmoc-L-valine using Yamaguchi esterification conditions to afford acyclic precursor 50-53 in 92-96% yield. Following methyl ester hydrolysis with aqueous LiOH and Fmoc removal with diethylamine, cyclization to the macrocyclic depsipeptide ring was achieved using HOAt, HATU, and Hunig's base to give products 54-57. After removal of trityl group with TFA, the resulting thiol was dried azeotropically with toluene and esterified with octanoyl chloride in the presence of Hunig's base and DMAP. The desired products were purified by reversed phase chromatography on $C_{18}$ in acetonitrile/water to obtain analogues JA3-JA6 in 65-83% yield over 2 steps.

Synthesis of Analogues AA1-AA2

The synthesis of analogues AA1-AA2 and RF1 is shown in Schemes 9 and 10 (FIG. 13 and FIG. 14, respectively). Esterification of bromoacetic acid with 2-trimetylsilylethyl alcohol, followed by the reaction of the resulting ester with substituted benzyl amines 58 and 60 and 1-(aminomethyl)-naphthalene 59 gave the corresponding nucleophilic substitution products 61-63. The products 61-63 were reacted with tosylate 33 to obtain the tertiary amines 64-66. The azide group was reduced by catalytic hydrogenation to obtain the primary amines 67-69.

Acyl transfer from 8 to amines 67-69 gave the intermediates 70-72, which were subjected to Yamaguchi esterification with Fmoc-valine to obtain acyclic intermediates 73-75 (Scheme 10, FIG. 14). Both Fmoc and trimethylsilylethyl protecting groups were removed simultaneously with TBAF, and the product was obtained in a high degree of purity by partitioning between water and ethyl acetate, removing ethyl acete under reduced pressure, and washing the residue with hexane. It was used in the next step without further purification.

Alternative Procedure for Synthesizing Analogue JA2

The cyclic intermediate 29 in the synthesis of compound JA2 was resynthesized in improved yields using a modified protocol as shown in Scheme 11 (FIG. 15). Hydrolysis of the methyl ester group of 25 gave the carboxylic acid 82, which was converted to the trimethylsilylethyl ester 83. Reduction of the azide group of 83 gave the amine 84, which was subjected to acyl transfer with 8 to obtain the amide 85. Yamaguchi esterification of 85 with Fmoc-valine gave the acyclic precursor 86. Removal of trimethylsilylethyl and Fmoc protecting groups with TBAF followed by cyclization with HATU and HOAt as before gave the cyclic intermediate 29. It was converted to JA2 as described before.

Pharmaceutical Compositions

Pharmaceutical compositions of the present disclosure comprise an effective amount of a largazole analogue compound disclosed herein, and/or additional agents, dissolved or dispersed in a pharmaceutically acceptable carrier. The phrases "pharmaceutical" or "pharmacologically acceptable" refer to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543, 158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

In particular embodiments, the compounds and compositions described herein are useful for treating various cancers such as, but not limited to: leukemia, non-small cell lung cancer, colon cancer, CNS cancer, melanoma, ovarian cancer, renal cancer, prostate cancer, and breast cancer. Furthermore, the compounds and compositions herein can be used in combination therapies. That is, the compounds and compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

By way of a non-limiting example of a combination therapy, the largazole analogue compounds or compositions can be administered in combination with one or more suitable anti-cancer agents including, but not limited to: chemotherapeutic agents; cytotoxins; antimetabolites; alkylating agents; protein kinase inhibitors; anthracyclines; antibiotics; miRNAs; anti-miRNAs; antimitotic agents (e.g. antitubulin agents); corticosteroids; radiopharmaceuticals; proteins such as cytokines, enzymes, or interferons; biological response modifiers such as krestin, lentinan, sizofiran, picibanil, ubenimex; anti-angiogenic compounds such as acitretin, fenretinide, thalidomide, zoledronic acid, angiostatin, aplidine, cilengtide, combretastatin A-4, endostatin, halofuginone, rebimastat, Removab®, Revlimid®, squalamine, ukrain, or Vitaxin®; platinum-coordinated compounds such as cisplatin, carboplatin, nedaplatin, or oxaliplatin; camptothecin derivatives such as camptothecin, 10-hydroxycamptothecin, 9-aminocamptothecin, irinotecan, SN-38, edotecarin, or topotecan; compounds or chelates that include radionuclides; or combinations thereof. Examples of suitable interferons include, but are not limited to interferon alpha, interferon alpha-2a, interferon, alpha-2b, interferon beta, interferon gamma-1a, interferon gamma-1b (Actimmune), interferon gamma-n1, or combinations thereof.

In certain embodiments, the anti-cancer agent is one or more of hydroxyureas, Taxol®, adriamycin, 5-fluorouracil, cyclophosphamide, etoposide, altretamine, ifosfamide, vinblastine sulfate, estramustine phosphate, suramin, strontium-89, filgrastim, lentinan, sizofilan, TheraCys®, ubenimex, WF-10, aldesleukin, alemtuzumab, BAM-002, dacarbazine, daclizumab, denileukin, gemtuzumab ozogamicin, ibritumomab, imiquimod, lenograstim, lentinan, Corixa, molgramostim, OncoVAX-CL, sargramostim, tasonermin, tecleukin, thymalasin, tositumomab, Virulizin®, Z-100, epratuzumab, mitumomab, oregovomab, pemtumomab (Y-muHMFGI), Provenge® (Dendreon), alitretinoin, ampligen, atrasentan bexarotene, bortezomib, bosentan, calcitriol, exisulind, finasteride, fotemustine, ibandronic acid, miltefosine, mitoxantrone, l-asparaginase, procarbazine, dacarbazine, hydroxycarbamide, pegaspargase, pentostatin, tazarotne, Telcyta® (TLK-286, Telik Inc.), Velcade® (bortemazib, Millenium), or tretinoinor.

Another non-limiting example of a combination therapy for cancers or other diseases is the combination of an largazole analogue compounds or largazole analogue-containing composition with one or more surgical treatments. Suitable surgical treatments include, but are not limited to, a polypectomy, a colectomy, a transanal resection, a wedge resection, a lobectomy, a pneumonectomy, a sleeve reduction, a hysterectomy, a bilaterial salpingo-oophorectomy, an omentectomy, or a nephrectomy. Other possible therapies suitable for combination with a largazole analogue compound or largazole analogue-containing composition include, but are not limited to, immunotherapy, hormone therapy, radiation therapy, or a combination thereof.

Embodiments of the present disclosure further include methods of determining coverage or denial of health insurance reimbursement and/or payment for treatments of disease comprising the compounds or compositions described herein. In certain embodiments, the treatment comprises a largazole analogue compound or largazole analogue-containing pharmaceutical composition, and a provider of health insurance denies coverage or reimbursement for the treatment.

Kits

It is envisioned that the compounds, compositions, and methods described herein could be embodied as parts of a kit or kits. A non-limiting example of such a kit is a kit for making a largazole analogue, the kit comprising an alcohol fragment and an amine in separate containers, where the containers may or may not be present in a combined configuration. Many other kits are possible, such as kits further comprising one or more reagents selected from DMAP, Hunig's base, Fmoc-valine, TFA, and TIPS, or kits further comprising a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example 1

Synthesis of Analogues JA1-JA6, AA1-AA2, and RF1

Synthesis of 3-(tritylthio)propanal (14)

To a solution of triphenylmethanethiol (1.38 g, 5 mmol, 1 equiv) in dichloromethane (20 mL) was added acrolein (0.393 g, 7 mmol, 1.4 equiv) and triethylamine (0.71 g, 7 mmol, 1.4 equiv). The reaction mixture was stirred for 1 h at room temperature and was concentrated under reduced pressure to give aldehyde 14 as an off-white solid (1.66 g, 99%). mp 98-99° C. $^1$H NMR (600 MHz, CDCl$_3$) δ 2.35-2.39 (t, J=7.3 Hz, 2H), 2.45-2.49 (t, J=6.6 Hz, 2H), 7.21-7.24 (t, J=7.3 Hz, 3H), 7.28-7.32 (t, J=8.0 Hz, 5H), 7.42-7.44 (d, J=7.6 Hz, 7H), 9.56 (s, 1H). $^{13}$C NMR (150 MHz, CDCl$_3$):

δ 24.6, 42.9, 127.0, 128.2, 129.8, 144.7, 200.6 ppm. It was used in the next step without purification.

Synthesis of (E)-5-(tritylthio)pent-2-enenitrile (15)

To a suspension of (cyanomtheyl)triphenylphsphonium chloride (5.06 g, 15 mmol, 1.5 equiv) in dry dichloromethane (50 mL) was added triethylamine (3.80 g, 38 mmol, 3.9 equiv). The reaction mixture was stirred at room temperature for 45 min and the solvent was removed under reduced pressure to give (cyanomethylene)triphenylphsphorane as a yellow solid, which was used in the next step without further purification.

A mixture of aldehyde 14 (3.33 g, 10 mmol, 1 equiv) and the (cyanomethylene)triphenylphsphorane obtained above in dry benzene (50 mL) was heated under reflux for 3 h. The reaction mixture was concentrated under reduced pressure and purified by passing through a silica pad in 50% dichloromethane/hexanes to 35, which afforded a cis: trans (1:3) mixture of nitrile 15 (3.2 g, 90%) as a white solid, mp 124-126° C. The product 15 was used in the next step without further purification.

Synthesis of (E)-5-(tritylthio)pent-2-enal (11)

To a solution of nitrile 15 (355 mg, 1 mmol, 1 equiv) in toluene (5 mL) at −78° C. was added DIBAL-H (1.33 mL of 1.2 M solution in hexanes, 1.5 mmol, 1.5 equiv). The reaction mixture was stirred for 3 h at −78° C. and allowed to warm to room temperature. Water (10 mL) was added and the mixture was stirred for 15 min. It was extracted with ether (3×20 mL), washed with brine, and dried over anhydrous sodium sulfate. The solvent was removed under reduced pressure and the crude product was purified by passing through a pad of silica gel in dichloromethane to afford aldehyde 11 as white crystals (322 mg, 90%). mp 144-148° C. $^1$H NMR (600 MHz, CDCl$_3$) δ 2.27-2.31 (m, 2H), 2.34-2.36 (t, J=6.9 Hz, 2H), 5.96-6.00 (q, J=7.8 Hz, 1H), 6.60-6.64 (dt, J=15.7, 6.5 Hz, 1H), 7.21-7.25 (t, J=7.4, Hz, 3H), 7.28-7.30 (t, J=7.8 Hz, 6H), 7.42-7.43 (d, J=8.0 Hz, 6H). $^{13}$C NMR (100 MHz, CDCl$_3$): δ 30.24, 31.96, 67.22, 127.03, 128.23, 129.76, 133.85, 144.79, 156.09, 149.03 ppm.

Synthesis of (S,E)-3-hydroxy-1-((R)-4-isopropyl-2-thioxothiazolidin-3-yl)-7-(tritylthio)hept-4-en-1-one (8)

To a stirred solution of acetyl Nagao auxiliary 10 (1.493 g, 7.355 mmol, 1 equiv) in dichloromethane (60 mL) at 0° C., was added TiCl$_4$ (1.72 g, 9.05 mmol, 1.23 equiv). After stirring for 5 minutes at 0° C., the reaction mixture was cooled to −78° C. and Hunig's base (1.872 g, 9.02 mmol, 1.25 equiv) was added. The reaction mixture was stirred for 2 h at −78° C. and the aldehyde 11 (2.6 g, 7.26 mmol, 0.987 equiv) in dichloromethane (8 mL) was added dropwise. The reaction mixture was stirred for 1 h at −78° C., treated with water (15 mL), and diluted with dichloromethane (50 mL). The layers were separated and the aqueous layer was extracted with dichloromethane. The combined organic extract was washed with saturated NaCl (40 mL) and dried over anhydrous sodium sulfate. The solvent was removed in vacuo and the residue was purified by flash chromatography on silica gel in dichloromethane/hexanes (25-90%) to give the major isomer 8 as a yellow oil (3.5 g, 86%). $[\alpha]_D^{20}$ −138.0 (c 1.0, CHCl$_3$). $^1$H NMR (600 MHz, CDCl$_3$) δ 0.97-0.99 (d, J=6.9 Hz, 1H), 1.05-1.07 (d, J=7.0 Hz, 1H), 2.06-2.13 (m, 2H), 2.21-2.25 (t, J=7.0 Hz, 2H), 2.32-2.40 (m, 1H), 2.88 (brs, 1H), 2.962-0.99 (d. J=11.7 Hz, 1H), 3.27-3.33 (dd, J=17.6, 8.7 Hz, 1H), 3.43-3.48 (dd, J=11.3, 8.0 Hz, 1H), 3.55-3.60 (dd, J=17.5, 2.5 Hz, 1H), 4.57-4.58 (m, 1H), 5.11-5.15 (t, J=7.0 Hz, 1H), 5.45-5.50 (dd, J=15.4, 5.9 Hz, 1H), 5.57-5.64 (m, 1H), 7.207.23 (t, J=7.3 Hz, 3H), 7.27-7.31 (t, J=8.0 Hz, 5H), 7.42-7.44 (d, J=7.6 Hz, 7H). $^{13}$C NMR (150 MHz, CDCl$_3$): δ 18.1, 19.4, 30.9, 31.1, 31.7, 31.7, 45.6, 66.8, 68.7, 71.7, 126.9, 128.1, 129.8, 130.2, 132.2, 145.1, 172.7, 203.2 ppm.

Synthesis of 3,6,11-trioxa-9-azatridecanoic acid, 12,12-dimethyl-10-oxo-, methyl ester (17)

To a stirred solution of 2-(2-aminoethoxy)ethanol (1.05 g, 10 mmol, 1 equiv) in anhydrous ethanol (15 mL) at 0° C. was added di-tert-butyl dicarbonate (2.2 g, 10 mmol, 1 equiv). The reaction mixture was stirred for 2 hours at room temperature. It was concentrated under reduced pressure, re-dissolved in dichloromethane, and washed with brine. The organic extract was dried over anhydrous sodium sulfate and the solvent was removed under reduced pressure to give the crude product as a colorless oil. The product 12 was used in the next step without further purification. $^1$H NMR (600 MHz, CDCl$_3$) δ 1.44 (s, 9H), 3.33-3.34 (m, 2H), 3.54-3.59 (dt, J=10.4, 5.2 Hz, 2H), 3.73-3.75 (dt, J=4.3, 3.4 Hz, 2H).

A mixture of methyl bromoacetate (2.0 g, 1.24 mL, 13.1 mmol, 1 equiv) and sodium iodide (2.51 g, 16.7 mmol, 1.28 equiv) in acetone (9 mL) was stirred at room temperature for 3 h. The reaction mixture was filtered and the white solid was washed with ether (3×5 mL). The organic extract was concentrated under reduced pressure. The residue was re-dissolved in dichloromethane, washed with brine, dried over anhydrous sodium sulfate and solvent removed under reduced pressure to give methyl iodoacetate 16 as an orange yellow oil (2.2 g, 85%).

To a stirred solution of 2-[2-(boc-amino)ethoxy]ethanol 12 (0.20 g, 1 mmol, 1 equiv) in anhydrous dimethylformamide (4 mL) at 0° C. was added sodium hydride (66 mg, of 60% dispersion in oil, 1.5 equiv). The reaction mixture was stirred for 1 h at 0° C., and iodomethyl acetate 16 (480 mg, 2.4 mmol, 2.4 equiv) was added. The reaction mixture was stirred overnight at room temperature. After adding water, the reaction mixture was extracted with dichloromethane (2×10 mL). The combined organic extract was washed with water (2×10 mL), dried over anhydrous sodium sulfate, and the solvent evaporated under reduced pressure. The residue was purified by flash chromatography on silica gel in ethyl acetate/hexanes (5-10%) to give 17 as a yellow oil (215 mg, 78%). $^1$H NMR (600 MHz, CDCl$_3$) δ 1.44 (s, 9H), 3.31-3.32 (m, 2H), 3.53-3.56 (t, J=5.1 Hz, 2H), 3.64-3.66 (m, 2H), 3.71-3.73 (m, 2H), 3.76 (s, 3H), 4.16 (s, 2H). $^{13}$C NMR (CDCl$_3$, 150 MHz): δ 28.7, 40.58, 52.11, 68.82, 70.52, 70.58, 71.15, 156.20, 171.05 ppm. HRMS: (ESI) calcd for C$_{12}$H$_{23}$NO$_6$ [M+Na]$^+$ 300.1423. found, 300.1417.

Synthesis of (S,E)-methyl 2-(2-(2-(3-hydroxy-7-(tritylthio)oct-4-enamido)ethoxy)ethoxy)acetate (19)

A solution of compound 17 (140 mg, 0.5 mmol, 1 equiv) in TFA/DCM (1:2) (7 mL) was stirred at room temperature for 2 h. The reaction mixture was concentrated under reduced pressure and the residue was dried azeotropically with toluene. To a solution of the product in dichloromethane (5 mL) was added DMAP (62 mg, 0.5 mmol, 1 equiv), and Hunig's base (130 mg, 1 mmol, 2 equiv). The reaction mixture was stirred at room temperature for 30 min, followed by addition of a solution of the aldol product 8 (280 mg, 0.5 mmol, 1 equiv) in dichloromethane (5 mL). It was stirred at room temperature overnight, concentrated in vacuo, and purified by flash chromatography on silica gel in ethyl acetate/hexanes (80-100%) to get 19 as a yellow oil (260 mg, 93%). $[\alpha]_D^{22}$ −6.8 (c 1.0, CHCl$_3$). $^1$H NMR (600 MHz, CDCl$_3$) δ 2.03-2.09 (m, 2H), 2.17-2.21 (t, J=7.3 Hz, 1H), 2.28-2.34 (m, 1H), 2.37-2.42 (m, 1H), 3.41-3.45 (m, 2H), 3.54-3.56 (t, J=5.0 Hz, 1H), 3.63-3.71 (m, 4H), 3.70 (s, 1H), 4.01-4.02 (d, J=3.3 Hz, 2H), 4.13 (s, 1H), 4.38-4.41 (m, 1H), 5.38-5.43 (dd, J=15.3, 5.8 Hz, 1H), 5.51-5.58 (m, 1H), 6.70-6.73 (t, J=5.2 Hz, 1H), 7.18-7.21 (t, J=7.3 Hz, 3H), 7.25-7.29 (t, J=8.0 Hz, 5H), 7.38-7.40 (d, J=7.6 Hz, 7H). $^{13}$C NMR (150 MHz, CDCl$_3$): δ 31.6, 31.7, 39.3, 42.6, 52.2, 66.8, 68.6, 69.4, 69.9, 70.3, 71.3, 126.8, 128.1, 129.8, 132.8, 145.1, 171.3, 172.3 ppm. HRMS: (ESI) calcd for C$_{33}$H$_{39}$NO$_6$S [M+Na]$^+$ 600.2396. found 600.2389.

Synthesis of (R)—((S,E)-3,12-dioxo-2,5,8-trioxa-11-azaocta-7-(tritylthio)dec-15-en-14-yl) 2-(((9H-fluoren-9-yl)methoxy)carbonylamino)-3-methylbutanoate (20)

To a solution of Fmoc-L-valine (117 mg, 0.346 mmol, 2 equiv) in THF (1 mL) at 0° C. was added Hunig's base (67 mg, 0.519 mmol, 3 equiv) and 2,4,6-tricholorobenzoyl chloride (89 mg, 0.363 mmol, 2.1 equiv). The reaction mixture was stirred for 1 h at 0° C. When TLC showed the formation of anhydride (100 mg, 0.173 mmol, 1 equiv), alcohol 19 and DMAP (22 mg, 0.173 mmol, 1 equiv) in THF (2 mL) were added to the reaction mixture at 0° C. The reaction mixture was stirred at room temperature overnight, concentrated in vacuo, and purified by flash chromatography on silica gel in ethyl acetate/hexanes (50-70%). The product was subjected to a second purification by reversed phase chromatography on C$_{18}$ in acetonitrile/water (40-100%) to get 20 as a yellow oil (150 mg, 96%). $[\alpha]_D^{22}$ −12.5 (c 0.7, CHCl$_3$). $^1$H NMR (600 MHz, CDCl$_3$) δ 0.81-0.82 (d, J=6.6 Hz, 3H), 0.90-0.91 (d, J=6.8 Hz, 3H), 2.03-2.06 (m, 2H), 2.10-2.18 (m, 3H), 2.45-2.49 (m, 1H), 252.-2.55 (m, 1H), 3.33-3.42 (m, 2H), 3.46-3.51 (m, 2H), 3.57-3.58 (m, 2H), 3.62-3.63 (m, 2H), 3.69 (s, 3H), 4.09 (s, 2H), 4.2-4.23 (m, 2H). 436.-4.41 (m, 2H), 5.37-5.41 (dd, J=15.7, 7.5 Hz, 1H), 5.45-5.47 (d, J=6.3 Hz, 1H), 5.62-5.68 (m, 2H), 6.41 (brs, 1H), 7.18-7.20 (t, J=7.1 Hz, 3H), 7.25-7.28 (t, J=7.8 Hz, 6H), 7.29-7.31 (t, J=7.3 Hz, 2H), 7.38-7.39 (d, J=7.8 Hz, 8H), 7.59-7.60 (d, J=7.3 Hz, 2H), 7.74-7.76 (d, J=7.3 Hz, 2H). $^{13}$C NMR (150 MHz, CDCl$_3$): δ 17.7, 19.3, 31.4, 31.6, 39.4, 41.8, 47.4, 52.1, 59.9, 66.8, 67.1, 68.6, 69.9, 70.2, 71.2, 72.8, 120.2, 120.2, 125.3, 125.3, 126.7, 127.3, 127.4, 128.0, 128.1, 128.2, 129.8, 133.9, 141.5, 141.5, 144.0, 144.1, 145.1, 156.5, 169.1, 171.1 ppm. HRMS: (ESI) calcd for C$_{53}$H$_{58}$N$_2$O2S [M+Na]$^+$ 921.3761. found 921.3752.

Synthesis of (3R,16S)-3-isopropyl-16-((E)-4-(tritylthio)but-1-enyl)-1,7,10-trioxa-4,13-diazacyclohexadecane-2,5,14-trione (21)

To a solution of 20 (35 mg, 0.040 mmol, 1 equiv) in THF/H$_2$O (4:1, 2 mL) at 0° C. was added 0.1M LiOH (0.4 mL, 0.04 mmol, 1.0 equiv) dropwise over a period of 10 minutes. The reaction mixture was stirred at 0° C. for another 1 h, treated with 1M HCl solution and extracted with ethyl acetate (3×2 mL). The organic extract was washed with brine, dried over anhydrous sodium sulfate and solvent evaporated under reduced pressure to give the crude carboxylic acid, which was used in the next step without further purification.

To a solution of crude carboxylic acid in dichloromethane (5 mL) was added diethylamine (0.3 g, 3.9 mmol, 96 equiv). After stirring the reaction mixture at room temperature for 4 h, it was concentrated under reduced pressure and dried for 12 h in high vacuum to give the crude amine product. The crude product was used in the next step without additional purification.

A solution of the crude amine above, HATU (0.030 g, 0.08 mmol, 2.0 equiv), HOAt (11 mg, 0.08 mmol, 2.0 equiv), and Hunig's base (0.025 g, 0.187 mmol, 4.4 equiv) in dichloromethane (45 mL) was stirred for 3 days at room temperature. The reaction mixture was concentrated in vacuo, diluted with dichloromethane (5 mL), washed with brine, and solvent evaporated under reduced pressure. The residue was purified by flash chromatography on silica gel in ethyl acetate followed by recrystallization from dichloromethane/hexanes to give 21 as a white solid (17 mg, 65%). mp 183-188° C. $[\alpha]_D^{20}$ −2.34 (c 0.12, CHCl$_3$). $^1$H NMR (600 MHz, CDCl$_3$) δ 0.89-0.91 (d, J=6.9 Hz, 3H), 0.95-0.96 (d, J=6.9 Hz, 3H), 2.04-2.11 (m, 2H), 2.20-2.23 (t, J=4.6 Hz, 2H), 2.32-2.37 (m, 1H), 2.48-2.52 (dd, J=14.6, 9.1 Hz, 1H), 2.56-2.59 (dd, J=14.6, 9.0 Hz, 1H), 3.31-3.35 (m, 1H), 3.48-3.56 (m, 2H), 3.61-3.70 (m, 3H), 3.72-3.76 (m, 2H), 3.96-3.98 (d, J=15.7 Hz, 1H), 4.16-4.18 (d, J=16.3 Hz, 1H), 4.80-4.83 (dd, J=10.1, 4.3 Hz, 1H), 5.33-5.37 (m, 1H), 5.52-5.55 (m, 1H), 5.62-5.67 (m, 1H), 6.08-6.09 (m, 1H), 7.22-7.25 (tt, J=16.6, 1.1 Hz, 3H), 7.29-7.34 (m, 6H), 7.41-7.43 (m, 6H). $^{13}$C NMR (150 MHz, CDCl$_3$): δ 17.2, 19.2, 19.2, 31.1, 31.4, 31.9, 38.9, 41.9, 56.6, 66.7, 68.8, 69.2, 70.0, 71.3, 71.6, 126.7, 127.7, 127.9, 129.6, 133.1, 144.8, 169.3, 169.3, 169.7 ppm. HRMS: (ESI) calcd for C$_{37}$H$_{44}$N$_2$O$_6$S [M+Na]$^+$ 667.2818. found 667.2802.

Synthesis of Analogue JA1

To a solution of cyclized compound 21 (40 mg, 0.076 mmol, 1 equiv) and triisopropylsilane (18 mg, 0.114 mmol, 1.5 equiv) in dichloromethane (3 mL) at 0° C. was added trifluoroacetic acid (0.26 g, 2.28 mmol, 30 equiv). The reaction mixture was stirred for 4 h at room temperature. It was concentrated in vacuo and the residue was dried azeotropically with toluene, and used in the next step without additional purification.

To a stirred solution of the above crude thiol (0.076 mmol, 1 equiv) and catalytic DMAP (3.0 mg) in dichloromethane (4 mL) at 0° C. were added Hunig's base (30 mg, 0.228 mmol, 3 equiv) and octanoyl chloride (31 mg, 0.19 mmol, 2.5 equiv). The reaction mixture was stirred at room temperature overnight. It was concentrated in vacuo and purified by flash chromatography on silica gel in 20-50% acetone/hexanes to give product JA1 as a colorless oil (33 mg, 83%). $[\alpha]_D^{22}$ +13.6 (c 0.06, CHCl$_3$). $^1$H NMR (600 MHz, CDCl$_3$) δ 0.88-0.92 (dd, J=14.0, 7.4 Hz, 5H), 0.96-0.097 (d, J=6.9 Hz, 3H), 1.28-1.32 (m, 8H), 1.64-1.68 (quin, J=7.4 Hz, 2H), 1.75 (brs, 1H), 2.29-2.32 (q, 7.4 Hz, 2H), 2.32-2.38 (m, 1H), 2.52-2.60 (m, 4H), 2.90-2.92 (t, J=7.3 Hz, 2H), 3.32-3.38 (m, 1H), 3.53-3.57 (m, 2H), 3.66-3.68 (m, 1H), 3.71-3.80 (m, 4H), 3.97-4.00 (d, J=16.5 Hz, 1H), 4.21-4.24 (d, J=17.0 Hz, 1H), 4.82-4.85 (dd, J=10.3, 4.4 Hz, 1H), 5.48-5.52 (dd, J=15.4, 6.6 Hz, 1H), 5.57-5.60 (m, 1H), 5.76-5.81 (dt, J=15.5, 6.6 Hz, 1H), 6.13 (m, 1H), 7.33-7.35 (d, J=10.3 Hz, 1H). $^{13}$C NMR (150 MHz, CDCl$_3$): δ 14.1, 17.2, 19.2, 22.6, 25.7, 27.8, 28.9, 31.6, 31.9, 32.2, 39.0, 42.1, 44.2, 56.6, 68.8, 69.2, 70.0, 71.26, 72.8, 128.7, 132.7, 169.3, 169.4, 169.7, 199.4 ppm. HRMS: (ESI) calcd for $C_{26}H_{44}N_2O_7S$ [M+Na]$^+$ 551.2767. found 551.2785, Anal. ($C_{26}H_{44}N_2O_7S$—0.3; $H_2O$) C, H, N.

Synthesis of 6-bromo-6'-methyl-2,2'-bipyridine (22)

To a stirred solution of 2-bromo-6-methylpyridine (1.25 g, 7.3 mmol, 1 equiv) in dry ether (40 mL) at −78° C. was added n-butyllithium (4.6 mL, 1.6 M solution in hexanes, 7.3 mmol, 1 equiv) dropwise over a period of 10 min under nitrogen. The reaction mixture was stirred at −78° C. for 1 h, followed by dropwise addition of a solution of trimethyltin chloride (1.5 g, 7.5 mmol) solution in dry THF (8 mL). The reaction mixture was stirred for 3 h at room temperature, filtered through a pad of celite, and concentrated in vacuo to give the tin derivative as a yellow oil. The crude reaction product was used in the next step without additional purification.

To a mixture of 2,6-dibromopyridine (1.73 g, 7.3 mmol), LiCl (1.15 g, 14.6 mmol), and Pd(PPh$_3$)$_4$ (0.22 g, 0.2 mmol) was added a solution of tin derivative prepared above (2.3 g, 7.3 mmol) in toluene (5 mL) under nitrogen atmosphere. The reaction mixture was heated under reflux at 120° C. for 24 h, solvent was evaporated in vacuo, and the residue purified by flash chromatography on silica gel in dichloromethane/hexanes (50-100%) to get 22 as a yellow powder (1.10 g, 60%). mp 138-143° C. $^1$H NMR (600 MHz, CDCl$_3$) δ 4.04 (s, 3H), 7.52-7.54 (d, J=7.9 Hz, 1H), 7.69-7.72 (t, J=7.9 Hz, 1H), 7.96-7.99 (t, J=7.9 Hz, 1H), 8.15-8.16 (d, J=7.0 Hz, 1H), 8.52-8.53 (d, J=7.7 Hz, 1H), 8.60-8.61 (d, J=7.9 Hz, 1H). $^{13}$C NMR (150 MHz, CDCl$_3$): δ 53.0, 120.4, 124.7, 125.6, 128.6, 138.1, 139.4, 141.6, 147.6, 154.8, 156.3, 165.7 ppm.

Synthesis of 6'-bromo-2,2'-bipyridine-6-carboxylic acid (23)

A powder of 6-bromo-6'-methyl-2,2'-bipyridine 22 (1.4 g, 5.6 mmol) was added carefully and gradually over 15 min to sulfuric acid (10 mL) at 0° C. under vigorous stirring (violent exothermic acid-base reaction). Chromium (VI) oxide (1.7 g, 17 mmol) was added to the reaction mixture in 5-6 portions to maintain reaction temperature below 4° C. The resulting thick green slurry of reaction mixture was allowed to stir overnight at room temperature. It was poured over ice cooled water, and the resulting white solid was filtered, washed with cold water and dried overnight under reduced pressure to give carboxylic acid 23 as a white solid (1.41 g, 90%), mp 248-260° C. (decomposition). $^1$H NMR (600 MHz, DMSO) δ 7.77-7.78 (d, J=7.9 Hz, 1H), 7.96-7.99 (t, J=7.9 Hz, 1H), 8.13-8.18 (m, 2H), 8.48-8.49 (dd, J=7.5, 1.1 Hz, 1H), 8.55-8.57 (d, J=7.7 Hz, 1H). $^{13}$C NMR (150 MHz, DMSO): δ 120.9, 124.3, 125.9, 129.4, 139.6, 141.3, 141.6, 148.6, 154.0, 156.3, 166.3 ppm.

Synthesis of methyl 6'-bromo-2,2'-bipyridine-6-carboxylate (24)

A mixture of 6'-bromo-2,2'-bipyridine-6-carboxylic acid 23 (1.11 g, 4 mmol) in methanol (15 mL) and conc. sulfuric acid (1.5 mL) was stirred at room temperature for 5 minutes. The reaction mixture was heated in a microwave synthesizer at 80° C. for 2 h. The solvent was removed under reduced pressure, and the residue was suspended in water, basified with sodium hydroxide and extracted with dichloromethane. The organic extract was washed with brine, dried over anhydrous sodium sulfate and the solvent was removed under reduced pressure. The product was purified by flash chromatography on silica gel in ethyl acetate/hexanes (10-30%) to get 24 as white a solid (1.17 g, 99%). mp 143-144° C. $^1$H NMR (600 MHz, CDCl$_3$) δ 4.06 (s, 3H), 7.75-7.77 (dd, J=7.7, 1.1 Hz, 1H), 8.00-8.02 (t, J=8.1 Hz, 1H), 8.02-8.05 (t, J=7.9 Hz, 1H), 8.20-8.22 (dd, J=7.7, 1.1 Hz, 1H), 8.67-8.68 (dd, J=7.9, 1.0 Hz, 1H), 8.82-8.83 (dd, J=8.2, 1.1 Hz, 1H). $^{13}$C NMR (150 MHz, CDCl$_3$): δ 53.0, 117.3, 124.7, 124.8, 126.0, 128.6, 133.2, 138.2, 138.4, 147.7, 154.3, 156.7, 165.5 ppm. HRMS: (ESI) calcd for $C_{12}H_9BrN_2O_2$ [M+Na]$^+$ 314.9745. found, 314.9739.

Synthesis of methyl 6'-cyano-2,2'-bipyridine-6-carboxylate (25)

To a solution of methyl 6'-bromo-2,2'-bipyridine-6-carboxylate 24 (0.673 g, 2.3 mmol, 1 equiv) in DMF (5 mL) in a microwave vial was added cuprous cyanide (0.31 g, 3.45 mmol, 1.5 equiv). The reaction mixture was heated in a microwave synthesizer at 160° C. for 1 h. The reaction mixture was allowed to cool to room temperature. A warm aqueous solution of potassium cyanide (0.6 g in 5 mL of water) was added, which resulted in the precipitation of a white solid. The resulting suspension was stirred for 1 h at room temperature, and extracted with ether. The combined organic extract was washed with brine, dried over anhydrous sodium sulfate, and the solvent was removed under reduced pressure. The residue was purified by flash chromatography on silica gel in dichloromethane to give 25 as a white solid (440 mg, 75%); mp 198-201° C. $^1$H NMR (600 MHz, CDCl$_3$) δ 4.06 (s, 3H), 7.75-7.77 (dd, J=7.7, 1.1 Hz, 1H), 8.00-8.02 (t, J=8.1 Hz, 1H), 8.02-8.05 (t, J=7.9 Hz, 1H), 8.20-8.22 (dd, J=7.7, 1.1 Hz, 1H), 8.67-8.68 (dd, J=7.9, 1.0 Hz, 1H), 8.82-8.83 (dd, J=8.2, 1.1 Hz, 1H). $^{13}$C NMR (150 MHz, CDCl$_3$): δ 53.0, 117.3, 124.7, 124.8, 126.0, 128.6, 133.2, 138.2, 138.4, 147.7, 154.3, 156.7, 165.5 ppm. HRMS: (ESI) calcd for $C_{13}H_9N_3O_2$ [M+Na]$^+$ 262.0592. found, 262.0627.

Synthesis of methyl 6'-(aminomethyl)-2,2'-bipyridine-6-carboxylate (26)

To a mixture of nitrile 25 (720 mg, 3 mmol) in MeOH (15 mL) and trifluoroacetic acid (1 mL) was added 5% Pd/C (70 mg, 5 wt-%). The reaction mixture was stirred under hydrogen at 3 atm for 6 h. After disappearance of starting material (TLC), the reaction mixture was filtered through a pad of celite to remove palladium catalyst, concentrated under reduced pressure. The product 26 was used in the next step with no further purification.

Synthesis of (S,E)-methyl 6'-((3-hydroxy-7-(tritylthio)hept-4-enamido)methyl)-2,2'-bipyridine-6-carboxylate (27)

To a solution of the above obtained crude amine product 26 (729 mg, 3 mmol, 1 equiv) in dichloromethane (15 mL) was added DMAP (369 mg, 3 mmol, 1 equiv), and Hunig's base (390 mg, 3 mmol, 1 equiv). The reaction mixture was stirred at room temperature for 30 min before adding a solution of aldol product 8 (1.68 g, 3 mmol, 1 equiv) in dichloromethane (25 mL). The reaction mixture was stirred at room temperature overnight, concentrated in vacuo, and purified by flash chromatography on silica gel in ethyl acetate/hexanes (80-100%) to get 27 as a yellow oil (1.66 g, 85%). [α]$_D^{22}$ +1.7 (c 0.002, CHCl$_3$). $^1$H NMR (600 MHz, CDCl$_3$) δ 1.96 (brs, 1H), 2.07-2.10 (q, J=8.4 Hz, 2H), 2.20-2.22 (t, J=7.1 Hz, 2H), 2.46-2.55 (m, 2H), 3.77 (bb, 1H), 4.05 (s, 1H), 4.51 (m, 1H), 4.65-4.66 (d, J=5.1 Hz, 2H), 5.46-5.49 (dd, J=15.4, 6.2 Hz, 1H), 5.57-5.61 (dt, J=15.2, 6.6 Hz, 1H), 7.20-7.23 (t, J=7.3 Hz, 3H), 7.27-7.30 (t, J=8.0 Hz, 6H), 7.40-7.42 (d, J=7.6 Hz, 6H), 7.81-7.84 (t, J=7.7 Hz, 1H), 7.94-7.97 (t, J=7.9 Hz, 1H), 8.14-8.16 (dd, J=7.7, 0.9 Hz, 1H), 8.42-8.44 (d, J=7.7 Hz, 1H), 8.56-8.58 (dd, J=8.1, 1.1 Hz, 1H). $^{13}$C NMR (150 MHz, CDCl$_3$): δ 31.3, 31.5, 42.7, 44.4, 53.0, 66.6, 69.3, 76.9, 77.1, 77.3, 120.4, 122.5, 124.3, 125.2, 126.7, 126.7, 127.9, 127.9, 129.6, 130.1, 132.4, 138.0, 144.8, 147.6, 154.5, 155.7, 156.0, 165.8, 171.9 ppm. HRMS: (ESI) calcd for C$_{39}$H$_{37}$N$_3$O$_4$S [M+Na]$^+$ 666.2398. found 666.2371.

Synthesis of methyl 6'-((5R,8S)-1-(9H-fluoren-9-yl)-5-isopropyl-3,6,10-trioxo-8-((E)-4-(tritylthio)but-1-enyl)-2,7-dioxa-4,11-diazadodecan-12-yl)-2,2'-bipyridine-6-carboxylate (28)

To a solution of Fmoc-L-valine (408 mg, 1.2 mmol, 2 equiv) in THF (5 mL) at 0° C. was added Hunig's base (234 mg, 1.8 mmol, 3 equiv) and 2,4,6-tricholorobenzoyl chloride (320 mg, 1.3 mmol, 2.1 equiv). The reaction mixture was stirred for 1 h at 0° C. When TLC showed the formation of anhydride, a solution of alcohol 27 (387 mg, 0.6 mmol, 1 equiv) and DMAP (74 mg, 0.6 mmol, 1 equiv) in THF (8 mL) was added to the reaction mixture at 0° C. The reaction mixture was stirred at room temperature overnight, concentrated in vacuo, and purified by flash chromatography on silica gel in ethyl acetate/hexanes (50-70%), followed by a second purification by reversed phase chromatography on C$_{18}$ in acetonitrile/water (40-100%) to get 28 as a yellow oil (530 mg, 92%). $[α]_D^{22}$ +8.6 (c 0.08, CHCl$_3$). $^1$H NMR (600 MHz, CDCl$_3$) δ 0.84-0.85 (d, J=6.8 Hz, 3H), 0.91-0.92 (d, J=6.8 Hz, 3H), 2.06-2.12 (m, 2H), 2.17-2.24 (m, 2H), 2.64-2.67 (dd, J=14.7, 6.3 Hz, 1H), 2.70-2.74 (dd, J=14.5, 7.3 Hz, 1H), 4.04 (s, 1H), 4.18-4.21 (m, 2H), 4.30-4.32 (dd, J=10.4, 7.0 Hz, 1H), 4.36-4.39 (dd, J=10.3, 7.3 Hz, 1H), 4.63 (d, J=5.1 Hz, 1H), 5.44-5.46 (m, 1H), 5.38-5.51 (dd, J=15.2, 7.5 Hz, 1H), 5.71-5.76 (m, 2H), 7.09 (m, 1H), 7.21-7.24 (t, J=7.4 Hz, 3H), 7.25-7.26 (d, J=7.7 Hz, 1H), 7.28-7.32 (m, 8H), 7.38-7.40 (dd, J=7.4, 3.1 Hz, 2H), 7.42-7.43 (d, J=7.0 Hz, 6H), 7.57-7.59 (dd, J=7.1, 4.4 Hz, 2H), 7.75-7.78 (t, J=7.7 Hz, 3H), 7.90-7.92 (t, J=7.7 Hz, 1H), 8.12-8.13 (d, J=6.7 Hz, 1H), 8.41-8.42 (d, J=7.7 Hz, 1H), 8.56-8.58 (d, J=7.9 Hz, 1H). HRMS: (ESI) calcd for C$_{59}$H$_{56}$N$_4$O$_7$S [M+Na]$^+$ 987.3789. found 987.3705.

Synthesis of cyclic core of JA2 (29)

To a solution of 28 (126 mg, 0.131 mmol, 1 equiv) in THF/H$_2$O (4:1, 2 mL) at 0° C. was added 0.1M LiOH (1.3 mL, 0.13 mmol, 1.0 equiv) dropwise over a period of 10 minutes. The reaction mixture was stirred at 0° C. for another 1 h, and 1M HCl solution (1.3 mL, 0.13 mmol, 1.0 equiv) was added. It was extracted with ethyl acetate and the organic extract was washed with brine, dried over anhydrous sodium sulfate and the solvent removed under reduced pressure to give the crude carboxylic acid which was used in the next step without further purification.

To a solution of the crude carboxylic acid in dichloromethane (5 mL) was added diethylamine (0.94 g, 12.5 mmol, 96 equiv). After stirring at room temperature for 12 h, the reaction mixture was concentrated under reduced pressure, and the residue was dried for 12 h in high vacuo to give the crude product, which was used in the next step without additional purification.

A mixture of the crude product obtained above, HATU (0.10 g, 0.26 mmol, 2.0 equiv), HOAt (0.036 g, 0.26 mmol, 2.0 equiv), and Hunig's base (0.075 g, 0.572 mmol, 4.4 equiv) in dichloromethane (130 mL) was stirred for 3 days at room temperature. It was concentrated in vacuo and diluted with dichloromethane (15 mL), washed with brine and evaporated under reduced pressure. The residue was partially purified by flash chromatography on silica gel in ethyl acetate to give 29 as a yellow oil (41 mg, 45%). $^1$H NMR (600 MHz, CDCl$_3$) δ 1.00-1.02 (d, J=6.8 Hz, 3H), 1.04-1.05 (d, J=6.8 Hz, 3H), 1.43-1.51 (m, 6H), 1.69-1.74 (m, 2H), 1.83 (bb, 1H), 1.87-1.96 (m, 2H), 2.39-2.42 (m, 1H), 3.18-3.2 (q, J=7.3 Hz, 1H), 3.71-3.76 (m, 1H), 4.50-4.54 (dd, J=17.2, 2.5 Hz, 1H), 4.84-4.89 (m, 2H), 5.33-5.37 (dd, J=15.4, 5.3 Hz, 1H), 5.54-5.59 (dt, J=15.6, 5.6 Hz, 1H), 5.76 (m, 1H), 7.17-7.20 (tt, J=6.9, 1.5 Hz, 3H), 7.21-7.224 (dt, J=7.0, 1.7 Hz, 6H), 7.25-7.27 (m, 5H), 7.29 (s, 1H), 7.39-7.41 (m, 1H), 7.83 (m, 2H), 7.00-8.02 (m, 2H), 8.18 (m, 1H), 9.66-9.68 (d, J=9.9 Hz, 1H).

Synthesis of Analogue JA2

To a solution of the cyclized product 29 (23 mg, 0.032 mmol, 1 equiv) and triisopropylsilane (8 mg, 0.048 mmol, 1.5 equiv) in dichloromethane (2 mL) at 0° C. was added trifluoroacetic acid (0.11 g, 0.96 mmol, 30 equiv). The reaction mixture was stirred overnight at room temperature and the solvent was removed under reduced pressure. The residue was dried azeotropically with toluene, and used in the next step without additional purification.

To a stirred solution of the above crude thiol (0.032 mmol, 1 equiv) and DMAP (1.0 mg) in dichloromethane (2 mL) at 0° C. was added Hunig's base (13 mg, 0.096 mmol, 3 equiv) and octanoyl chloride (13 mg, 0.08 mmol, 2.5 equiv). The reaction mixture was stirred at room temperature overnight. It was concentrated in vacuo, and purified by flash chromatography on silica gel in 20-50% acetone/hexanes to give product JA2 as a colorless oil (12 mg, 65%). $[α]_D^{22}$ +6.7 (c 0.004, CHCl$_3$). $^1$H NMR (600 MHz, CDCl$_3$) δ 0.88-0.90 (t, J=7.1 Hz, 3H), 1.03-1.04 (d, J=6.8 Hz, 3H), 1.06-1.07 (d, J=6.8 Hz, 3H), 1.24-1.34 (m, 8H), 1.56-1.59 (quin, J=7.1 Hz, 2H), 1.75 (m, 3H), 1.99-2.09 (m, 2H), 2.39-2.45 (m, 4H), 2.46-2.51 (m, 1H), 2.86-2.87 (d, J=4.6 Hz, 2H). $^{13}$C NMR (150 MHz, CDCl$_3$): δ 14.1, 17.7, 19.1, 22.6, 25.6, 27.6, 28.9, 31.6, 32.1, 33.0, 41.6, 44.0, 44.6 58.0, 70.5, 76.8, 77.0, 77.3, 119.8, 121.4, 122.1, 123.1, 127.3, 131.5, 137.7, 138.8, 149.4, 153.2, 153.3, 156.1, 163.6, 169.0, 169.2, 199.1 ppm. HRMS: (ESI) calcd for C$_{43}$H$_{42}$N$_4$O$_4$S [M+Na]$^+$ 617.2774. found 617.2775.

Synthesis of (6-(hydroxymethyl)pyridin-2-yl)methyl 4-methylbenzenesulfonate (31)

A mixture of 2,6-pyridinedimethanol 30 (1.39 g, 10 mmol, 1 equiv), silver oxide (4.00 g, 15 mmol, 1.4 equiv), and potassium iodide (0.35 g, 2 mmol, 0.2 equiv) in dichloromethane (70 mL) was cooled to −20° C. Tosyl chloride (1.90 g, 10 mmol, 1 equiv) was added and the reaction mixture was stirred at −20° C. for 30 min. It was warmed to room temperature and stirred for an additional 3 h. The reaction mixture was filtered through a celite pad, and washed with ethyl acetate. The solvent was removed under reduced pressure and the residue was purified by flash chromatography on silica gel in dichloromethane/hexanes (20-100%) to give 31 as a pink oil (2.4 g, 82%). $^1$H NMR (600 MHz, CDCl$_3$) δ 2.46 (s, 3H), 4.71 (s, 2H), 5.16 (s, 2H), 7.19-7.21 (d, J=7.7 Hz, 1H), 7.33-7.34 (d, J=7.7 Hz, 1H), 7.35-7.37 (d, J=8.1 Hz, 2H), 7.69-7.72 (t, J=7.9 Hz, 1H), 7.83-7.85 (d, J=6.6 Hz, 2H). $^{13}$C NMR (150 MHz, CDCl$_3$): δ 21.7, 63.8, 71.4, 120.2, 120.6, 128.1, 129.9, 132.8, 137.7, 145.1, 152.6, 158.9 ppm.

Synthesis of (6-(azidomethyl)pyridin-2-yl)methanol (32)

A mixture of compound 31 (1.66 g, 5.67 mmol) and NaN$_3$ (1.1 g, 17.01 mmol) in DMF (40 mL) was stirred at 80° C. for 3 h. The solvent was removed under reduced pressure and the residue was dissolved in ethyl acetate, filtered through a pad of celite, and evaporated in vacuo to give 32 as a greenish solid (920 mg, 98%). $^1$H NMR (600 MHz, CDCl$_3$) δ 4.48 (s, 2H), 4.78 (s, 2H), 7.22-7.24 (d, J=7.7 Hz, 1H), 7.25-7.26 (d, J=6.5 Hz, 1H), 7.72-7.75 (t, J=7.5 Hz, 1H). $^{13}$C NMR (150 MHz, CDCl$_3$): δ 55.3, 64.0, 119.7, 120.5, 137.7, 154.9, 159.3 ppm.

Synthesis of (6-(azidomethyl)pyridin-2-yl)methyl 4-methylbenzenesulfonate (33)

To a mixture of compound 32 (380 mg, 2.3 mmol, 1 equiv) in THF (2 mL) and water (2 mL) at 0° C. was added NaOH (0.27 g, 6.9 mmol, 3 equiv), followed by dropwise addition of a solution of tosyl chloride (0.483 g, 2.53 mmol, 1.1 equiv) in THF (2 mL). The suspension was stirred at 0° C. for 4 h and extracted with dichloromethane. The combined organic extract was washed with brine, dried over anhydrous sodium sulfate, and the solvent was removed under reduced pressure to give compound 33 as a yellow oil (621 mg, 85%). $^1$H NMR (600 MHz, CDCl$_3$) δ 2.47 (s, 3H), 4.42 (s, 3H), 5.16 (s, 2H), 7.28-7.29 (d, J=6.4 Hz, 1H), 7.36-7.37 (d, J=8.4 Hz, 2H), 7.39-7.41 (d, J=7.9 Hz, 1H), 7.73-7.76 (t, J=7.7 Hz, 1H), 7.84-7.86 (d, J=6.8 Hz, 2H). $^{13}$C NMR (150 MHz, CDCl$_3$): δ 21.7, 55.3, 71.5, 121.0, 121.5, 128.1, 129.9, 132.8, 138.0, 145.0, 153.9, 155.5 ppm.

General Procedure for the Preparation of Tertiary Amines 38-41

A mixture of 2-tosylmethyl-6-azidomethylpyridine 33 (1 mmol, 1 equivalent), amine 34-37 (1 mmol, 1 equivalent), and potassium carbonate (2 mmol, 2 equivalent) in acetonitrile (10 mL) was refluxed under nitrogen for 3 h. When TLC showed disappearance of starting materials, the reaction mixture was cooled to room temperature, treated with water, and extracted three times with ethyl acetate. The organic extract was dried over anhydrous sodium sulfate, filtered and solvent removed under reduced pressure. The residue was purified by flash column chromatography on silica gel in dichloromethane/ethyl acetate (10-50%).

Synthesis of methyl 2-(((6-(azidomethyl)pyridin-2-yl)methyl)(methyl)amino)acetate (38)

Yellow oil (0.20 g, 81%). $^1$H NMR (600 MHz, CDCl$_3$) δ 2.45 (s, 3H), 3.38 (s, 2H), 3.73 (s, 3H), 3.86 (s, 3H), 4.47 (s, 2H), 7.23-7.24 (d, J=7.7 Hz, 1H), 7.44-7.45 (d, J=7.7 Hz, 1H), 7.70-7.72 (t, J=7.7 Hz, 1H). $^{13}$C NMR (150 MHz, CDCl$_3$): δ 42.6, 51.6, 55.6, 57.9, 62.5, 120.4, 122.4, 137.5, 155.1, 158.9, 171.4 ppm. HRMS: (ESI) calcd for C$_{11}$H$_{15}$N$_5$O$_2$ [M+Na]$^+$ 272.1123. found 272.1134.

Synthesis of methyl 2-(((6-(azidomethyl)pyridin-2-yl)methyl)(benzyl)amino)acetate (39)

Yellow oil (0.30 g, 86%). $^1$H NMR (600 MHz, CDCl$_3$) δ 3.42 (s, 2H), 3.71 (s, 3H), 3.86 (s, 2H), 3.98 (s, 2H), 4.46 (s, 2H), 7.21-7.23 (d, J=7.5 Hz, 1H), 7.25-7.28 (t, J=7.3 Hz, 1H), 7.32-7.35 (t, J=7.7 Hz, 2H), 7.40-7.42 (d, J=7.6 Hz, 1H), 7.57-7.59 (d, J=7.7 Hz, 1H), 7.71-7.73 (t, J=7.7 Hz, 1H). $^{13}$C NMR (150 MHz, CDCl$_3$) δ 51.5, 54.2, 55.6, 58.1, 59.6, 120.3, 122.2, 127.3, 128.4, 129.0, 137.5, 138.5, 154.9, 159.8, 171.7 ppm. HRMS: (ESI) calcd for C$_{17}$H$_{19}$N$_5$O$_2$ [M+Na]$^+$ 362.1593. found 362.1576.

Synthesis of methyl 2-(((6-(azidomethyl)pyridin-2-yl)methyl)(4-(trifluoromethyl)benzyl)amino)acetate (40)

Yellow oil (0.35 g, 89%), $^1$H NMR (600 MHz, CDCl$_3$) δ 3.39 (s, 2H), 3.71 (s, 3H), 3.78 (s, 2H), 3.81 (s, 3H), 3.96 (s, 2H), 4.46 (s, 2H), 6.86-6.88 (d, J=8.6 Hz, 2H), 7.21-7.23 (d, J=7.7 Hz, 1H), 7.31-7.32 (d, J=8.6 Hz, 2H), 7.56-7.57 (d, J=7.7 Hz, 1H), 7.71-7.73 (t, J=7.7 Hz, 1H). $^{13}$C NMR (150 MHz, CDCl$_3$): δ 51.5, 54.0, 55.3, 55.6, 57.5, 59.4, 113.7, 120.3, 122.2, 130.2, 130.4, 137.5, 154.8, 158.9, 159.9, 171.8 ppm. HRMS: (ESI) calcd for C$_{18}$H$_{21}$N$_5$O [M+Na]$^+$ 373.1542. found 373.1615.

Synthesis of methyl 2-(((6-(azidomethyl)pyridin-2-yl)methyl)(4-methoxybenzyl)amino)acetate (41)

Yellow oil (0.25 g, 77%). $^1$H NMR (600 MHz, CDCl$_3$) δ 3.43 (s, 2H), 3.73 (s, 3H), 3.92 (s, 2H), 3.98 (s, 2H), 4.46 (s, 2H), 7.23-7.24 (d, J=7.5 Hz, 1H), 7.51-7.52 (d, J=7.7 Hz, 1H), 7.54-7.55 (d, J=8.1 Hz, 2H), 7.58-7.60 (d, J=8.1 Hz, 2H), 7.72-7.74 (t, J=7.7 Hz, 1H). $^{13}$C NMR (150 MHz, CDCl$_3$): δ 51.5, 54.3, 55.5, 57.7, 59.6, 120.5, 122.2, 125.1, 125.3, 125.3, 125.3, 125.3, 129.1, 129.4, 129.6, 137.6, 142.9, 155.0, 159.3, 171.5 ppm. HRMS: (ESI) calcd for C$_{18}$H$_{18}$F$_3$N$_5$O$_2$ [M+Na]$^+$ 416.1310. found 416.1315.

General Procedure for Reduction (Hydrogenation) of Azide/Nitrile to the Corresponding Primary Amine (42-45)

A mixture of azide/nitrile 38-41 (3 mmol) dissolved in MeOH (15 mL) and 5% Pd/C (10 wt. %) was stirred under hydrogen at 3 atm for 6-8 h. After disappearance of starting material (TLC), the reaction mixture was filtered through a pad of celite, concentrated in vacuo and used in the next step without further purification.

Synthesis of (S,E)-methyl 2-(((6-((3-hydroxy-7-(tritylthio)hept-4-enamido)methyl)pyridin-2-yl)methyl)(methyl)amino)acetate (46)

To a solution of the crude amine product 42 (1.25 g, 5.6 mmol, 1 equiv) in dichloromethane (25 mL) was added DMAP (690 mg, 5.6 mmol, 1 equiv), and Hunig's base (728 mg, 5.6 mmol, 1 equiv). The reaction mixture was stirred at room temperature for 30 min before adding a solution of the aldol product 8 (3.1 g, 5.5 mmol, 1 equiv) in dichloromethane (40 mL). The reaction mixture was stirred at room temperature overnight, concentrated in vacuo and purified by flash chromatography on silica gel in dichloromethane/ethyl acetate (30-50%) to get 46 as a yellow oil (2.97 g, 85%). [α]$_D^{22}$ −6.5 (c 0.02, CHCl$_3$). $^1$H NMR (600 MHz, CDCl$_3$) 2.08-2.11 (m, 2H), 2.21-2.24 (t, J=7.5 Hz, 2H), 2.44 (s, 3H), 2.40-2.45 (m, 2H), 3.37 (s, 2H), 3.71 (s, 3H), 3.84 (s, 2H), 4.46-4.51 (m, 2H), 4.62-4.65 (dd, J=6.5, 5.3 Hz, 1H), 5.45-5.49 (dd, J=15.2, 6.1 Hz, 1H), 5.58-5.63 (m, 1H), 7.12-7.14 (d, J=7.7 Hz, 1H), 7.20-7.23 (t, J=9.1 Hz, 3H), 7.28-7.30 (t, J=7.9 Hz, 6H), 7.33-7.34 (d, J=7.7 Hz, 1H), 7.41-7.42 (d, J=8.1 Hz, 6H), 7.63-7.66 (t, J=7.5 Hz, 1H). $^{13}$C NMR (150 MHz, CDCl$_3$): δ 31.4, 31.5, 42.6, 43.0, 44.2, 51.6, 57.8, 62.3, 66.6, 69.1, 120.4, 121.9, 126.6, 127.9, 129.6, 132.7, 137.3, 144.9, 155.7, 157.9, 171.4, 172.1 ppm. HRMS: (ESI) calcd for C$_{37}$H$_{41}$N$_3$O$_4$S [M+H]$^+$ 624.2896. found 624.2897.

Synthesis of (R)—((S,E)-1-((6-(((2-methoxy-2-oxoethyl)(methyl)amino)methyl)pyridin-2-yl)methylamino)-1-oxo-7-(tritylthio)hept-4-en-3-yl) 2-(((9H-fluoren-9-yl)methoxy)carbonylamino)-3-methylbutanoate (50)

To a solution of Fmoc-L-valine (1.40 g, 4.2 mmol, 2 equiv) in THF (15 mL) at 0° C. was added Hunig's base (0.82 g, 6.3 mmol, 3 equiv) and 2,4,6-tricholorobenzoyl chloride (1.1 g, 4.6 mmol, 2.1 equiv). The reaction mixture was stirred for 1 h at 0° C. When TLC showed the formation of the anhydride product, a solution of alcohol 46 (1.31 g, 2.1 mmol, 1 equiv) and DMAP (0.26 g, 2.1 mmol, 1 equiv) in THF (20 mL) were added to the reaction mixture at 0° C. The reaction mixture was stirred at room temperature overnight, concentrated in vacuo and purified by flash chromatography on silica gel in dichloromethane/ethyl acetate (20-50%), followed by a second purification by reversed phase chromatography on C$_{18}$ in acetonitrile/water (40-100%) to get 50 as a yellow oil (1.8 g, 90%). [α]$_D^{22}$ −5.5 (c 0.04, CHCl$_3$). $^1$H NMR (600 MHz, CDCl$_3$) δ 0.83-0.84 (d, J=6.7 Hz, 3H), 0.91-0.93 (d, J=6.8 Hz, 1H), 2.05-2.09 (m, 2H), 2.11-2.14 (q, J=6.5 Hz, 1H), 2.192-0.22 (m, 2H), 2.44 (s, 3H), 2.57-2.60 (dd, J=15.7, 5.1 Hz, 1H), 2.66-2.69 (dd, J=14.5, 7.5 Hz, 1H), 3.36 (s, 2H), 3.72 (s, 3H), 3.83 (s, 2H), 4.20-4.23 (m, 2H), 4.32-4.35 (m 1H), 4.37-4.40 (m, 1H), 4.51-4.52 (t, J=4.8 Hz, 2H), 5.38-5.40 (d, J=8.6 Hz, 1H), 5.43-5.47 (dd, J=15.2, 7.4 Hz, 1H), 5.69-5.72 (m, 2H), 6.98 (m, 1H), 7.08-7.09 (d, J=7.5 Hz, 1H), 7.21-7.23 (t, J=7.3 Hz, 3H), 7.28-7.30 (t, J=7.9 Hz, 6H), 7.32-7.34 (t, J=7.3 Hz, 3H), 7.40-7.43 (m, 9H), 7.59-7.62 (m, 3H), 7.77-7.78 (d, J=7.5 Hz, 2H). $^{13}$C NMR (150 MHz, CDCl$_3$): δ 17.5, 19.0, 31.2, 31.3, 31.4, 41.6, 42.7, 44.5, 47.2, 51.6, 57.9, 59.0, 62.4, 66.6, 67.0, 72.6, 120.0, 120.0, 120.4, 121.8, 125.1, 126.6, 127.1, 127.7, 127.9, 128.0, 129.6, 133.8, 137.3, 141.3, 143.8, 143.9, 144.8, 155.7, 156.2, 157.8, 168.7, 171.0, 171.4 ppm. HRMS: (ESI) calcd for C$_{57}$H$_{60}$N$_4$O$_7$S [M+H]$^+$ 945.4261. found 945.4244.

Synthesis of Cyclic Core of JA3 (54)

To a solution of 50 (100 mg, 0.104 mmol, 1 equiv) in THF/H$_2$O (4:1, 2 mL) at 0° C. was added 0.1M LiOH (1.0 mL, 0.10 mmol, 1.0 equiv) drop wise over a period of 10 minutes. The reaction mixture was stirred at 0° C. for 1 h, after which a solution of 0.1M HCl (1.1 mL, 0.11 mmol, 1.1 equiv) was added and the reaction mixture was extracted with ethyl acetate. The organic extract was washed with brine, dried over anhydrous sodium sulfate, and the solvent was removed under reduced pressure to give the crude carboxylic acid, which was used in the next step without further purification.

To a solution of the crude carboxylic acid in dichloromethane (5 mL) was added diethylamine (0.72 g, 9.6 mmol, 96 equiv). After stirring at room temperature for 8 h, the reaction mixture was concentrated reduced pressure and dried in high vacuum to give the crude product. It was used in the next step without further purification.

To a mixture of the crude product obtained above, HATU (0.076 g, 0.20 mmol, 2.0 equiv), and HOAt (0.027 g, 0.20 mmol, 2.0 equiv) in dichloromethane (100 mL) was added Hunig's base (0.057 g, 0.44 mmol, 4.4 equiv). The reaction mixture was stirred for 3 days at room temperature, concentrated in vacuo, and diluted with dichloromethane. The dichloromethane solution was washed with brine and evaporated under reduced pressure. The residue was purified by flash chromatography on silica gel in ethyl acetate to give 54 as a yellow oil (24 mg, 35%). [α]$_D^{22}$ −18.2 (c 0.02, CHCl$_3$). $^1$H NMR (600 MHz, CDCl$_3$) δ 0.77-0.78 (d, J=6.7 Hz, 3H), 0.88-0.99 (d, J=6.8 Hz, 3H), 1.99-2.02 (q, J=7.0 Hz, 2H), 2.11-2.16 (m, 2H), 2.22-2.37 (m, 2H), 2.30 (s, 3H), 2.62-2.66 (dd, J=15.2, 7.3 Hz, 1H), 2.75-2.77 (d, J=13.6 Hz, 1H), 3.24-3.34 (q, J=16.9 Hz, 2H), 3.54-3.56 (d, J=13.4 Hz, 1H), 3.80-3.83 (d, J=13.6 Hz, 1H), 4.56-4.59 (m, 2H), 4.82-4.84 (dd, J=9.9, 4.2 Hz, 1H), 5.37-5.40 (dd, J=15.3, 6.1 Hz, 1H), 5.60 (m, 1H), 5.65-5.70 (dt, J=15.4, 6.4 Hz, 1H), 7.10-7.13 (dd, J=12.3, 7.0 Hz, 2H), 7.20-7.23 (t, J=13.4 Hz, 3H), 7.28-7.29 (t, J=2.9 Hz, 5H), 7.30-7.34 (m, 1H), 7.37-7.38 (d, J=7.5 Hz, 5H), 7.40 (m, 1H), 7.43-7.47 (m, 1H), 7.64-7.66 (t, J=7.5 Hz, 1H) 8.66-8.68 (d, J=9.9 Hz, 1H). $^{13}$C NMR (150 MHz, CDCl$_3$): δ 17.5, 19.1, 31.1, 31.5, 32.5, 41.7, 42.8, 44.3, 57.0, 61.1, 62.9, 66.6, 71.9, 121.1, 122.0, 126.6, 127.4, 127.9, 129.6, 132.6, 137.3, 144.8, 155.6, 157.3, 169.1, 169.3, 170.4 ppm. HRMS: (ESI) calcd for C$_{41}$H$_{46}$N$_4$O$_4$S [M+Na]$^+$ 713.3137. found 713.3167.

Synthesis of Analogue JA3

To a solution of the cyclized product 54 (15 mg, 0.022 mmol, 1 equiv) and triisopropylsilane (6 mg, 0.033 mmol, 1.5 equiv) in dichloromethane (2 mL) at 0° C. was added trifluoroacetic acid (0.08 g, 0.66 mmol, 30 equiv). The reaction mixture was stirred for 4 h at room temperature. It was concentrated in vacuo, dried azeotropically with toluene, and used in the next step.

To a stirred mixture of the above obtained crude thiol and DMAP (1.0 mg) in dichloromethane (2 mL) at 0° C. was added Hunig's base (9 mg, 0.066 mmol, 3 equiv) and octanoyl chloride (9 mg, 0.055 mmol, 2.5 equiv). The reaction mixture was stirred at room temperature overnight. It was concentrated in vacuo and purified by flash chromatography on silica gel in 20-50% acetone/hexanes to give product JA3 as colorless oil (5 mg, 41%). [α]$_D^{22}$ −7.4 (c 0.002, CHCl$_3$). $^1$H NMR (600 MHz, CDCl$_3$) δ 0.78-0.79 (d, J=6.8 Hz, 3H), 0.88-0.90 (m, 6H), 1.28-1.32 (m, 8H), 1.62-1.66 (m, 2H), 2.24-2.30 (m, 3H), 2.38 (s, 3H), 2.50-2.53 (t, J=7.6 Hz, 2H), 2.66-2.70 (m, 1H), 2.76-2.2.85 (m, 3H), 3.28-3.31 (d, J=15.0 Hz, 1H), 3.39-3.41 (d, J=16.8 Hz, 1H), 3.58-3.60 (d, J=13.6 Hz, 1H), 3.86-3.88 (d, J=13.6 Hz, 1H), 4.55-4.64 (dq, J=17.1, 4.2 Hz, 2H), 4.85-4.87 (dd, J=10.1, 4.4 Hz, 1H), 5.51-5.55 (dd, J=15.6, 6.1 Hz, 1H), 5.66 (m, 1H), 5.79-5.83 (dt, J=15.6, 6.8 Hz, 1H), 7.12-7.14 (d, J=7.5 Hz, 1H), 7.18-7.19 (d, J=7.7 Hz, 1H), 7.42 (s, 1H), 7.66-7.69 (t, J=7.7 Hz, 1H), 8.68-8.70 (d, J=10.1 Hz, 1H). $^{13}$C NMR (150 MHz, CDCl$_3$): δ 14.1, 17.4, 19.1, 22.6, 25.6, 27.8, 28.9, 31.6, 32.3, 32.5, 41.8, 42.8, 44.1, 44.3, 57.1, 61.1, 62.9, 72.0, 121.2, 122.1, 128.0, 132.3, 137.4, 155.6, 157.3, 169.1, 169.3, 170.4, 199.3 ppm. HRMS: (ESI) calcd for C$_{30}$H$_{46}$N$_4$O$_5$S [M+H]$^+$ 575.3189. found 375.3198.

Synthesis of (S,E)-methyl 2-(benzyl((6-((3-hydroxy-7-(tritylthio)hept-4-enamido)methyl)pyridin-2-yl)methyl)amino)acetate (47)

To a solution of the crude amine product 43 (0.96 g, 3.2 mmol, 1 equiv) in dichloromethane (20 mL) was added DMAP (395 mg, 3.2 mmol, 1 equiv), and Hunig's base (416 mg, 3.2 mmol, 1 equiv). The reaction mixture was stirred at room temperature for 30 min at room temperature before adding a solution of the aldol product 8 (1.8 g, 3.2 mmol, 1 equiv) in dichloromethane (30 mL). The reaction mixture was stirred at room temperature overnight, concentrated in vacuo, and purified by flash chromatography on silica gel in dichloromethane/ethyl acetate (30-50%) to get 47 as a yellow oil (1.8 g, 81%). $[\alpha]_D^{22}$ −23.4 (c 0.007, CHCl$_3$). $^1$H NMR (600 MHz, CDCl$_3$) δ 2.07-2.11 (m, 2H), 2.20-2.23 (t, J=7.3 Hz, 2H), 2.40-2.44 (dd, J=14.9, 9.2 Hz, 1H), 2.48-2.51 (dd, J=14.9, 2.7 Hz, 1H), 3.40 (s, 2H), 3.69 (s, 3H), 3.84 (s, 2H), 3.95 (s, 2H), 4.45-4.48 (m, 1H), 4.47-4.51 (dd, J=16.5, 4.6 Hz, 1H), 4.60-4.63 (dd, J=16.3, 5.3 Hz, 1H), 5.44-5.48 (dd, J=15.4, 6.2 Hz, 1H), 5.57-5.62 (dt, J=15.4, 6.6 Hz, 1H), 7.11-7.12 (d, J=7.7 Hz, 1H), 7.16 (m, 1H), 7.21-7.23 (t, J=7.5 Hz, 3H), 7.26-7.31 (m, 7H), 7.32-7.35 (t, J=7.7 Hz, 2H), 7.39-7.40 (d, J=7.2 Hz, 2H), 7.41-7.43 (d, J=7.3 Hz, 6H), 7.46-7.48 (d, J=7.7 Hz, 1H), 7.65-7.68 (t, J=7.7 Hz, 1H). $^{13}$C NMR (150 MHz, CDCl$_3$): δ 31.4, 31.5, 42.9, 44.1, 51.6, 54.1, 58.2, 59.3, 66.5, 69.2, 120.4, 121.7, 126.6, 127.4, 127.9, 128.4, 129.0, 129.6, 129.7, 132.5, 137.5, 138.4, 144.9, 155.1, 158.7, 171.2, 172.1 ppm. HRMS: (ESI) calcd for C$_{44}$H$_{47}$N$_3$O$_4$S [M+Na]$^+$ 736.3185. found 736.3199.

Synthesis of (R)-((S,E)-1-((6-((benzyl(2-methoxy-2-oxoethyl)amino)methyl)pyridin-2-yl)methyl-amino)-1-oxo-7-(tritylthio)hept-4-en-3-yl) 2-(((9H-fluoren-9-yl)methoxy)carbonylamino)-3-methylbutanoate (51)

To a solution of Fmoc-L-valine (0.67 g, 2.0 mmol, 2 equiv) in THF (7 mL) at 0° C. was added Hunig's base (0.40 g, 3.0 mmol, 3 equiv) and 2,4,6-tricholorobenzoyl chloride (0.5 g, 2.1 mmol, 2.1 equiv). The reaction mixture was stirred for 1 h at 0° C. When TLC showed the formation of anhydride product, a solution of alcohol 47 (0.70 g, 1.0 mmol, 1 equiv), and DMAP (0.12 g, 1.0 mmol, 1 equiv) in THF (15 mL) were added to the reaction mixture at the same temperature. The reaction mixture was stirred at room temperature overnight, concentrated in vacuo, and purified by flash chromatography on silica gel in dichloromethane/ethyl acetate (20-50%) followed by a second purification by reversed phase flash chromatography on C$_{18}$ in acetonitrile/water (40-100%) to get 51 as a yellow oil (0.87 g, 84%). $[\alpha]_D^{22}$ −16.7 (c 0.042, CHCl$_3$). $^1$H NMR (600 MHz, CDCl$_3$): δ 0.83-0.84 (d, J=6.8 Hz, 3H), 0.91-0.92 (d, J=6.7 Hz, 3H), 1.86-1.88 (quin, J=3.3 Hz, 2H), 2.05-2.09 (m, 2H), 2.11-2.14 (q, J=5.7 Hz, 1H), 2.18-2.22 (m, 2H), 2.57-2.60 (dd, J=14.6, 5.3 Hz, 1H), 2.65-2.69 (dd, J=14.3, 7.7 Hz, 1H), 3.40 (s, 2H), 3.70 (s, 3H), 3.85 (s, 2H), 3.96 (s, 2H), 4.20-4.24 (m, 2H), 4.32-4.39 (m, 2H), 4.50-4.51 (m, 2H), 5.39-5.41 (d, J=8.5 Hz, 1H), 5.43-5.47 (dd, J=15.4, 7.5 Hz, 1H), 5.69-5.74 (quin, J=7.1 Hz, 2H), 6.97 (m, 1H), 7.06-7.07 (d, J=7.6 Hz, 1H), 7.21-7.23 (t, J=7.4 Hz, 3H), 7.25-7.31 (m, 7H), 7.32-7.35 (m, 4H), 7.40-7.42 (m, 10H), 7.45-7.46 (d, J=7.7 Hz, 1H), 7.59-7.63 (m, 3H), 7.77-7.78 (d, J=7.5 Hz, 2H). $^{13}$C NMR (150 MHz, CDCl$_3$): δ 17.5, 19.0, 25.6, 31.2, 31.3, 31.4, 41.6, 44.4, 47.2, 51.5, 54.2, 58.2, 59.0, 59.5, 66.6, 67.0, 68.0, 72.6, 120.0, 120.0, 120.2, 121.4, 125.1, 126.6, 127.1, 127.1, 127.3, 127.9, 128.0, 128.4, 128.9, 129.6, 133.8, 137.3, 138.6, 141.3, 143.8, 143.9, 144.8, 155.3, 156.2, 158.8, 168.6, 171.0, 171.9 ppm. HRMS: (ESI) calcd for C$_{64}$H$_{66}$N$_4$O$_7$S [M+Na]$^+$ 1057.4550. found 1057.4547.

Synthesis of Cyclic Core of analogue JA4 (55)

To a solution of 51 (135 mg, 0.130 mmol, 1 equiv) in THF/H$_2$O (2 mL, 4:1) at 0° C. was added 0.1M LiOH (1.3 mL, 0.13 mmol, 1.0 equiv) drop wise over a period of 10 minutes. The reaction mixture was stirred at 0° C. for 1 h. A solution of 0.1M HCl (1.4 mL, 0.14 mmol, 1.1 equiv) was added and the reaction mixture was extracted with ethyl acetate. The combined organic extract was washed with brine, dried over anhydrous sodium sulfate, and the solvent evaporated under reduced pressure to give the crude carboxylic acid, which was used in the next step without further purification.

To a solution of the crude carboxylic acid in dichloromethane (5 mL) was added diethylamine (1.3 g, 12.5 mmol, 96 equiv). After stirring at room temperature for 4 h, the reaction mixture was concentrated under reduced pressure and the residue was dried in high vacuo to give the crude product. It was used in the next step without further purification.

To a solution of the crude product obtained above, HATU (0.10 g, 0.26 mmol, 2.0 equiv), and HOAt (0.035 g, 0.26 mmol, 2.0 equiv) in dichloromethane (100 mL) was added Hunig's base (0.057 g, 0.44 mmol, 4.4 equiv). The reaction mixture was stirred for 3 days at room temperature, concentrated in vacuo, and diluted with dichloromethane. The dicholormethane extract was washed with brine and the solvent was evaporated under reduced pressure. The residue was purified by flash chromatography on silica gel in ethyl acetate to give 55 as a yellow oil (24 mg, 35%). $[\alpha]_D^{22}$ −60.0 (c 0.035, CHCl$_3$). $^1$H NMR (600 MHz, CDCl$_3$): δ 0.67-0.68 (d, J=6.8 Hz, 3H), 0.81-0.83 (d, J=7.0 Hz, 3H), 2.02-2.10 (m, 2H), 2.20-2.23 (m, 2H), 2.24-2.28 (m, 1H), 2.71-2.72 (m, 2H), 3.20-3.23 (d, J=17.1 Hz, 1H), 3.42-3.45 (d, J=17.1 Hz, 1H), 3.55-3.57 (d, J=13.8 Hz, 1H), 3.71-3.74 (d, J=13.8 Hz, 1H), 3.77-3.79 (d, J=14.1 Hz, 1H), 3.91-3.94 (d, J=14.1 Hz, 1H), 4.46-4.50 (dd, J=16.9, 3.7 Hz, 1H), 4.66-4.69 (dd, J=16.9, 4.3 Hz, 1H), 4.89-4.92 (dd, J=10.3, 4.1 Hz, 1H), 5.39-5.43 (dd, J=15.4, 6.6 Hz, 1H), 5.62-5.65 (q, J=7.0 Hz, 1H), 5.66-5.71 (dt, J=15.6, 6.8 Hz, 1H), 7.16-7.19 (t, J=7.5 Hz, 3H), 7.21-7.24 (m, 4H), 7.27-7.33 (m, 7H), 7.41-7.42 (d, J=8.2 Hz, 6H), 7.67-7.69 (t, J=7.7 Hz, 1H), 8.80-8.82 (d, J=10.4 Hz, 1H). $^{13}$C NMR (150 MHz, CDCl$_3$): δ 17.1, 19.1, 31.0, 31.6, 32.6, 42.4, 44.2, 56.7, 56.8, 58.0, 60.8, 66.7, 73.0, 121.4, 122.3, 126.6, 127.7, 127.8, 127.9, 128.2, 128.6, 129.6, 133.3, 137.5, 138.0, 144.8, 155.6, 157.2, 169.2, 169.5, 170.6 ppm. HRMS: (ESI) calcd for C$_{47}$H$_{50}$N$_4$O$_4$S [M+H]$^+$ 767.3631. found 767.3608.

Synthesis of Analogue JA4

To a mixture of the cyclized product 55 (73 mg, 0.095 mmol, 1 equiv) and triisopropylsilane (26 mg, 0.143 mmol, 1.5 equiv) in dichloromethane (5 mL) at 0° C. was added trifluoroacetic acid (0.08 g, 0.66 mmol, 30 equiv). The reaction mixture was stirred for 4 h at room temperature. It was concentrated in vacuo, the residue was dried azeotropically with toluene and used in the next step without further purification.

To a stirred solution of the above obtained crude thiol and DMAP (1.0 mg) in dichloromethane (5 mL) at 0° C. was added Hunig's base (39 mg, 0.285 mmol, 3 equiv) and octanoyl chloride (40 mg, 0.24 mmol, 2.5 equiv). The reaction mixture was stirred at room temperature overnight. It was concentrated in vacuo and purified by flash chromatography on silica gel in 20-50% acetone/hexanes to give product JA4 as a colorless oil (37 mg, 60%). $[\alpha]_D^{22}$ −16.6 (c 0.015, CHCl$_3$). $^1$H NMR (600 MHz, CDCl$_3$): δ 0.69-0.70 (d, J=6.8 Hz, 3H), 0.82-0.84 (d, J=6.8 Hz, 3H), 0.88-0.90 (m, 2H), 1.27-1.34 (m, 8H), 1.63-1.68 (quin, J=7.2 Hz, 2H), 2.25-2.30 (m, 1H), 2.31-2.35 (q, J=7.1 Hz, 2H), 2.53-2.56 (t, J=7.5 Hz, 2H), 2.73-2.79 (m, 2H), 2.89-2.91 (t, J=7.4 Hz, 2H), 3.21-3.24 (d, J=17.2 Hz, 1H), 3.44-3.47 (d, J=17.0 Hz, 1H), 3.56-3.58 (d, J=13.8 Hz, 1H), 3.73-3.76 (d, J=13.7 Hz, 1H), 3.78-3.81 (d, J=14.1 Hz, 1H), 3.94-3.96 (d, J=14.1 Hz, 1H), 4.49-4.52 (dd, J=16.9, 3.7 Hz, 1H), 4.67-4.70 (dd, J=16.9, 4.2 Hz, 1H), 4.91-4.94 (dd, J=10.2, 4.2 Hz, 1H), 5.55-5.59 (tdd, J=14.1, 5.1, 1.3 Hz, 1H), 5.68-5.71 (m, 1H), 5.79-5.84 (dtt, J=15.4, 6.8, 0.7 Hz, 1H), 7.18-7.18 (d, J=4.0 Hz, 2H), 7.19-7.20 (d, J=4.2 Hz, 1H), 7.25-7.26 (t, J=3.8 Hz, 1H), 7.28-7.33 (m, 3H), 7.34-7.36 (m, 2H), 7.67-7.70 (t, J=7.5 Hz, 1H), 8.82-8.84 (d, J=10.3 Hz, 1H). $^{13}$C NMR (150 MHz, CDCl$_3$): δ 14.1, 17.1, 19.1, 22.6, 25.7, 27.8, 28.9, 31.6, 32.2, 32.6, 42.4, 44.2, 44.2, 56.7, 56.9, 58.1, 60.8, 73.0, 121.4, 122.3, 127.7, 128.3, 128.4, 128.7, 132.7, 137.6, 138.0, 155.6, 157.3, 169.2, 169.5, 170.6, 199.4 ppm. HRMS: (ESI) calcd for C$_{36}$H$_{50}$N$_4$O$_5$S [M+Na]$^+$ 673.3400. found 673.3412.

Synthesis of (S,E)-methyl 2-(((6-((3-hydroxy-7-(tritylthio)hept-4-enamido)methyl)pyridin-2-yl)methyl)(4-(trifluoromethyl)benzyl)amino)acetate (48)

To a solution of the crude amine product 44 (0.83 g, 2.25 mmol, 1 equiv) in dichloromethane (20 mL) was added DMAP (280 mg, 5.6 mmol, 1 equiv), and Hunig's base (291 mg, 5.6 mmol, 1 equiv). The reaction mixture was stirred at room temperature for 30 min before adding a solution of the aldol product 8 (1.25 g, 5.5 mmol, 1 equiv) in dichloromethane (30 mL). The reaction mixture was stirred at room temperature overnight, concentrated in vacuo, and purified by flash chromatography on silica gel in dichloromethane/ethyl acetate (10-30%) to get 48 as a yellow oil (1.56 g, 90%). [α]$_D^{22}$ −10.6 (c 0.034, CHCl$_3$). $^1$H NMR (600 MHz, CDCl$_3$): δ 2.08-2.12 (q, J=7.3 Hz, 2H), 2.19 (s, 1H), 2.22-2.24 (t, J=7.3 Hz, 2H), 2.40-2.44 (dd, J=15.2, 9.0 Hz, 1H), 2.48-2.51 (dd, J=13.9, 2.9 Hz, 1H), 3.41 (s, 2H), 3.70 (s, 3H), 3.90 (s, 2H), 3.95 (s, 2H), 4.47-4.49 (m, 1H), 4.47-4.51 (dd, J=16.5, 4.8 Hz, 1H), 4.60-4.64 (dd, J=16.5, 5.5 Hz, 1H), 4.45-4.49 (m, 1H), 5.58-5.63 (m, 1H), 7.09 (m, 1H), 7.12-7.13 (d, J=7.5 Hz, 1H), 7.20-7.23 (m, 3H), 7.27-7.30 (m, 6H), 7.40-7.43 (m, 7H), 7.52-7.54 (d, J=8.1 Hz, 2H), 7.58-7.60 (d, J=8.0 Hz, 2H), 7.65-7.67 (t, J=7.7 Hz, 1H). $^{13}$C NMR (150 MHz, CDCl$_3$): δ 31.4, 31.5, 43.1, 44.1, 51.6, 54.3, 57.7, 59.4, 66.6, 69.2, 120.4, 121.6, 125.3, 125.4, 126.6, 127.9, 127.9, 129.0, 129.6, 129.7, 132.5, 137.5, 142.9, 144.9, 155.5, 158.4, 171.6, 172.0 ppm. HRMS: (ESI) calcd for C$_{44}$H$_{44}$F$_3$N$_3$O$_4$S [M+Na]$^+$ 790.2902. found 790.2863.

Synthesis of (R)—((S,E)-1-((6-(((2-methoxy-2-oxoethyl)(4-(trifluoromethyl)benzyl)amino)methyl)pyridin-2-yl)methylamino)-1-oxo-7-(tritylthio)hept-4-en-3-yl) 2-(((9H-fluoren-9-yl)methoxy)carbonylamino)-3-methylbutanoate (52)

To a solution of Fmoc-L-valine (0.70 g, 2.06 mmol, 2 equiv) in THF (10 mL) at 0° C. was added Hunig's base (0.41 g, 3.1 mmol, 3 equiv) and 2,4,6-tricholorobenzoyl chloride (0.52 g, 2.2 mmol, 2.1 equiv). The reaction mixture was stirred for 1 h at 0° C. When TLC showed formation of anhydride, a solution of alcohol 48 (0.79 g, 1.03 mmol, 1 equiv), and DMAP (0.13 g, 1.03 mmol, 1 equiv) in THF (10 mL) was added to the reaction mixture at 0° C. The reaction mixture was stirred at room temperature overnight, concentrated in vacuo and purified by flash chromatography on silica gel in dichloromethane/ethyl acetate (0-20%) followed by a second purification by reversed phase flash chromatography on C$_{18}$ in acetonitrile/water (40-100%) to get 52 as a yellow oil (0.91 g, 81%). [α]$_D^{22}$ −7.5 (c 0.03, CHCl$_3$). $^1$H NMR (600 MHz, CDCl$_3$): δ 0.81-0.83 (d, J=6.7 Hz, 3H), 0.90-0.91 (d, J=6.7 Hz, 3H), 2.05-2.08 (m, 2H), 2.09-2.13 (m, 1H), 2.16-2.21 (m, 2H), 2.56-2.59 (dd, J=14.7, 5.2 Hz, 1H), 2.64-2.67 (dd, J=14.7, 7.9 Hz, 1H), 3.40 (s, 2H), 3.70 (s, 3H), 3.90 (s, 2H), 3.97 (s, 2H), 4.19-4.22 (t, J=7.2 Hz, 2H), 4.31-4.38 (m, 2H), 4.52-4.53 (t, J=5.1 Hz, 2H), 5.68-5.73 (m, 2H), 7.06 (m, 1H), 7.12-7.13 (d, J=7.7 Hz, 1H), 7.21-7.23 (t, J=7.3 Hz, 3H), 7.28-7.31 (m, 7H), 7.32-7.34 (m, 2H), 7.40-7.41 (d, J=7.7 Hz, 7H), 7.43-7.44 (d, J=7.7 Hz, 2H), 7.52-7.53 (d, J=7.7 Hz, 2H), 7.58-7.60 (m, 4H), 7.63-7.66 (t, J=7.7 Hz, 1H), 7.77-7.78 (d, J=7.5 Hz, 2H). $^{13}$C NMR (150 MHz, CDCl$_3$): δ 17.5, 19.0, 31.2, 31.3, 31.4, 41.6, 44.4, 47.1, 51.6, 54.2, 57.7, 58.9, 59.4, 66.6, 67.0, 72.6, 120.0, 120.0, 120.4, 121.4, 125.1, 125.3, 125.4, 126.6, 127.1, 127.1, 127.7, 127.9, 129.0, 129.6, 133.8, 137.5, 141.3, 142.9, 143.8, 143.9, 144.8, 155.5, 156.2, 158.3, 168.7 ppm. HRMS: (ESI) calcd for C$_{64}$H$_{63}$F$_3$N$_4$O$_7$S [M+Na]$^+$ 1111.4267. found 1111.4236.

Synthesis of Cyclic Core of Analogue JA5 (56)

To a solution of 52 (850 mg, 0.78 mmol, 1 equiv) in THF/H$_2$O (4:1, 25 mL) at 0° C. was added 0.1M LiOH (7.8 mL, 0.78 mmol, 1.0 equiv) drop wise over a period of 10 minutes. The reaction mixture was stirred at 0° C. for 1 h. A solution of 0.1M HCl (8.6 mL, 0.86 mmol, 1.1 equiv) was added and the reaction mixture was extracted with ethyl acetate. The combined organic extract was washed with brine, dried over anhydrous sodium sulfate and the solvent evaporated under reduced pressure to give the crude carboxylic acid, which was used in the next step without further purification.

To a solution of the crude carboxylic acid in dichloromethane (35 mL) was added diethylamine (3.6 g, 49.1 mmol, 63 equiv). After stirring at room temperature for 4 h, the reaction mixture was concentrated under reduced pressure and the residue was dried in high vacuum to give the crude product. It was used in the next step without further purification.

To a solution of crude product obtained above, HATU (0.60 g, 1.56 mmol, 2.0 equiv), and HOAt (0.21 g, 1.56 mmol, 2.0 equiv) in dichloromethane (780 mL) was added Hunig's base (0.44 g, 0.34 mmol, 4.4 equiv). After stirring for 3 days at room temperature, the reaction mixture was concentrated in vacuo and diluted with dichloromethane. The dicholormethane solution was washed with brine and evaporated under reduced pressure. The residue was purified by flash chromatography on silica gel in ethyl acetate to give 56 as a yellow oil (280 mg, 43%). [α]$_D^{22}$ +17.1 (c 0.14, CHCl$_3$). $^1$H NMR (600 MHz, CDCl$_3$): δ 0.69-0.71 (d, J=6.8 Hz, 3H), 0.82-0.83 (d, J=6.8 Hz, 3H), 2.03-2.08 (m, 2H), 2.18-2.21 (t, J=7.3 Hz, 2H), 2.27-2.29 (m, 1H), 2.62-2.66 (dd, J=14.7, 9.7 Hz, 1H), 2.75-2.78 (dd, J=14.7, 2.8 Hz, 1H), 3.24-3.27 (d, J=17.1 Hz, 1H), 3.36-3.39 (d, J=17.1 Hz, 1H), 3.65-3.67 (d, J=14.1 Hz, 1H), 3.75-3.80 (m, 2H), 3.92-3.94 (d, J=14.1 Hz, 1H), 4.49-4.53 (dd, J=16.9, 3.8 Hz, 1H), 4.65-4.68 (dd, J=16.9, 4.2 Hz, 1H), 4.89-4.91 (dd, J=10.2, 4.0 Hz, 1H), 5.40-5.43 (dd, J=15.4, 6.4 Hz, 1H), 5.65-5.72 (m, 2H), 7.15-7.19 (m, 3H), 7.20-7.23 (tt, J=6.7, 1.1 Hz, 3H), 7.27-7.30 (t, J=7.3 Hz, 6H), 7.40-7.41 (m, 6H), 7.44-7.45 (m, 2H), 7.54-7.55 (d, J=8.1 Hz, 2H), 7.67-7.69 (t, J=7.5 Hz, 1H), 8.69-8.71 (d, J=10.3 Hz, 1H). $^{13}$C NMR (150 MHz, CDCl$_3$): δ 17.19, 19.11, 31.0, 31.5, 32.6, 42.1, 44.2, 56.9, 57.0, 57.8, 60.7, 66.7, 72.8, 121.6, 122.4, 125.5, 125.6, 126.6, 127.5, 127.9, 128.6, 129.6, 133.6, 137.6, 142.1, 144.8, 155.9, 156.9, 169.1, 169.4, 170.1 ppm. HRMS: (ESI) calcd for $C_{48}H_{49}F_3N_4O_4S$ [M+Na]$^+$ 857.3324. found 857.3349.

Synthesis of Analogue JA5

To a solution of the cyclized product 56 (65 mg, 0.078 mmol, 1 equiv) and triisopropylsilane (21 mg, 0.117 mmol, 1.5 equiv) in dichloromethane (2 mL) at 0° C. was added trifluoroacetic acid (0.24 g, 2.33 mmol, 30 equiv). The reaction mixture was stirred for 4 h at room temperature. It was concentrated in vacuo, and the residue was dried azeotropically with toluene and used in the next step.

To a stirred solution of the above obtained crude thiol and DMAP (3.0 mg, 0.024 mmol) in dichloromethane (2 mL) at 0° C. was added Hunig's base (32 mg, 0.23 mmol, 3 equiv) and octanoyl chloride (32 mg, 0.20 mmol, 2.5 equiv). The reaction mixture was stirred at room temperature overnight, concentrated in vacuo and the residue was purified by flash chromatography on silica gel in 10-50% acetone/hexanes to give product JA5 as a colorless oil (33 mg, 60%). [α]$_D^{22}$ −14.0 (c 0.07, CHCl$_3$). $^1$H NMR (600 MHz, CDCl$_3$): δ 0.69-0.70 (d, J=6.8 Hz, 3H), 0.82-0.84 (d, J=6.8 Hz, 3H), 0.88-0.90 (m, 2H), 1.27-1.34 (m, 8H), 1.63-1.68 (quin, J=7.2 Hz, 2H), 2.25-2.30 (m, 1H), 2.31-2.35 (q, J=7.1 Hz, 2H), 2.53-2.56 (t, J=7.5 Hz, 2H), 2.73-2.79 (m, 2H), 2.89-2.91 (t, J=7.4 Hz, 2H), 3.21-3.24 (d, J=17.2 Hz, 1H), 3.44-3.47 (d, J=17.0 Hz, 1H), 3.56-3.58 (d, J=13.8 Hz, 1H), 3.73-3.76 (d, J=13.7 Hz, 1H), 3.78-3.81 (d, J=14.1 Hz, 1H), 3.94-3.96 (d, J=14.1 Hz, 1H), 4.49-4.52 (dd, J=16.9, 3.7 Hz, 1H), 4.67-4.70 (dd, J=16.9, 4.2 Hz, 1H), 4.91-4.94 (dd, J=10.2, 4.2 Hz, 1H), 5.55-5.59 (tdd, J=14.1, 5.1, 1.3 Hz, 1H), 5.68-5.71 (m, 1H), 5.79-5.84 (dtt, J=15.4, 6.8, 0.7 Hz, 1H), 7.18-7.18 (d, J=4.0 Hz, 2H), 7.19-7.20 (d, J=4.2 Hz, 1H), 7.25-7.26 (t, J=3.8 Hz, 1H), 7.28-7.33 (m, 3H), 7.34-7.36 (m, 2H), 7.67-7.70 (t, J=7.5 Hz, 1H), 8.82-8.84 (d, J=10.3 Hz, 1H). $^{13}$C NMR (150 MHz, CDCl$_3$): δ 14.1, 17.1, 19.1, 22.6, 25.7, 27.8, 28.9, 31.6, 32.2, 32.6, 42.4, 44.2, 44.2, 56.7, 56.9, 58.1, 60.8, 73.0, 121.4, 122.3, 127.7, 128.3, 128.4, 128.7, 132.7, 137.6, 138.0, 155.6, 157.3, 169.2, 169.5, 170.6, 199.4 ppm. HRMS: (ESI) calcd for $C_{37}H_{49}F_3N_4O_5S$ [M+Na]$^+$ 741.3273. found 741.3289.

Synthesis of (S,E)-methyl 2-(((6-((3-hydroxy-7-(tritylthio)hept-4-enamido)methyl)pyridin-2-yl)methyl)(4-methoxybenzyl)amino)acetate (49)

To a solution of the crude amine product 45 (0.36 g, 1.0 mmol, 1 equiv) in dichloromethane (10 mL) was added DMAP (124 mg, 1.0 mmol, 1 equiv) and Hunig's base (130 mg, 1.0 mmol, 1 equiv). The reaction mixture was stirred at room temperature for 30 min before adding a solution of the aldol product 8 (0.56 g, 1.0 mmol, 0.92 equiv) in dichloromethane (15 mL). The reaction mixture was stirred at room temperature overnight, concentrated in vacuo, and the residue was purified by flash chromatography on silica gel in dichloromethane/ethyl acetate (20-50%) to get 49 as yellow oil (0.65 g, 90%). [α]$_D^{22}$ −6.5 (c 0.04, CHCl$_3$). $^1$H NMR (600 MHz, CDCl$_3$): δ 2.07-2.11 (m, 2H), 2.20-2.23 (t, J=7.5 Hz, 2H), 2.41-2.45 (dd, J=9.0, 15.0 Hz, 1H), 2.49-2.52 (dd, J=14.8, 2.7 Hz, 1H), 3.39 (s, 2H), 3.69 (s, 3H), 3.78 (s, 2H), 3.81 (s, 3H), 3.94 (s, 2H), 4.45-4.48 (m, 1H), 4.48-4.51 (dd, J=16.7, 4.6 Hz, 1H), 4.60-4.64 (dd, J=16.5, 5.3 Hz, 1H), 5.44-5.48 (dd, J=15.4, 6.2 Hz, 1H), 5.57-5.63 (dt, J=15.2, 6.8 Hz, 1H), 6.86-6.88 (d, J=8.7 Hz, 2H), 7.11-7.12 (d, J=7.5 Hz, 1H), 7.21-7.23 (t, J=7.2 Hz, 3H), 7.28-7.31 (m, 8H), 7.41-7.42 (d, J=7.9 Hz, 6H), 7.44-7.46 (d, J=7.7 Hz, 1H), 7.65-7.68 (t, J=7.7 Hz, 1H). $^{13}$C NMR (150 MHz, CDCl$_3$): δ 31.4, 31.5, 42.9, 44.1, 51.6, 53.9, 55.3, 57.6, 59.1, 66.5, 69.2, 113.8, 120.4, 121.7, 126.6, 127.9, 129.6, 129.7, 130.2, 132.5, 137.5, 144.9, 155.1, 158.9, 172.1 ppm. HRMS: (ESI) calcd for $C_{44}H_{47}N_3O_5S$ [M+Na]$^+$ 752.3134. found 752.3126.

Synthesis of (R)—((S,E)-1-((6-(((2-methoxy-2-oxo-ethyl)(4-methoxybenzyl)amino)methyl)pyridin-2-yl)methylamino)-1-oxo-7-(tritylthio)hept-4-en-3-yl) 2-(((9H-fluoren-9-yl)methoxy)carbonylamino)-3-methylbutanoate (53)

To a solution of Fmoc-L-valine (0.93 g, 2.8 mmol, 2 equiv) in THF (10 mL) at 0° C. was added Huing's base (0.55 g, 4.2 mmol, 3 equiv) and 2,4,6-tricholorobenzoyl chloride (0.70 g, 2.9 mmol, 2.1 equiv). The reaction mixture was stirred for 1 h at 0° C. When TLC showed formation of anhydride product, alcohol product 49 (1.00 g, 1.4 mmol, 1 equiv) and DMAP (0.17 g, 1.4 mmol, 1 equiv) in THF (20 mL) were added to the reaction mixture at 0° C. The reaction mixture was stirred at room temperature overnight, concentrated in vacuo and purified by flash chromatography on silica gel in dichloromethane/ethyl acetate (20-50%), followed by a second purification by reversed phase chromatography on C$_{18}$ in acetonitrile/water (40-100%) to get 53 as a yellow oil (1.27 g, 86%). [α]$_D^{22}$ +6.25 (c 0.17, CHCl$_3$). $^1$H NMR (600 MHz, CDCl$_3$): δ 0.81-0.82 (d, J=6.8 Hz, 3H), 0.90-0.91 (d, J=6.8 Hz, 3H), 2.04-2.09 (m, 2H), 2.10-2.12 (m, 1H), 2.16-2.21 (m, 2H), 2.57-2.60 (dd, J=14.8, 4.8 Hz, 1H), 2.65-2.68 (m, 1H), 3.38 (s, 2H), 3.69 (s, 3H), 3.80 (s, 5H), 3.95 (s, 2H), 4.19-4.23 (m, 2H), 4.31-4.38 (m, 2H), 4.51 (m, 2H), 5.36-5.38 (d, J=8.8 Hz, 1H), 5.42-5.46 (dd, J=15.4, 7.5 Hz, 1H), 5.68-5.73 (dt, J=15.0, 6.8 Hz, 2H), 6.85-6.87 (d, J=8.6 Hz, 2H), 7.07-7.08 (d, J=7.5 Hz, 1H), 7.20-7.23 (t, J=7.3 Hz, 3H), 7.27-7.33 (m, 12H), 7.39-7.41 (d, J=7.5 Hz, 7H), 7.43-7.44 (d, J=7.6 Hz, 2H), 7.58-7.63 (m, 3H), 7.77-7.78 (d, J=7.4 Hz, 2H). $^{13}$C NMR (150 MHz, CDCl$_3$): δ 17.5, 19.0, 31.1, 31.3, 31.4, 41.6, 44.3, 47.2, 51.5, 53.9, 55.3, 57.6, 59.0, 66.6, 67.0, 72.6, 113.8, 120.0, 120.0, 125.1, 126.6, 127.1, 127.1, 127.7, 127.9, 127.9, 129.6, 129.6, 133.8, 141.3, 143.8, 143.9, 144.8, 155.3, 156.2, 170.9 ppm. HRMS: (ESI) calcd for $C_{64}H_{66}N_4O_8S$ [M+Na]$^+$ 1073.4499. found 1073.4486.

Synthesis of Cyclic Core of JA6 (57)

To a solution of 53 (0.20 g, 0.19 mmol, 1.0 equiv) in THF/H$_2$O (4:1, 5 mL) at 0° C. was added a solution of 0.1M LiOH (1.9 mL, 0.10 mmol, 1.0 equiv) drop wise over a period of 10 minutes. The reaction mixture was stirred at 0° C. for 1 h. A solution of 0.1M HCl (2.1 mL, 0.21 mmol, 1.1 equiv) was added and the reaction mixture was extracted with ethyl acetate. The combined organic extract was washed with brine, dried over anhydrous sodium sulfate and the solvent evaporated under reduced pressure to give the crude carboxylic acid, which was used in the next step without further purification.

To a solution of the crude carboxylic acid in dichloromethane (5 mL) was added diethylamine (1.37 g, 18.2 mmol, 96 equiv). After stirring at room temperature for 4 h, it was concentrated under reduced pressure and the residue was dried in high vacuo to give the crude product. It was used in the next step without further purification.

To the crude product obtained above was added HATU (0.14 g, 0.37 mmol, 2.0 equiv), HOAt (0.049 g, 0.37 mmol, 2.0 equiv), dichloromethane (190 mL) and Hunig's base (0.10 g, 0.81 mmol, 4.4 equiv). After stirring for 3 days at room temperature, the reaction mixture was concentrated in vacuo and diluted with dichloromethane. The dichloromethane solution was washed with brine and the solvent evaporated under reduced pressure. The residue was purified by flash chromatography on silica gel in ethyl acetate to give 57 as a yellow oil (68 mg, 46%). $[\alpha]_D^{22}$ −14.7 (c 0.051, CHCl$_3$). $^1$H NMR (600 MHz, CDCl$_3$): δ 0.67-0.68 (d, J=6.8 Hz, 3H), 0.80-0.82 (d, J=6.8 Hz, 3H), 2.02-2.10 (m, 2H), 2.16-2.22 (m, 3H), 2.23-2.26 (m, 1H), 2.70-2.71 (m, 2H), 3.17-3.20 (d, J=17.1 Hz, 1H), 3.41-3.44 (d, J=17.1 Hz, 1H), 3.49-3.51 (d, J=13.4 Hz, 1H), 3.64-3.66 (d, J=13.4 Hz, 1H), 3.74-3.76 (d, J=13.0 Hz, 1H), 3.76 (s, 3H), 3.87-3.89 (d, J=14.1 Hz, 1H), 4.49-4.52 (dd, J=16.9, 3.6 Hz, 1H), 4.63-4.67 (dd, J=16.9, 3.8 Hz, 1H), 4.86-4.88 (dd, J=10.4, 4.2 Hz, 1H), 5.37-5.41 (dd, J=15.4, 6.6 Hz, 1H), 5.60-5.64 (q, J=6.6 Hz, 1H), 5.67-5.52 (dt, J=15.6, 6.8 Hz, 1H), 6.81-6.83 (d, J=8.5 Hz, 2H), 7.15-7.17 (t, J=8.2 Hz, 2H), 7.20-7.23 (m, 5H), 7.28-7.30 (m, 6H), 7.40-7.41 (d, J=7.5 Hz, 6H), 7.66-7.68 (t, J=7.7 Hz, 1H), 8.74-8.76 (d, J=10.1 Hz, 1H). $^{13}$C NMR (150 MHz, CDCl$_3$): δ 17.2, 19.1, 31.0, 31.6, 32.6, 42.3, 44.2, 55.3, 56.6, 56.9, 57.5, 60.6, 66.7, 73.0, 114.0, 121.3, 122.3, 126.6, 127.7, 127.9, 129.6, 129.8, 133.6, 137.5, 144.8, 155.6, 157.3, 159.1, 169.2, 169.5, 170.7 ppm. HRMS: (ESI) calcd for C$_{48}$H$_{52}$N$_4$O$_5$S [M+Na]$^+$ 819.3556. found 819.3545.

Synthesis of Analogue JA6

To a solution of the cyclized product 57 (35 mg, 0.045 mmol, 1.0 equiv) and triisopropylsilane (12 mg, 0.068 mmol, 1.5 equiv) in dichloromethane (2 mL) at 0° C. was added trifluoroacetic acid (0.164 g, 1.35 mmol, 30 equiv) and the reaction mixture was stirred for 4 h at room temperature. The reaction mixture was concentrated in vacuo, dried azeotropically with toluene and used in the next step.

To a stirred solution of the above obtained crude thiol and DMAP (1.0 mg) in dichloromethane (2 mL) at 0° C. was added Hunig's base (19 mg, 0.135 mmol, 3 equiv) and octanoyl chloride (19 mg, 0.113 mmol, 2.5 equiv). The reaction mixture was stirred at room temperature overnight, concentrated in vacuo and purified by flash chromatography on silica gel in 20-50% acetone/hexanes to give product JA6 as a colorless oil (15 mg, 49%). $[\alpha]_D^{22}$ −5.7 (c 0.056, CHCl$_3$). $^1$H NMR (600 MHz, CDCl$_3$): δ 0.69-0.70 (d, J=7.0 Hz, 3H), 0.82-0.83 (d, J=7.0 Hz, 3H), 0.88-0.91 (t, J=7.1 Hz, 3H) 1.28-1.32 (m, 8H), 1.63-1.66 (m, 2H), 2.25-2.28 (m, 1H), 2.30-2.34 (m, 2H), 2.52-2.55 (t, J=7.7 Hz, 2H), 2.75-2.76 (m, 2H), 2.88-2.90 (dt, J=7.5, 1.1, Hz, 2H), 3.18-3.21 (d, J=17.0 Hz, 1H), 3.44-3.74 (d, J=17.1 Hz, 1H), 3.50-3.52 (d, J=13.4 Hz, 1H), 3.66-3.68 (d, J=13.4 Hz, 1H), 3.76-3.78 (d, J=14.1 Hz, 1H), 3.80 (s, 3H), 3.90-3.93 (d, J=14.1 Hz, 1H), 4.51-4.55 (dd, J=16.9, 3.9 Hz, 1H), 4.65-4.69 (dd, J=16.8, 4.2 Hz, 1H), 4.89-4.91 (dd, J=10.3, 4.2 Hz, 1H), 5.54-5.58 (tdd, J=15.4, 6.4, 1.5 Hz, 1H), 5.67-5.70 (q, J=6.1 Hz, 1H), 5.79-5.84 (dtt, J=0.7, 6.7, 15.5 Hz, 1H), 6.83-6.85 (dd, J=6.6, 2.0 Hz, 1H), 7.16-7.18 (d, J=7.5 Hz, 1H), 7.18-7.20 (d, J=7.8 Hz, 1H), 7.23-7.25 (d, J=8.6 Hz, 2H), 7.29-7.31 (m, 1H), 7.67-7.70 (t, J=7.7 Hz, 1H), 8.77-8.79 (d, J=10.3 Hz, 1H). $^{13}$C NMR (150 MHz, CDCl$_3$): δ 14.1, 17.2, 19.1, 22.6, 25.6, 27.8, 28.9, 31.6, 32.3, 32.6, 42.4, 44.1, 44.2, 55.3, 56.6, 56.9, 57.5, 60.6, 72.9, 114.0, 121.3, 122.3, 128.3, 129.6, 129.8, 132.8, 137.5, 155.6, 157.4, 159.1, 169.2, 169.5, 170.7, 199.3 ppm. HRMS: (ESI) calcd for C$_{37}$H$_{52}$N$_4$O$_6$S [M+Na]$^+$ 703.3505. found 703.3544.

Synthesis of 2-(trimethylsilyl)ethyl 3-bromopropanoate

To a mixture of bromoacetic acid (0.57 g, 4.1 mmol, 2 equiv), N,N-dicyclohexylcarbodiimide (0.95 g, 4 mmol, 2 equivalent), and DMAP (20 mg) in dichloromethane (5 mL) at 0° C. was gradually added 2-ethanoltrimethyl (0.237 g, 2 mmol, 1 equiv). The reaction mixture was stirred overnight at room temperature, concentrated in vacuo. The residue was purified by column chromatography on silica gel in dichloromethane/hexanes (7:3) to get 2-(trimethylsilyl)ethyl 3-bromopropanoate as a colourless oil (382 mg, 80%).

Synthesis of 2-(trimethylsilyl)ethyl(4-chlorobenzyl)glycinate (61)

To a solution of 4-chlorobenzylamine 58 (283 mg, 2 mmol, 2 equiv) in dichloromethane (4 mL) was added 2-(trimethylsilyl)ethyl 3-bromopropanoate (239 mg, 1 mmol, 1 equiv) slowly. The reaction mixture was stirred for 2 h at room temperature, concentrated in vacuo, and purified by column chromatography on silica gel in 10-30% ethyl acetate/hexanes to get 61 as a colorless oil (245 mg, 82%).

Synthesis of 2-(trimethylsilyl)ethyl N-((6-(azidomethyl)pyridin-2-yl)methyl)-N-(4-chlorobenzyl)glycinate (64)

A mixture of the tosylate 33 (636 mg, 2 mmol, 1 equiv), amine 61 (600 mg, 2 mmol, 1 equiv), and sodium carbonate (240 mg, 4 mmol, 2 equiv) in acetonitrile (20 mL) was refluxed under nitrogen for 3 h. When TLC showed disappearance of starting materials, the reaction mixture was cooled to room temperature, treated with water, and extracted three times with ethyl acetate. The organic extract was dried over anhydrous sodium sulfate, filtered, and the solvent was removed under reduced pressure. The residue was purified by flash column chromatography on silica gel in 5-20% ethyl acetate/dichloromethane to get 64 as a yellow oil (0.76 g, 85%).

Synthesis of 2-(trimethylsilyl)ethyl N-((6-(aminomethyl)pyridin-2-yl)methyl)-N-(4-chlorobenzyl)glycinate (67)

To a solution of nitrile 64 (200 mg, 0.45 mmol, 1 equiv) in MeOH (5 mL) and was added 5% Pd/C (20 mg) and the mixture was stirred under hydrogen at 3 atm for 6 h. After disappearance of starting material (TLC), the reaction mixture was filtered through a pad of celite, concentrated in vacuo to get 67 as a yellow oil (185 mg, 99%). It was used in the next step without further purification.

Synthesis of 2-(trimethylsilyl)ethyl(S,E)-N-(4-chlorobenzyl)-N-((6-((3-hydroxy-7-(tritylthio)hept-4-enamido)methyl)pyridin-2-yl)methyl)glycinate (70)

To a solution of the crude amine product 67 (189 mg, 0.45 mmol, 1 equiv) in dichloromethane (5 mL) was added DMAP (56 mg, 0.45 mmol, 1 equiv), and Hunig's base (57 mg, 0.45 mmol, 1 equiv). The reaction mixture was stirred at room temperature for 30 min at room temperature before adding a solution of the aldol product 8 (245 mg, 0.45 mmol, 1 equiv) in dichloromethane (7 mL).

The reaction mixture was stirred for 3 h at room temperature, concentrated in vacuo, and purified by column chromatography on silica gel in 50% ethyl acetate/hexanes to get 70 as a yellow oil (295 mg, 80%). ¹H NMR (600 MHz, CDCl₃): δ 0.032 (s, 9H), 0.98 (t, 2H), 2.08-2.12 (q, J=7.3 Hz, 2H), 2.20-2.21 (t, J=7.3 Hz, 2H), 2.40-2.44 (dd, J=15.2, 9.0 Hz, 1H), 2.48-2.51 (dd, J=13.9, 2.9 Hz, 1H), 3.41 (s, 2H), 3.70 (s, 3H), 3.90 (s, 2H), 3.95 (s, 2H), 4.47-4.49 (m, 1H), 4.47-4.51 (dd, J=16.5, 4.8 Hz, 1H), 4.60-4.64 (dd, J=16.5, 5.5 Hz, 1H), 4.45-4.49 (m, 1H), 5.58-5.63 (m, 1H), 7.09 (m, 1H), 7.12-7.13 (d, J=7.5 Hz, 1H), 7.20-7.23 (m, 3H), 7.27-7.30 (m, 6H), 7.40-7.43 (m, 7H), 7.52-7.54 (d, J=8.1 Hz, 2H), 7.58-7.60 (d, J=8.0 Hz, 2H), 7.65-7.67 (t, J=7.7 Hz, 1H). ¹³C NMR (150 MHz, CDCl₃): δ 1.5, 17.5, 31.4, 31.5, 43.0, 44.1, 54.5, 57.5, 59.4, 62.9, 66.6, 69.2, 120.4, 121.6, 126.6, 127.9, 128.5, 129.6, 129.7, 130.3, 132.5, 133.0, 137.1, 137.4, 144.9, 155.3, 158.7, 171.5, 172.0 ppm.

Synthesis of (S,E)-1-(((6-(((4-chlorobenzyl)(2-oxo-2-(2-(trimethylsilyl)ethoxy)ethyl)amino)methyl)pyridin-2-yl)methyl)amino)-1-oxo-7-(tritylthio)hept-4-en-3-yl)(((9H-fluoren-9-yl)methoxy)carbonyl)-D-valinate (73)

To a solution of Fmoc-L-valine (184 mg, 0.54 mmol, 2 equiv) in THF (3 mL) at 0° C. was added Hunig's base (90 mg, 0.675 mmol, 2.5 equiv) and 2,4,6-tricholorobenzoyl chloride (140 m g, 0.57 mmol, 2.1 equiv). The reaction mixture was stirred for 1 h at 0° C. When TLC showed the formation of anhydride product, a solution of alcohol 70 (221 m g, 0.27 mmol, 1 equiv) and DMAP (34 mg, 0.27 mmol, 1 equiv) in THF (5 mL) was added to the reaction mixture at the same temperature. The reaction mixture was stirred at room temperature overnight, concentrated in vacuo, and purified by flash chromatography on silica gel in ethyl acetate/dichloromethane (10-30%) to get 73 as a white fluffy powder (0.25 g, 85%). ¹H NMR (600 MHz, CDCl₃): δ 0.03-0.04 (s, 9H), 0.80-0.82 (d, J=7.2 Hz, 3H), 0.88-0.90 (d, J=6.6 Hz, 2H), 0.96-1.00 (t, J=8.4, 2H), 2.16-2.18 (m, 3H), 2.24-2.28 (m, 2H), 2.56-2.65 (m, 2H), 3.32 (s, 2H), 3.78 (s, 2H), 3.91 (s, 2H), 3.17-3.24 (m, 4H), 4.30-4.34 (m, 2H), 4.48-4.50 (t, J=3.6 Hz, 2H), 5.38-5.44 (m, 2H), 5.67-5.72 (m, 2H), 6.97 (m, 1H), 7.04-7.06 (d, J=7.8 Hz, 1H), 7.18-7.21 (t, J=7.2 Hz, 1H), 7.27-7.33 (m, 13H), 7.37-7.42 (m, 9H), 7.56-7.60 (m, 3H), 7.74-7.76 (d, J=8.4 Hz, 2H). ¹³C NMR (150 MHz, CDCl₃): δ 1.5, 17.3, 17.5, 19.0, 31.1, 31.3, 31.4, 41.5, 44.4, 47.2, 54.5, 57.0, 58.9, 59.5, 62.8, 66.8, 67.0, 72.5, 120.0, 120.0, 120.2, 121.4, 125.1, 126.6, 127.1, 127.1, 127.7, 127.9, 128.5, 129.6, 130.2, 132.9, 133.9, 137.2, 137.4, 141.3, 143.8, 143.9, 144.8, 168.7, 171.0, 171.4 ppm.

Synthesis of N-((6-(((S,E)-3-((L-valyl)oxy)-7-(tritylthio)hept-4-enamido)methyl)pyridin-2-yl)methyl)-N-(4-chlorobenzyl)glycine (76)

To a solution of 73 (171 mg, 0.15 mmol, 1 equiv) in THF (70 mL) at 0° C. was added TBAF. The reaction mixture was stirred for 2 h at room temperature, concentrated in vacuo, and the residue was partitioned between EtOAc and water. The combined organic extract was washed with brine, dried over Na₂SO₄, filtered, and concentrated in vacuo, washed with hexane 5 times to give a yellow residue which was used in the next step without further purification.

Synthesis of Cyclic Core of Analogue AA1 (79)

To a solution of 76 (28 mg, 0.034 mmol, 1 equiv), HATU (26 mg, 0.068 mmol, 2.0 equiv), and HOAt (10 mg, 0.068 mmol, 2.0 equiv) in dichloromethane (30 mL) was added Hunig's base (21 mg, 0.15 mmol, 4.4 equiv). The reaction mixture was stirred overnight at room temperature, concentrated in vacuo. The residue was purified by flash chromatography on silica gel in acetone/hexanes (5-30%), followed by a second purification by reversed phase chromatography on C₁₈ in acetonitrile/water (60-100%) to give 79 as a colourless oil (16 mg, 60%). ¹H NMR (600 MHz, CDCl₃): δ 0.65-0.67 (d, J=6.8 Hz, 3H), 0.79-0.81 (d, J=6.8 Hz, 3H), 2.02-2.06 (m, 2H), 2.18-2.21 (t, J=7.3 Hz, 2H), 2.27-2.29 (m, 1H), 2.62-2.65 (dd, J=14.7, 9.7 Hz, 1H), 2.71-2.75 (dd, J=14.7, 2.8 Hz, 1H), 3.17-3.21 (d, J=17.1 Hz, 1H), 3.34-3.37 (d, J=17.1 Hz, 1H), 3.51-3.54 (d, J=14.1 Hz, 1H), 3.64-3.66 (d, J=14.1 Hz, 1H), 3.73-3.75 (d, J=14.1 Hz, 1H), 3.86-3.89 (d, J=14.1 Hz, 1H), 4.48-4.50 (dd, J=16.9, 3.8 Hz, 1H), 4.61-4.64 (dd, J=16.9, 4.2 Hz, 1H), 4.86-4.89 (dd, J=10.2, 4.0 Hz, 1H), 5.37-5.41 (dd, J=15.4, 6.4 Hz, 1H), 5.60-5.71 (m, 2H), 7.14-7.16 (d, J=7.5 1H), 7.17-7.19 (d, J=7.7 Hz, 1H), 7.20-7.23 (t, J=1.2, 3H), 7.23-7.24 (t, J=5.2, 1H), 7.25-7.29 (m, 4H), 7.30-7.32 (t, J=7.3 Hz, 6H), 7.40-7.42 (tt, J=1.4, 6H), 7.65-7.69 (t, J=7.5 Hz, 1H), 8.68-8.71 (d, J=10.3 Hz, 1H). ¹³C NMR (150 MHz, CDCl₃): δ 17.19, 19.10, 31.0, 31.6, 38.6, 42.2, 44.2, 56.8, 56.9, 57.5, 60.6, 66.7, 72.9, 121.5, 122.3, 121.5, 122.3, 126.6, 127.3, 127.5, 128.8, 129.8, 133.4, 133.5, 136.4, 137.6, 144.8, 155.7, 157.0, 169.1, 169.4, 170.2 ppm.

Synthesis of Analogue AA1

To a mixture of 79 (13 mg, 0.016 mmol, 1 equiv) and triisopropylsilane (7 mg, 0.04 mmol, 2.5 equiv) in dichloromethane (0.5 mL) at 0° C. was added trifluoroacetic acid (0.15 g, 1.23 mmol, 77 equiv). The reaction mixture was stirred for 3 h at room temperature. It was concentrated in vacuo, the residue was dried azeotropically with toluene and used in the next step without further purification.

To a stirred solution of the above obtained crude thiol and DMAP (1.0 mg) in dichloromethane (0.5 mL) at 0° C. was added Hunig's base (12 mg, 0.08 mmol, 5 equiv) and octanoyl chloride (11 mg, 0.064 mmol, 4 equiv). The reaction mixture was stirred at room temperature overnight. It was concentrated in vacuo and purified by flash chromatography on silica gel in 10-40% acetone/hexanes, followed by a second purification by reversed phase chromatography on C₁₈ in acetonitrile/water (40-90%) to give product AA1 as a colorless oil (6 mg, 68%). ¹H NMR (600 MHz, CDCl₃): δ 0.70-0.71 (d, J=6.8 Hz, 3H), 0.83-0.84 (d, J=6.8 Hz, 3H), 0.89-0.90 (m, 2H), 1.27-1.33 (m, 8H), 1.64-1.68 (quin, J=7.2 Hz, 2H), 2.33-2.34 (m, 1H), 2.35-2.36 (q, J=7.1 Hz, 2H), 2.53-2.56 (t, J=7.5 Hz, 2H), 2.70-2.79 (m, 2H), 2.89-2.91 (t, J=7.4 Hz, 2H), 3.22-3.25 (d, J=17.2 Hz, 1H), 3.40-3.43 (d, J=17.0 Hz, 1H), 3.57-3.59 (d, J=13.8 Hz, 1H), 3.70-3.72 (d, J=13.7 Hz, 1H), 3.79-3.81 (d, J=14.1 Hz, 1H), 3.93-3.96 (d, J=14.1 Hz, 1H), 4.53-4.54 (dd, J=16.9, 3.7 Hz, 1H), 4.65-4.67 (dd, J=16.9, 4.2 Hz, 1H), 4.91-4.94 (dd, J=10.2, 4.2 Hz, 1H), 5.56-5.60 (tdd, J=14.1, 5.1, 1.3 Hz, 1H), 5.68-5.71 (m, 1H), 5.79-5.83 (dtt, J=15.4, 6.8, 0.7 Hz, 1H), 7.17-7.18 (d, J=4.0 Hz, 1H), 7.19-7.20 (d, J=4.2 Hz, 1H), 7.20-7.24 (t, J=3.8 Hz, 1H), 7.26-7.33 (m, 4H), 7.68-7.70 (t, J=7.5 Hz, 1H), 8.73-8.75 (d, J=10.3 Hz, 1H). ¹³C NMR (150 MHz, CDCl₃): δ 14.1, 17.2, 19.1, 22.6, 25.7, 27.8, 28.9, 31.6, 32.3, 32.6, 42.3, 44.1, 56.8, 56.9, 57.5, 60.7, 72.8, 121.5, 122.4, 128.3, 128.8, 129.6, 132.7, 133.4, 136.5, 137.6, 155.7, 157.0, 169.1, 169.4, 170.3, 199.3 ppm.

Synthesis of 2-(trimethylsilyl)ethyl(naphthalen-1-ylmethyl)glycinate (62)

To a solution of 1-naphthylmethylamine 59 (320 mg, 2 mmol, 2 equiv) in dichloromethane (4 mL) was added trimethylsilylethanebromoacetate ester (239 mg, 1 mmol, 1 equiv) slowly. The reaction mixture was stirred for 2 h at room temperature, concentrated in vacuo, and purified by flash chromatography on silica gel in 10-30% ethyl acetate/hexanes to get 62 as a colorless oil (240 mg, 77%).

Synthesis of 2-(trimethylsilyl)ethyl N-((6-(azidomethyl)pyridin-2-yl)methyl)-N-(naphthalen-1-ylmethyl)glycinate (65)

A mixture of the tosylate 33 (382 mg, 1.25 mmol, 1 equivalent), amine 62 (395 mg, 1.25 mmol, 1 equivalent), and sodium carbonate (180 mg, 2.5 mmol, 2 equivalent) in acetonitrile (20 mL) was refluxed under nitrogen for 3 h. When TLC showed disappearance of starting materials, the reaction mixture was cooled to room temperature, treated with water, and extracted three times with ethyl acetate. The organic extract was dried over anhydrous sodium sulfate, filtered and solvent removed under reduced pressure. The residue was purified by flash column chromatography on silica gel in 5-20% ethyl acetate/dichloromethane to get 65 as a yellow oil (550 mg, 95%).

Synthesis of 2-(trimethylsilyl)ethyl N-((6-(aminomethyl)pyridin-2-yl)methyl)-N-(naphthalen-1-ylmethyl)glycinate (68)

To a solution of nitrile 65 (512 mg, 1.1 mmol, 1 equiv) in MeOH (12 mL) was added 5% Pd/C (50 mg) and the mixture was stirred under hydrogen at 3 atm for 10 h. After disappearance of starting material (TLC), the reaction mixture was filtered through a pad of celite, concentrated in vacuo to get 68 as a yellow oil (430 mg, 90%). It was used in the next step without further purification.

Synthesis of 2-(trimethylsilyl)ethyl(S,E)-N-((6-((3-hydroxy-7-(tritylthio)hept-4-enamido)methyl)pyridin-2-yl)methyl)-N-(naphthalen-1-ylmethyl)glycinate (71)

To a solution of the crude amine product 68 (190 mg, 0.44 mmol, 1 equiv) in dichloromethane (5 mL) was added DMAP (55 mg, 0.44 mmol, 1 equiv), and Hunig's base (55 mg, 0.44 mmol, 1 equiv). The reaction mixture was stirred at room temperature for 30 min at room temperature before adding a solution of the aldol product 8 (245 mg, 0.44 mmol, 1 equiv) in dichloromethane (10 mL). The reaction mixture was stirred for 3 h at room temperature, concentrated in vacuo, and purified by passing through a pad of silica gel in 60% ethyl acetate/hexanes to get 71 as a yellow oil (305 mg, 84%).

Synthesis of (S,E)-1-(((6-(((naphthalen-1-ylmethyl)(2-oxo-2-(2-(trimethylsilyl)ethoxy)ethyl)amino)methyl)pyridin-2-yl)methyl)amino)-1-oxo-7-(tritylthio)hept-4-en-3-yl(((9H-fluoren-9-yl)methoxy)carbonyl)-D-valinate (74)

To a solution of Fmoc-L-valine (175 mg, 0.5 mmol, 2 equiv) in THF (7 mL) at 0° C. was added Hunig's base (0.1 g, 0.75 mmol, 3 equiv) and 2,4,6-tricholorobenzoyl chloride (133 mg, 0.53 mmol, 2.1 equiv). The reaction mixture was stirred for 1 h at 0° C. When TLC showed the formation of anhydride product, a solution of alcohol 71 (215 mg, 0.26 mmol, 1 equiv) and DMAP (33 mg, 0.26 mmol, 1 equiv) in THF (20 mL) was added to the reaction mixture at the same temperature. The reaction mixture was stirred at room temperature overnight, concentrated in vacuo, and purified by flash chromatography on silica gel in acetone/hexanes (10-50%) to give 74 as a colourless oil (0.22 g, 93%). $^1$H NMR (600 MHz, CDCl$_3$): δ 0.02-0.03 (s, 9H), 0.81-0.83 (d, J=6.8 Hz, 3H), 0.89-0.91 (d, J=6.6 Hz, 2H), 0.97-1.01 (t, J=7.3 Hz, 2H), 2.04-2.07 (m, 3H), 2.18-2.20 (m, 2H), 2.53-2.63 (m, 2H), 3.39 (s, 2H), 4.02 (s, 2H), 4.17-4.21 (m, 4H), 3.31-3.36 (m, 4H), 4.48-4.50 (t, J=3.6 Hz, 2H), 5.35-5.43 (m, 2H), 5.67-5.72 (m, 2H), 6.97 (m, 1H), 7.01-7.04 (d, J=7.6 Hz, 1H), 7.18-7.21 (t, J=7.2 Hz, 3H), 7.27-7.34 (m, 11H), 7.38-7.42 (m, 9H), 7.47-7.53 (m, 5H), 7.70-7.76 (m, 3H), 7.82-7.85 (d, J=16.2, 1H), 8.41-8.43 (d, J=8.2, 1H). $^{13}$C NMR (150 MHz, CDCl$_3$): δ 1.5, 17.5, 17.7, 19.0, 31.2, 31.3, 31.4, 41.6, 44.4, 47.2, 54.5, 57.4, 58.9, 59.5, 62.8, 66.8, 67.0, 72.6, 119.9, 120.0, 120.4, 122.6, 124.9, 125.1, 125.2, 125.7, 125.9, 126.6, 127.1, 127.7, 127.9, 128.4, 129.6 132.5, 133.8, 141.3, 143.8, 143.9, 144.8, 156.2, 168.6, 171.1, 171.6 ppm.

Synthesis of N-((6-(((S,E)-3-((L-valyl)oxy)-7-(tritylthio)hept-4-enamido)methyl)pyridin-2-yl)methyl)-N-(naphthalen-1-ylmethyl)glycine (77)

To a solution of 74 (200 mg, 0.13 mmol, 1 equiv) in THF (80 mL) at 0° C. was added TBAF. The reaction mixture was stirred for 2 h at room temperature, concentrated in vacuo, and partitioned between EtOAc and water. The combined organic extract was washed with brine, dried over Na$_2$SO$_4$, filtered, and concentrated in vacuo, washed with hexane 5 times to give yellow residue which was used in the next step without further purification.

Synthesis of Cyclic Core of Analogue AA2 (80)

To a solution of 77 (45 mg, 0.056 mmol, 1 equiv), HATU (45 mg, 0.112 mmol, 2.0 equiv), and HOAt (17 m g, 0.112 mmol, 2.0 equiv) in dichloromethane (40 mL) was added Hunig's base (35 mg, 0.25 mmol, 4.4 equiv). The reaction mixture was stirred overnight at room temperature, concentrated in vacuo. The residue was purified by flash chromatography on silica gel in acetone/hexanes (5-25%), followed by a second purification by reversed phase chromatography on C$_{18}$ in acetonitrile/water (40-100%) to give 80 as a colourless oil (19 mg, 45%). $^1$H NMR (600 MHz, CDCl$_3$): δ 0.46-0.49 (d, J=6.6 Hz, 3H), 0.66-0.69 (d, J=6.7 Hz, 3H), 1.96-1.98 (m, 2H), 2.07-2.10 (m, 1H), 2.14-2.17 (t, J=7.5 Hz, 2H), 2.41-2.45 (d, J=9.2, 1H), 2.58-2.62 (d, J=12.7 Hz, 1H), 3.36-3.39 (d, J=17.2 Hz, 1H), 3.52-3.55 (d, J=17.6 Hz, 1H), 3.86-3.89 (d, J=13.7 Hz, 1H), 3.94-3.97 (d, J=14.0 Hz, 1H), 4.13-4.16 (d, J=13.7 Hz, 1H), 4.50-4.54 (dd, J=3.1, 3.0 Hz, 1H), 4.60-4.64 (dd, J=3.6, 3.9 Hz, 1H), 4.79-4.82 (dd, J=4.1, 4.0 Hz, 1H), 5.25-5.29 (d, J=6.4 Hz, 1H), 5.53-5.61 (m, 2H), 7.10-7.14 (d, J=7.5 1H), 7.16-7.18 (d, J=7.8 Hz, 1H), 7.18-7.20 (t, J=7.6, 1H), 7.20-7.22 (t, J=1.2, 3H), 7.28-7.33 (m, 8H), 7.35-7.45 (m, 10H), 7.54-7.52 (d, J=6.8, 1H), 7.66-7.70 (m, 3H), 7.78-7.80 (d, J=8.1 Hz, 1H), 8.47-8.50 (d, J=9.2 Hz, 1H). $^{13}$C NMR (150 MHz, CDCl$_3$): δ 17.10, 18.9, 30.9, 31.4, 32.3, 41.9, 44.2, 56.2, 56.9, 57.5, 62.1, 66.7, 72.5, 121.4, 122.6, 123.3, 125.3, 125.7, 126.2, 126.7, 127.5, 127.9, 128.5, 129.0, 129.7, 131.9, 133.0, 133.4, 133.8, 137.5, 144.8, 155.7, 157.1, 169.3, 169.4, 170.6 ppm.

Synthesis of Analogue AA2

To a mixture of 80 (15 mg, 0.018 mmol, 1 equiv) and triisopropylsilane (7 mg, 0.045 mmol, 1.5 equiv) in dichloromethane (0.5 mL) at 0° C. was added trifluoroacetic acid (0.168 g, 1.386 mmol, 77 equiv). The reaction mixture was stirred for 3 h at room temperature. It was concentrated in vacuo, the residue was dried azeotropically with toluene and used in the next step without further purification.

To a stirred solution of the above obtained crude thiol and DMAP (1.0 mg) in dichloromethane (0.5 mL) at 0° C. was added Hunig's base (13 mg, 0.09 mmol, 5 equiv) and octanoyl chloride (12 mg, 0.072 mmol, 4 equiv). The reaction mixture was stirred at room temperature overnight. It was concentrated in vacuo and purified by flash chromatography on silica gel in 10-40% acetone/hexanes, followed by a second purification by reversed phase chromatography on $C_{18}$ in acetonitrile/water (40-90%) to give product AA2 as a colorless oil (6 mg, 65%). $^1$H NMR (600 MHz, CDCl$_3$): δ 0.47-0.48 (d, J=6.8 Hz, 3H), 0.67-0.69 (d, J=6.8 Hz, 3H), 0.88-0.89 (m, 2H), 1.28-1.33 (m, 8H), 1.64-1.67 (quin, J=7.2 Hz, 2H), 2.05-2.10 (m, 1H), 2.20-2.22 (q, J=7.1 Hz, 2H), 2.45-2.49 (m, 1H), 2.52-2.54 (t, J=7.5 Hz, 2H), 2.61-2.63 (d, J=9.3 Hz, 1H), 2.77-2.80 (t, J=7.4 Hz, 2H), 3.37-3.40 (d, J=17.0 Hz, 1H), 3.53-3.55 (d, J=13.8 Hz, 1H), 3.90-3.92 (d, J=13.7 Hz, 1H), 3.91-3.95 (d, J=14.1 Hz, 1H), 3.97-3.99 (d, J=14.1 Hz, 1H), 4.12-4.14 (d, J=14.1 Hz, 1H), 4.57-4.59 (dd, J=16.9, 3.7 Hz, 1H), 4.60-4.61 (dd, J=16.9, 4.2 Hz, 1H), 4.79-4.81 (dd, J=10.2, 4.2 Hz, 1H), 5.41-5.43 (tdd, J=14.1, 5.1, 1.3 Hz, 1H), 5.57-5.59 (m, 1H), 5.68-5.71 (dtt, J=15.4, 6.8, 0.7 Hz, 1H), 7.13-7.16 (t, J=4.0 Hz, 1H), 7.17-7.20 (d, J=4.2 Hz, 1H), 7.21-7.23 (d, J=3.8 Hz, 1H), 7.34-7.36 (t, J=4.0 Hz, 1H), 7.36-7.39 (t, J=4.2 Hz, 1H), 7.42-7.46 (t, J=3.8 Hz, 1H), 7.51-7.53 (d, J=7.5 Hz, 1H), 7.67-7.70 (t, J=4.0 Hz, 1H), 7.71-7.73 (d, J=4.2 Hz, 1H), 7.76-7.78 (d, J=3.8 Hz, 1H), 7.82-7.84 (d, J=7.5 Hz, 1H), 8.48-8.52 (d, J=10.3 Hz, 1H). $^{13}$C NMR (150 MHz, CDCl$_3$): δ 14.1, 17.1, 18.9, 22.6, 25.7, 27.8, 28.9, 31.6, 32.3, 32.6, 41.9, 44.2, 56.3, 56.9, 57.5, 62.1, 72.4, 121.4, 122.5, 123.3, 125.3, 125.8, 126.3, 127.2, 128.0, 128.6, 129.0, 131.9, 132.4, 133.4, 133.9, 137.5, 155.7, 157.1, 169.3, 169.4, 170.6, 199.3 ppm.

Alternative Procedure for Synthesis of JA2

Synthesis of 6'-cyano-2,2'-bipyridine-6-carboxylic acid (82)

To a solution of 25 (25 mg, 0.10 mmol, 1 equiv) in THF/H$_2$O (4:1, 1 mL) at 0° C. was added 0.1M LiOH (1.0 mL, 0.10 mmol, 1.0 equiv) dropwise over a period of 10 minutes. The reaction mixture was stirred at 0° C. for another 1 h, treated with 1M HCl solution and extracted with ethyl acetate (3×2 mL). The organic extract was washed with brine, dried over anhydrous sodium sulfate and solvent evaporated under reduced pressure to give the crude carboxylic acid 82, which was used in the next step without further purification. $^1$H NMR (600 MHz, MeOD): δ 8.15-8.21 (m, 3H), 8.26-8.29 (t, J=8.1 Hz, 1H), 8.56-8.58 (dd, J=7.4, 1.5 Hz, 1H), 8.82-8.83 (dd, J=8.2, 1.1 Hz, 1H). $^{13}$C NMR (150 MHz, MeOD): δ 117.9, 124.4, 125.4, 126.2, 130.1, 132.8, 139.8, 140.0, 148.8, 153.7, 156.5, 166.3 ppm.

Synthesis of 2-(trimethylsilyl)ethyl 6'-cyano-2,2'-bipyridine-6-carboxylate (83)

To a solution of carboxylic acid 82 (225 mg, 1 mmol, 1 equiv), DMAP (122 mg, 1 mmol, 1 equiv), and trimethylsilylethanol (142 mg, 1.2 mmol, 1.2 equiv) in 30 ml of dry DCM was added DCC. The resulting reaction mixture was stirred at room temperature under nitrogen for overnight, concentrated in vacuo, and purified by flash chromatography on silica gel in ethyl acetate/DCM to get 83 as a yellow oil (2.16 g, 76%). $^1$H NMR (600 MHz, CDCl$_3$) δ 0.13 (s, 9H), 1.21-1.24 (t, J=8.3 Hz, 2H), 4.42 (bs, 2H), 4.54-4.57 (t, J=8.3 Hz, 2H), 7.50-7.51 (d, J=7.7 Hz, 1H), 7.98-8.01 (t, J=7.7 Hz, 1H), 8.08-8.11 (t, J=7.8 Hz, 1H), 8.16-8.17 (d, J=7.5 Hz, 1H), 8.55-8.56 (d, J=7.9 Hz, 1H), 8.78-8.79 (d, J=7.9 Hz, 1H).

Synthesis of 2-(trimethylsilyl)ethyl 6'-(aminomethyl)-2,2'-bipyridine-6-carboxylate (84)

To a mixture of nitrile 83 (1.27 g, 3.9 mmol) in MeOH (15 mL) and trifluoroacetic acid (1 mL) was added 5% Pd/C (91 mg, 5 wt %). The reaction mixture was stirred under hydrogen at 3 atm for overnight. After disappearance of starting material (TLC), the reaction mixture was filtered through a pad of celite to remove palladium catalyst and concentrated under reduced pressure. The product 84 (1.28 g, 98% yield) was used in the next step with no further purification. $^1$H NMR (600 MHz, CDCl$_3$): δ 0.14 (s, 9H), 1.23-1.25 (t, J=8.2 Hz, 1H), 4.54-4.57 (t, J=8.4 Hz, 2H), 7.75-7.76 (dd, J=7.5, 0.9 Hz, 1H), 7.99-8.02 (t, J=7.9 Hz, 1H), 8.02-8.04 (t, J=6.2 Hz, 1H), 8.19-8.20 (dd, J=7.7, 1.1 Hz, 1H), 8.67-8.68 (dd, J=7.9, 0.9 Hz, 1H), 8.84-8.86 (dd, J=8.0, 0.9 Hz, 1H). $^{13}$C NMR (150 MHz, CDCl$_3$): δ 1.4, 17.4, 64.39, 117.3, 124.5, 124.9, 125.9, 128.6, 133.2, 138.1, 138.3, 148.2, 154.2, 156.9, 165.2 ppm.

Synthesis of (S,E)-2-(trimethylsilyl)ethyl 6'-((3-hydroxy-7-(tritylthio)hept-4-enamido)methyl)-2,2'-bipyridine-6-carboxylate (85)

To a solution of the above obtained crude amine product 84 (1.28 g, 3.9 mmol, 1 equiv) in dichloromethane (20 mL) was added DMAP (480 mg, 3.9 mmol, 1 equiv), and Hunig's base (507 mg, 3 mmol, 1 equiv). The reaction mixture was stirred at room temperature for 30 min before adding a solution of aldol product 8 (2.18 g, 3.9 mmol, 1 equiv) in dichloromethane (40 mL). The reaction mixture was stirred at room temperature overnight, concentrated in vacuo, and purified by flash chromatography on silica gel in ethyl acetate get 85 as a yellow oil (2.16 g, 76%).

Synthesis of 2-(trimethylsilyl)ethyl 6'-((5R,8S)-1-(9H-fluoren-9-yl)-5-isopropyl-3,6,10-trioxo-8-((E)-4-(tritylthio)but-1-enyl)-2,7-dioxa-4,11-diazadodecan-12-yl)-2,2'-bipyridine-6-carboxylate (86)

To a solution of Fmoc-L-valine (1.31 g, 3.84 mmol, 2 equiv) in THF (25 mL) at 0° C. was added Hunig's base (749 mg, 5.76 mmol, 3 equiv) and 2,4,6-tricholorobenzoyl chloride (976 mg, 4.03 mmol, 2.1 equiv). The reaction mixture was stirred for 1 h at 0° C. When TLC showed the formation of anhydride, a solution of alcohol 85 (1.40 g, 1.92 mmol, 1 equiv), and DMAP (234 mg, 1.92 mmol, 1 equiv) in THF (15 mL) was added to the reaction mixture at 0° C. The reaction mixture was stirred at room temperature overnight, concentrated in vacuo, and purified by flash chromatography on silica gel in ethyl acetate/hexanes (50-70%), followed by a second purification by reversed phase chromatography on $C_{18}$ in acetonitrile/water (40-100%) to get 86 as a yellow oil (1.75 mg, 87%).

Example 2

Biological Evaluation of Analogues JA1-JA6, AA1-AA2, and RF1

Figure 22A:
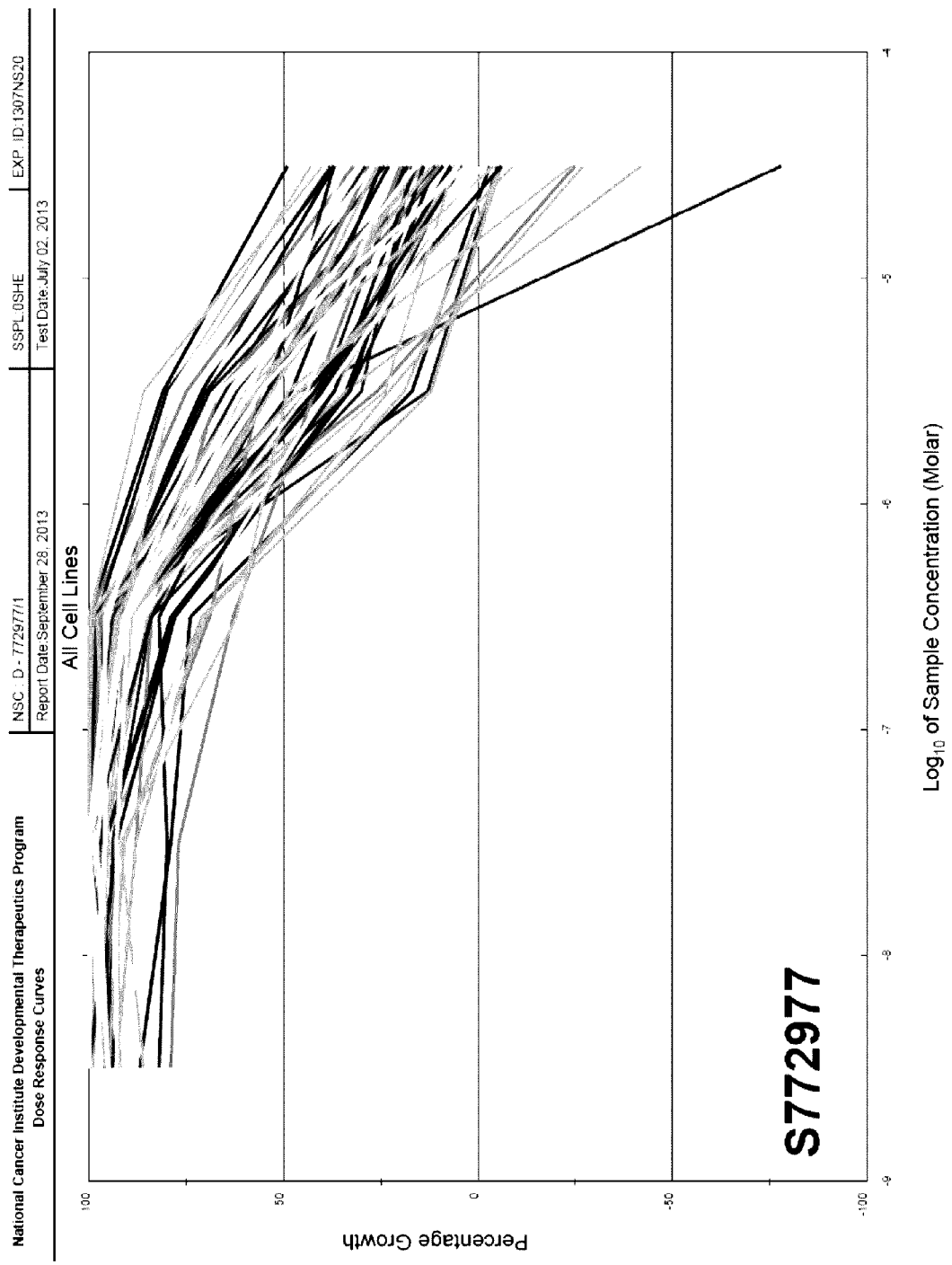
Figure 22B:
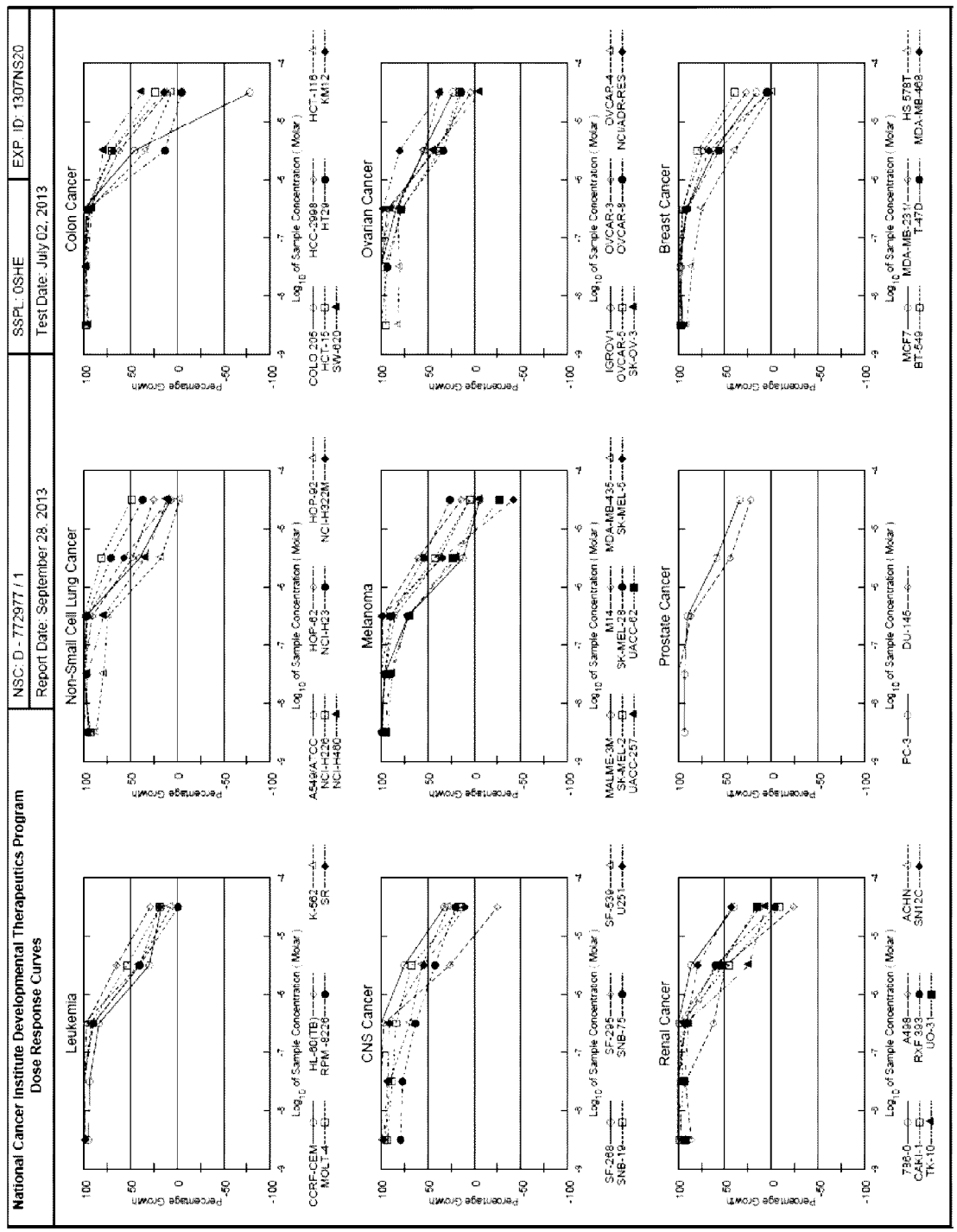
Figure 22D:
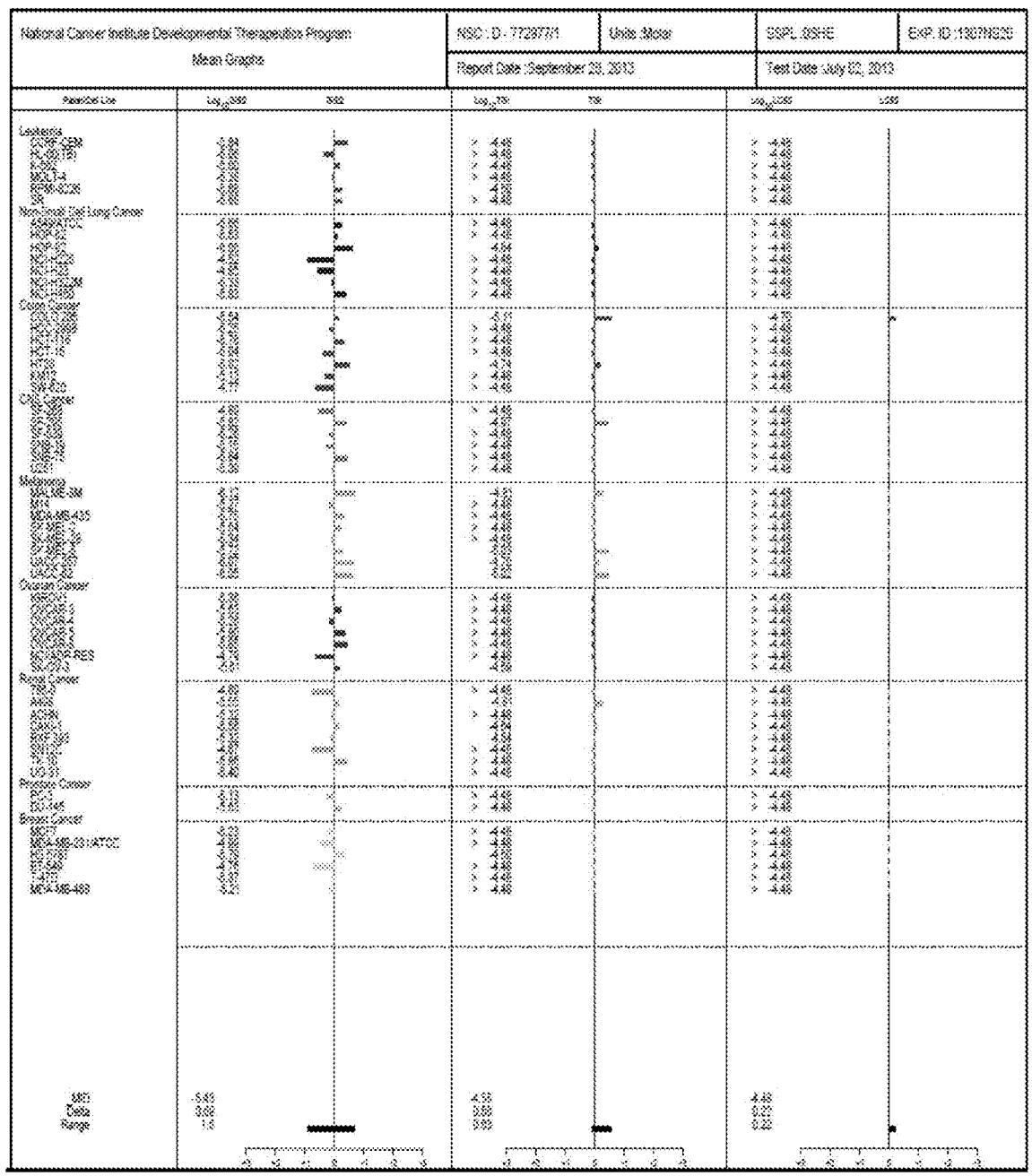
Figure 23A:
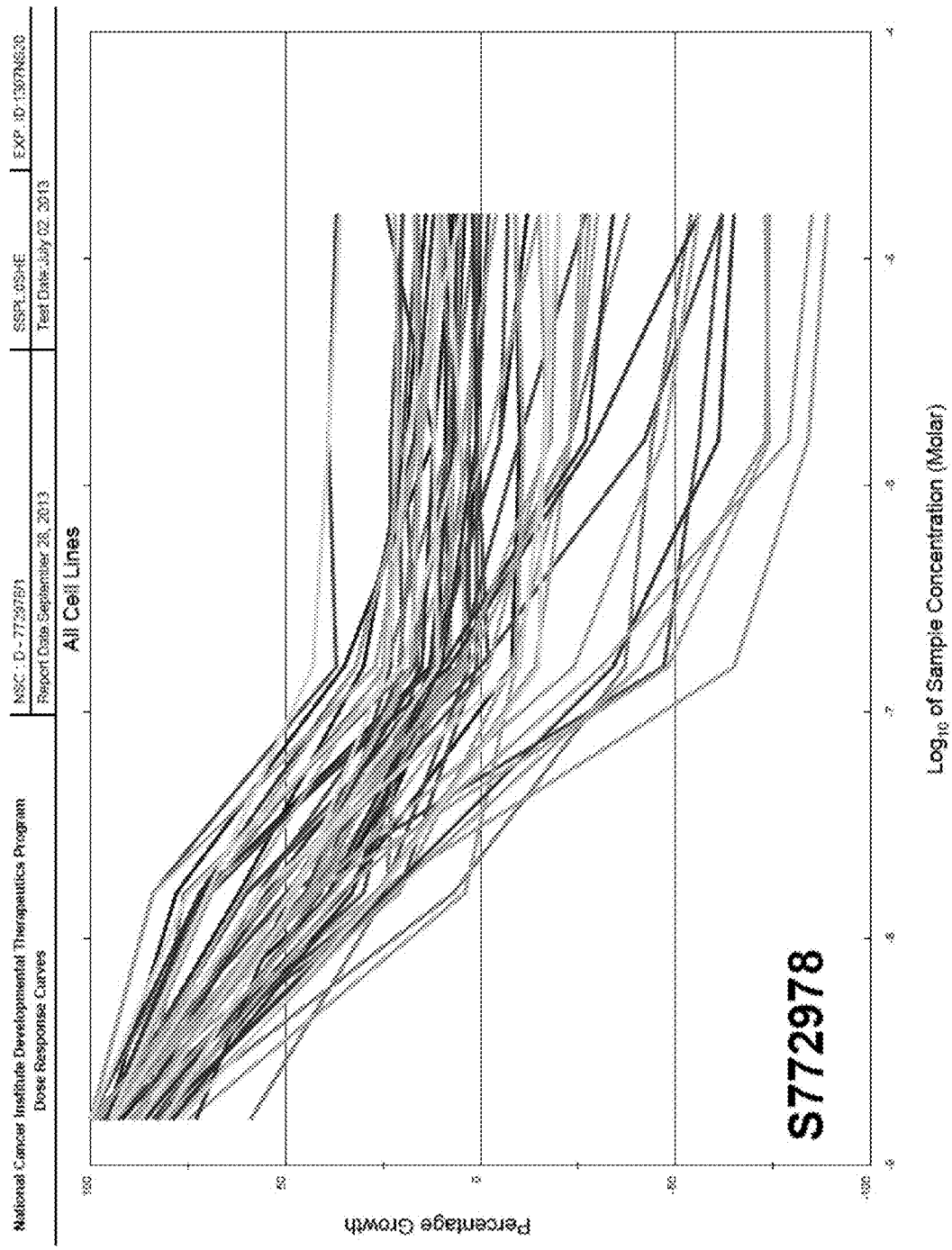
Figure 23B:
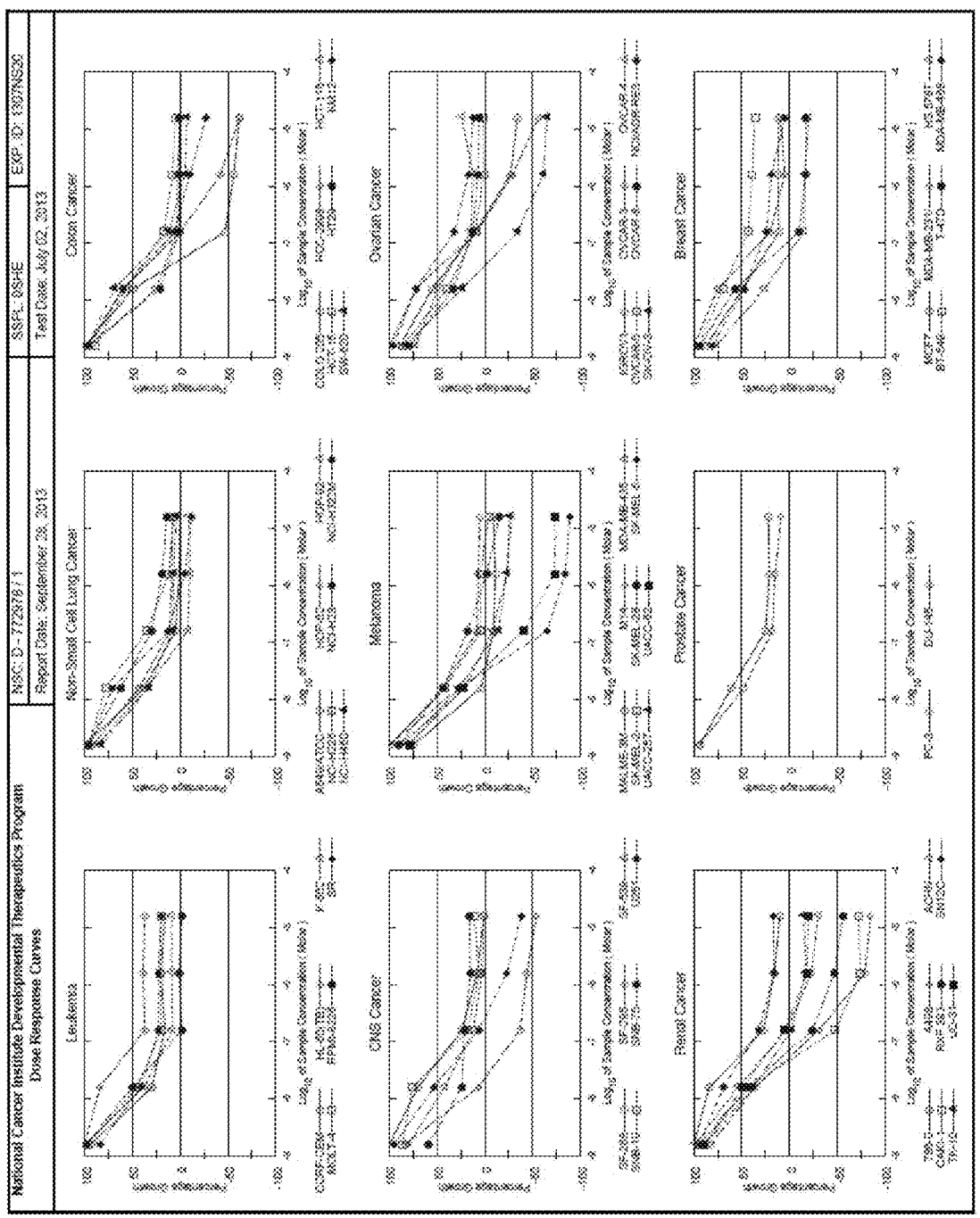
Figure 23D:
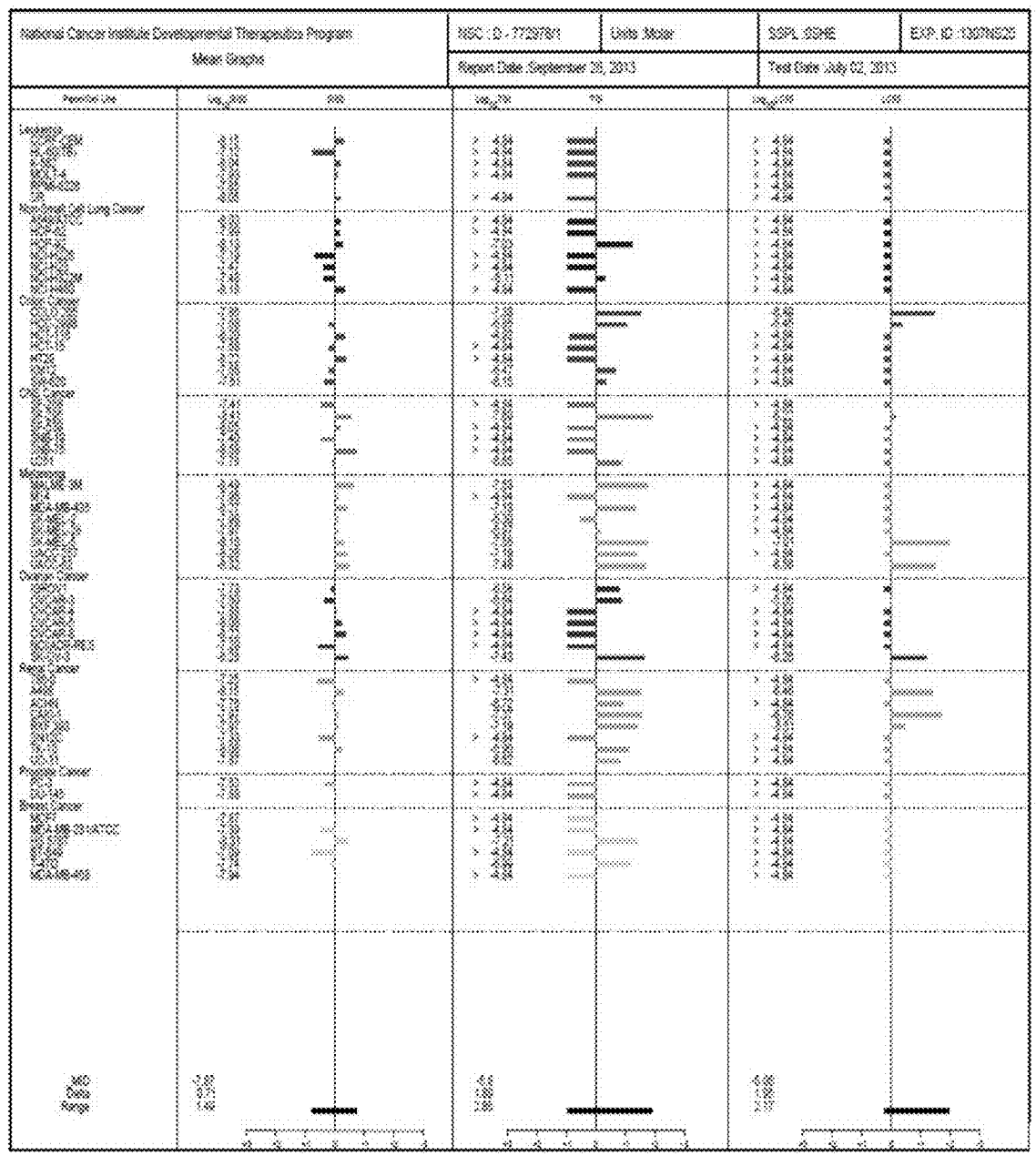
Figure 24A:
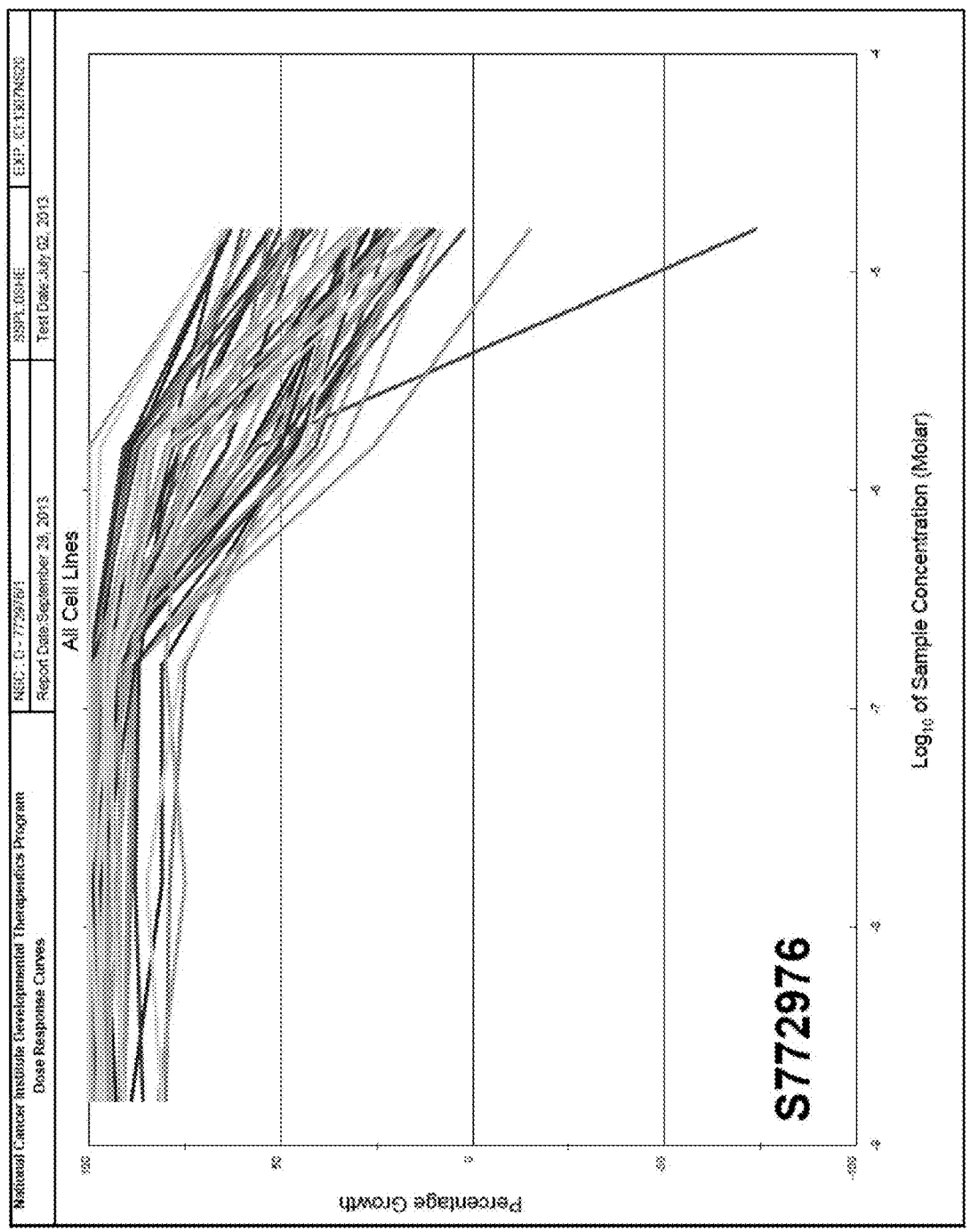
Figure 24B:
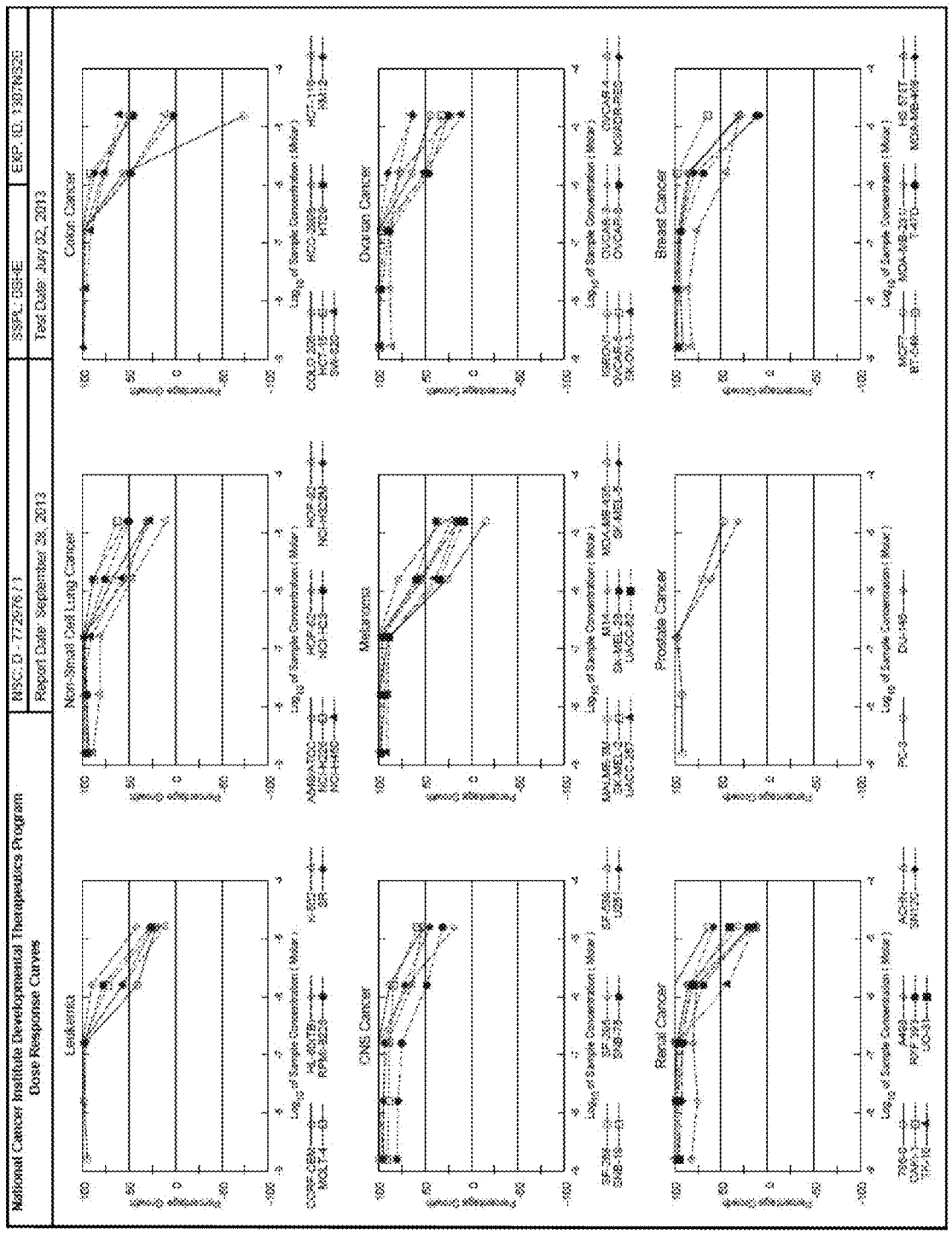
Figure 24D:
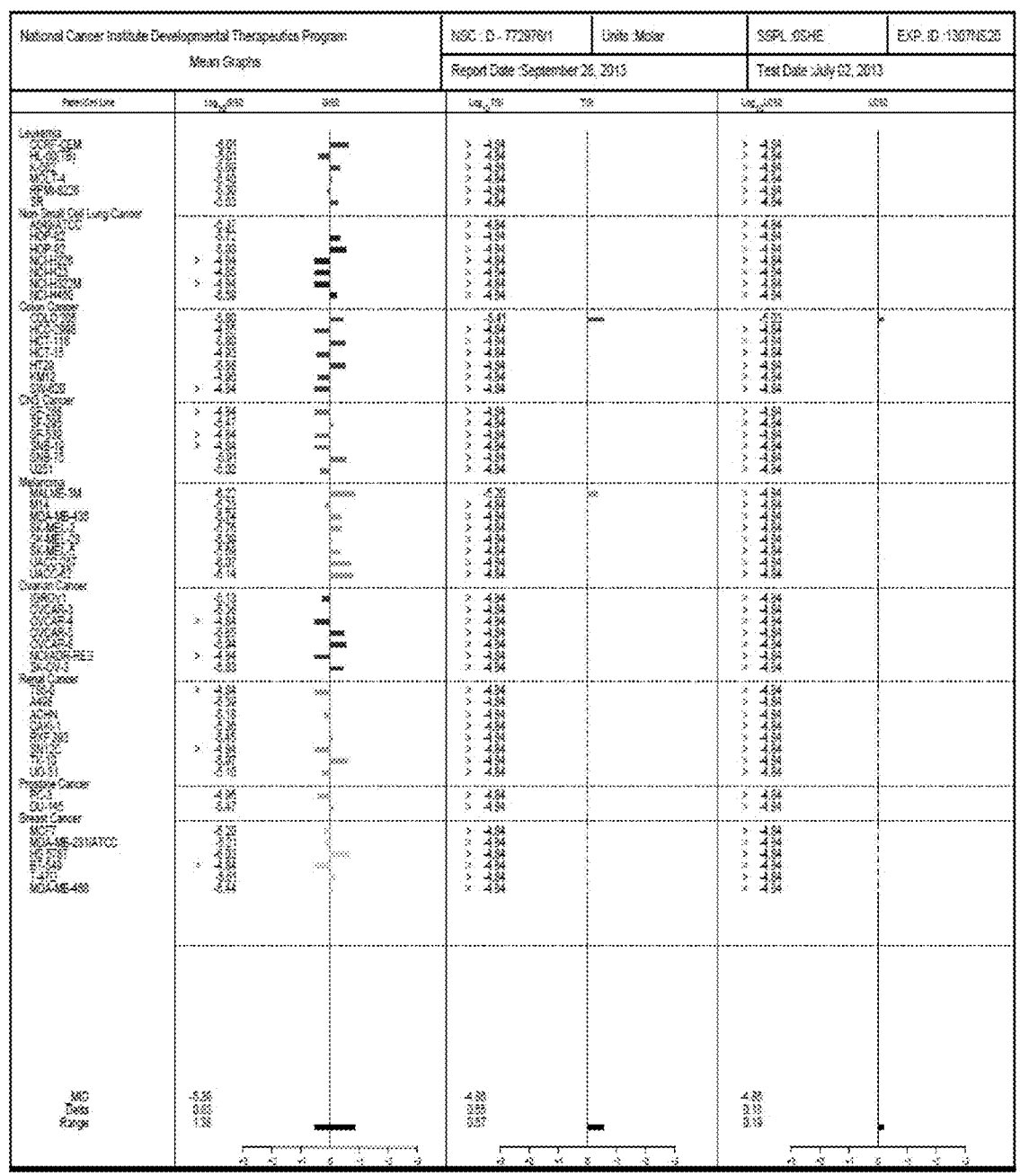
Figure 26:
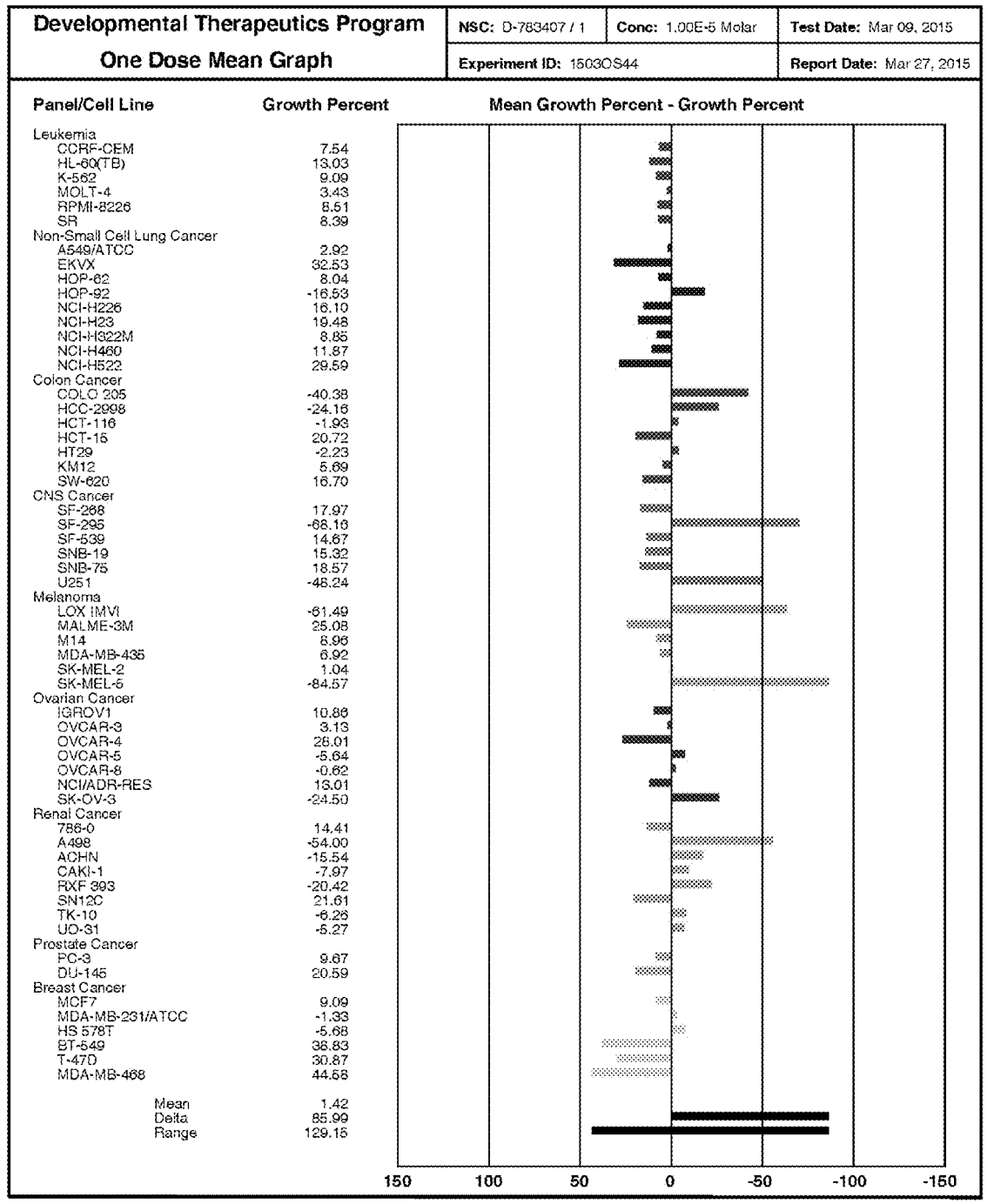
FIG. 26: Results of single dose response evaluation of AA1 in leukemia, non-small cell lung cancer, colon cancer, CNS cancer, melanoma, ovarian cancer, renal cancer, prostate cancer, and breast cancer cell lines.
Figure 27:
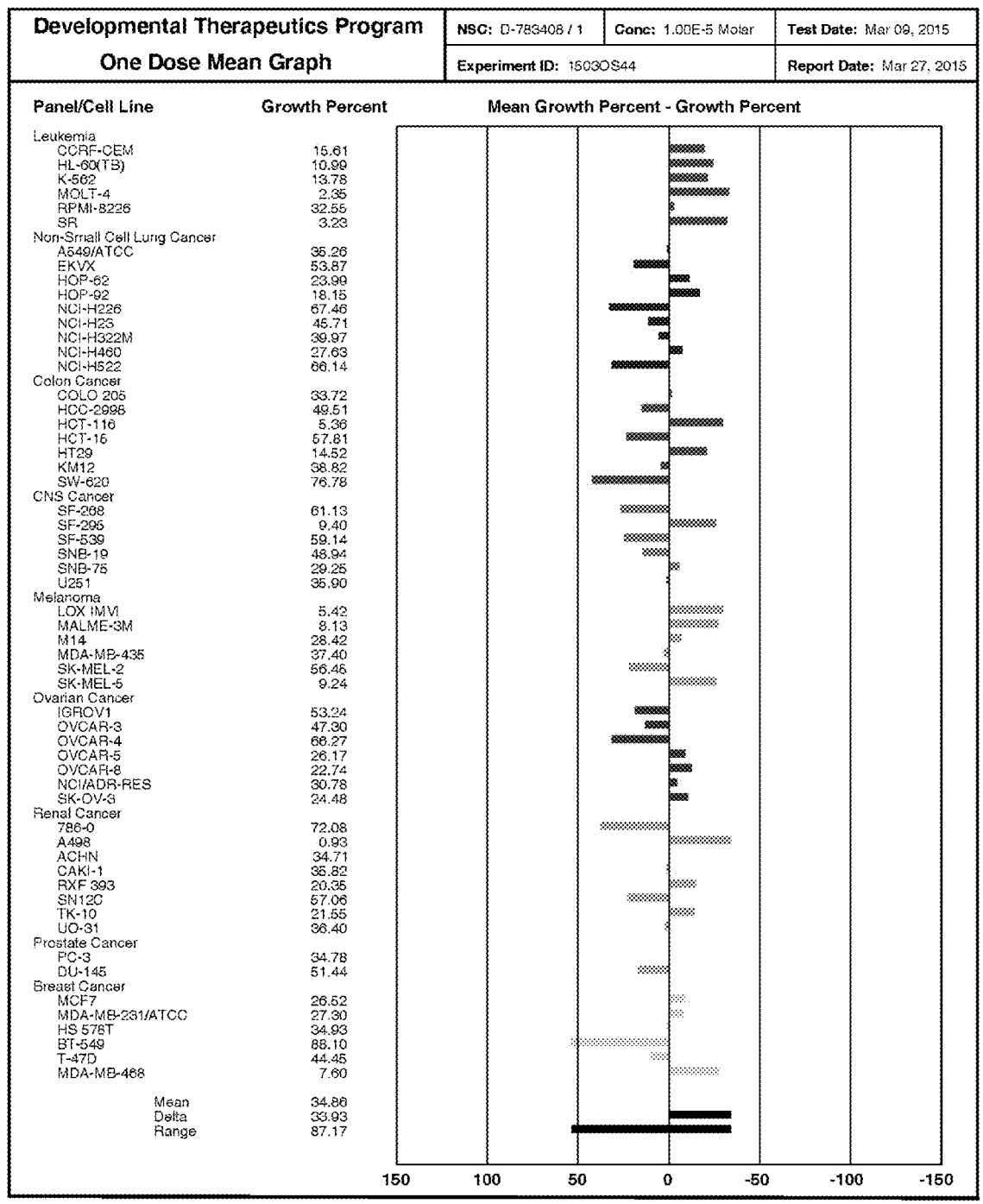
FIG. 27: Results of single dose response evaluation of AA2 in leukemia, non-small cell lung cancer, colon cancer, CNS cancer, melanoma, ovarian cancer, renal cancer, prostate cancer, and breast cancer cell lines.
Figure 28A:
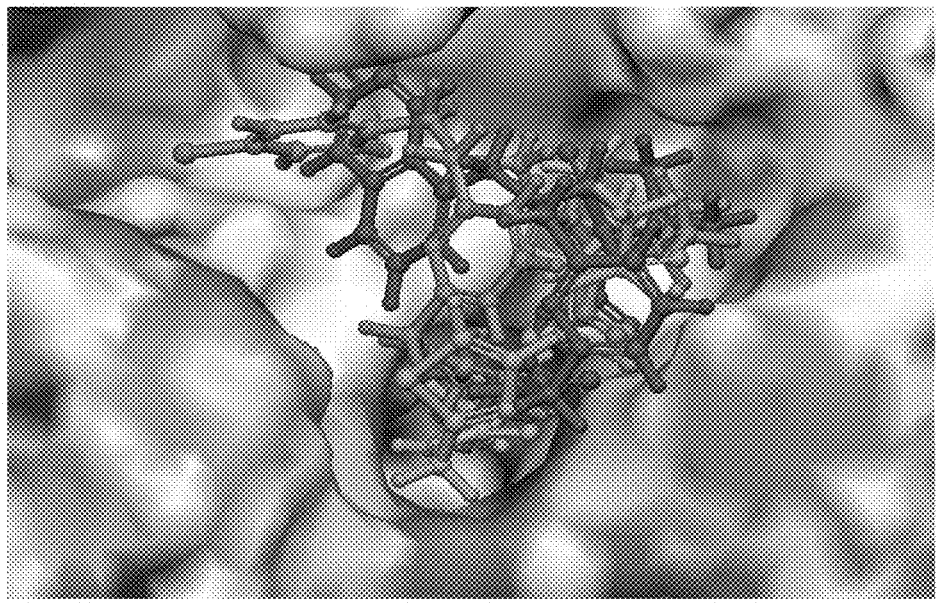
FIGS. 28A-28D: Molecular modeling illustrating the superimposition of largazole (cyan), AA1 (orange), and AA2 (magna) on the surface of HDLP1 (FIG. 28A), HDAC2 (FIG. 28B), HDAC4 (FIG. 28C), and HDAC8 (FIG. 28D).
Figure 28B:
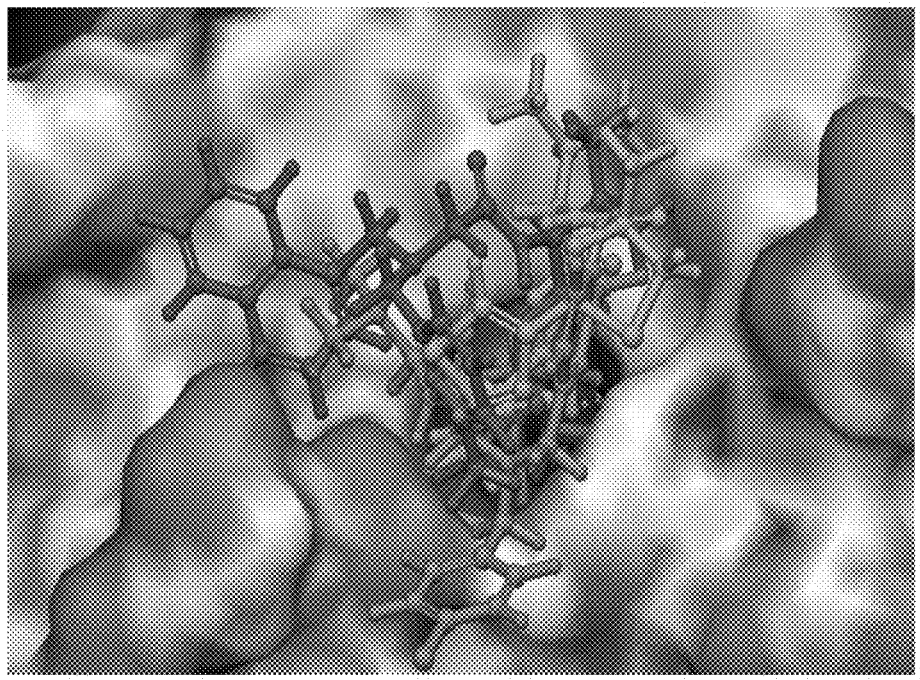
Figure 28C:
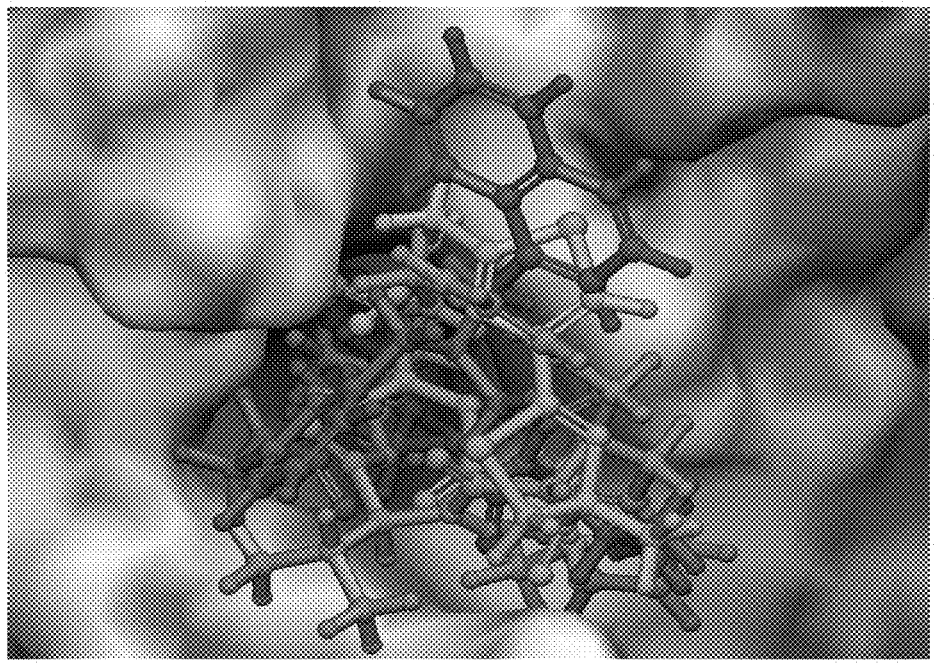
Figure 28D:
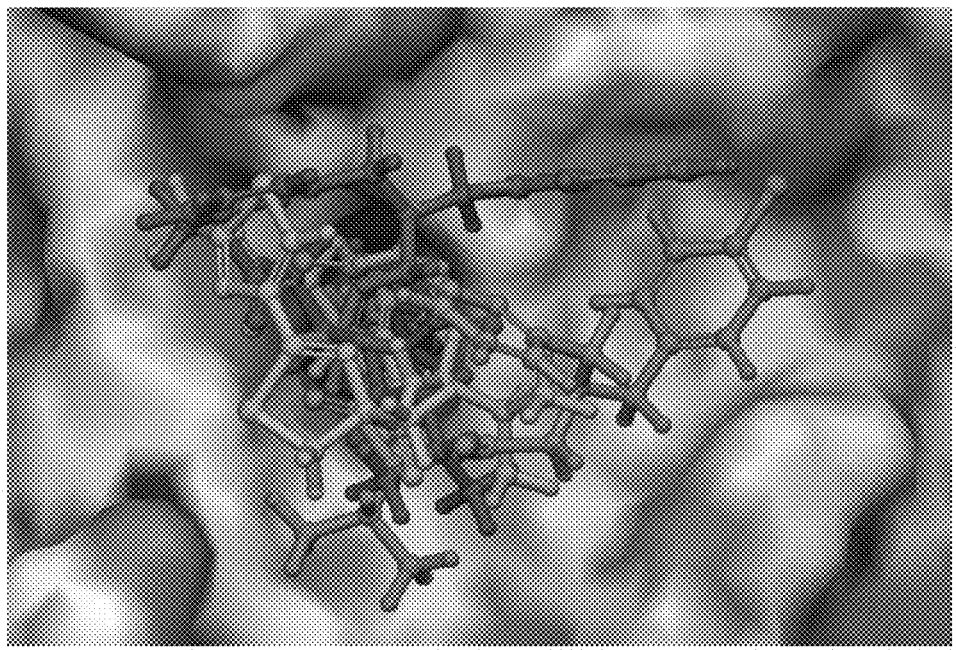

The analogues were tested in the NCI 60 cell line assay using standard assay protocol. The NCI 60 cell line assay includes leukemia, non-small cell lung cancer, colon cancer, CNS cancer, melanoma, ovarian cancer, renal cancer, prostate cancer, and breast cancer cell lines. Results of the cell proliferation inhibition studies at a single dose of 10 μM are shown in FIGS. 16-21, and FIGS. 26-27, and results of the dose response studies for JA1, JA2, and J3 are shown in FIGS. 22-24. FIGS. 26-27 show the results of single dose response evaluations of AA1 and AA2, respectively, in the NCI 60 cell line assay.

Figure 25:
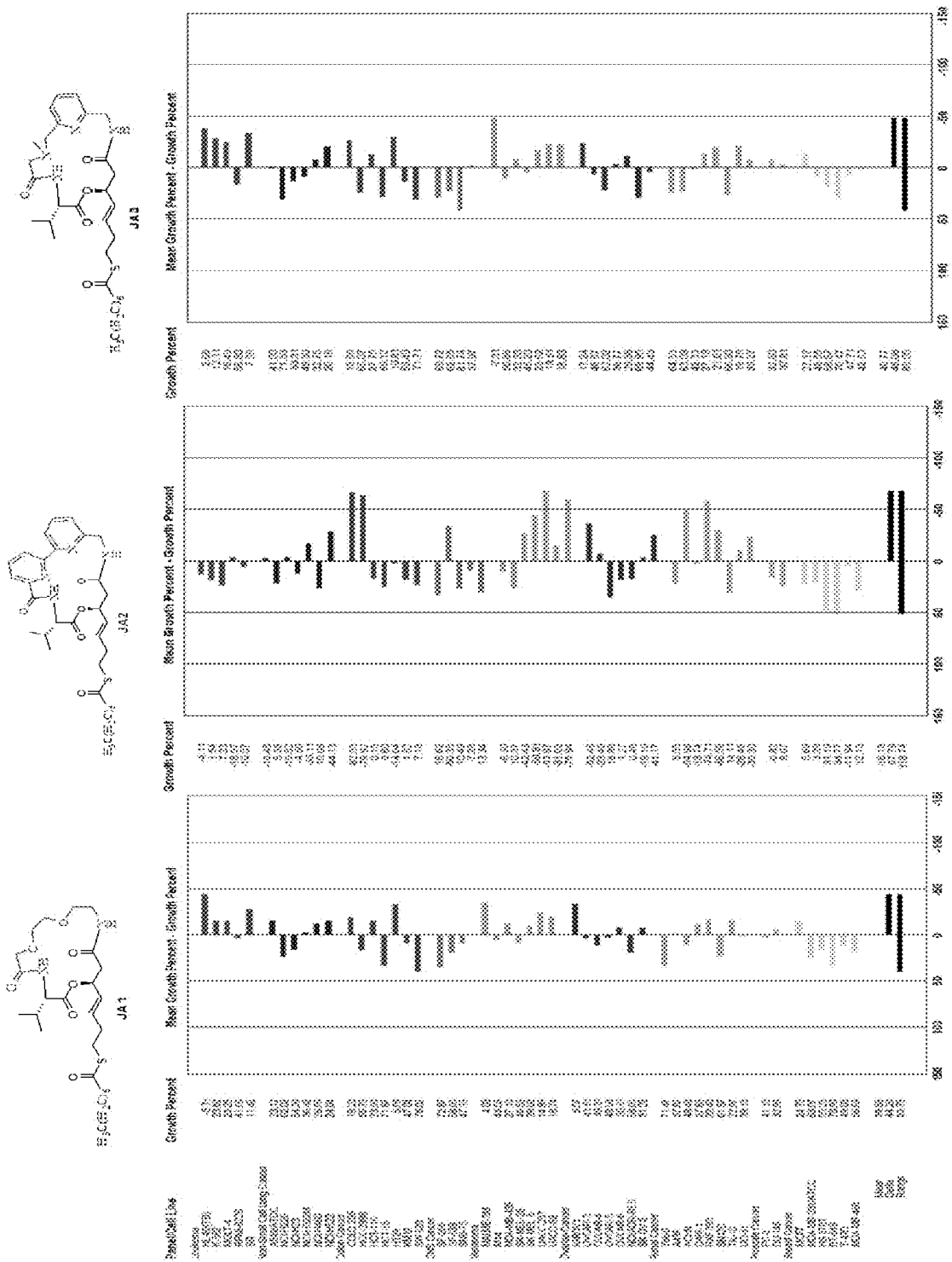
FIG. 25: Side-by-side comparison of the inhibition of cell proliferation by JA1, JA2, and JA3 in the NCI 60 cell line assay.

At 5 μM, both JA1 and JA3 inhibited cell survival nearly as effectively as largazole. FIG. 25 shows a comparison of the cell proliferation inhibition of JA1, JA2, and JA3 in the NCI 60 cell line assay.

Example 3

Molecular Modeling

Molecular modeling was conducted to understand the binding properties of the analogues. FIGS. 28A-28D show the superimposition of largazole, AA1, and AA2 on the surface of HDLP1, HDAC2, HDAC4, and HDAC8.

Figure 29:
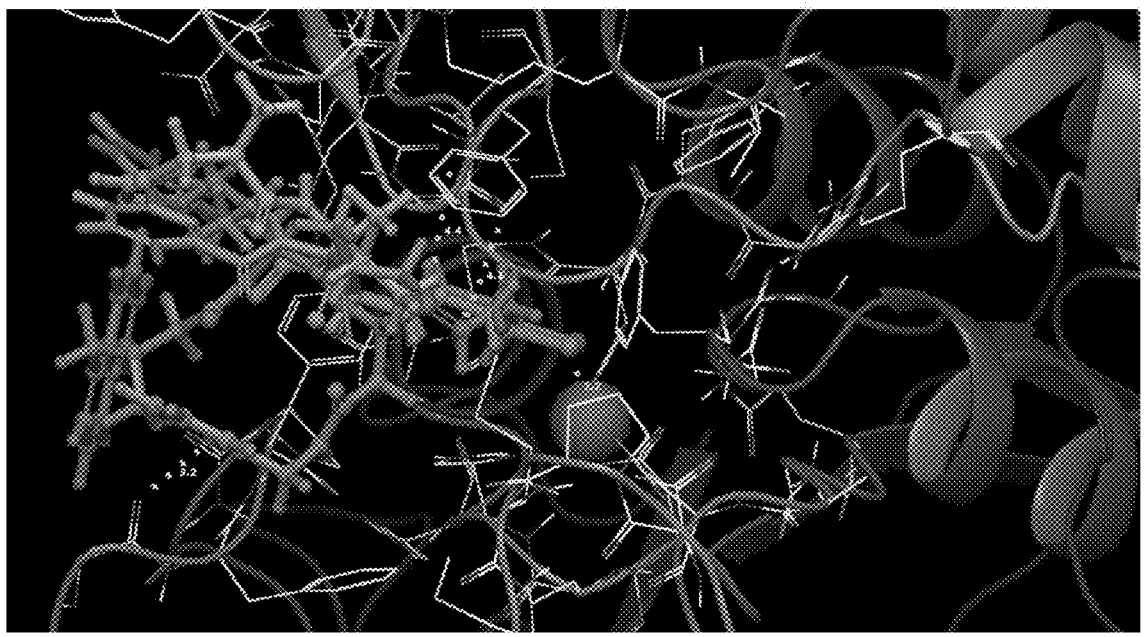
FIG. 29: Molecular modeling illustrating the binding of largazole (magna), JA2 (cyan), and AA2 (orange) to HDAC8.
Figure 30:
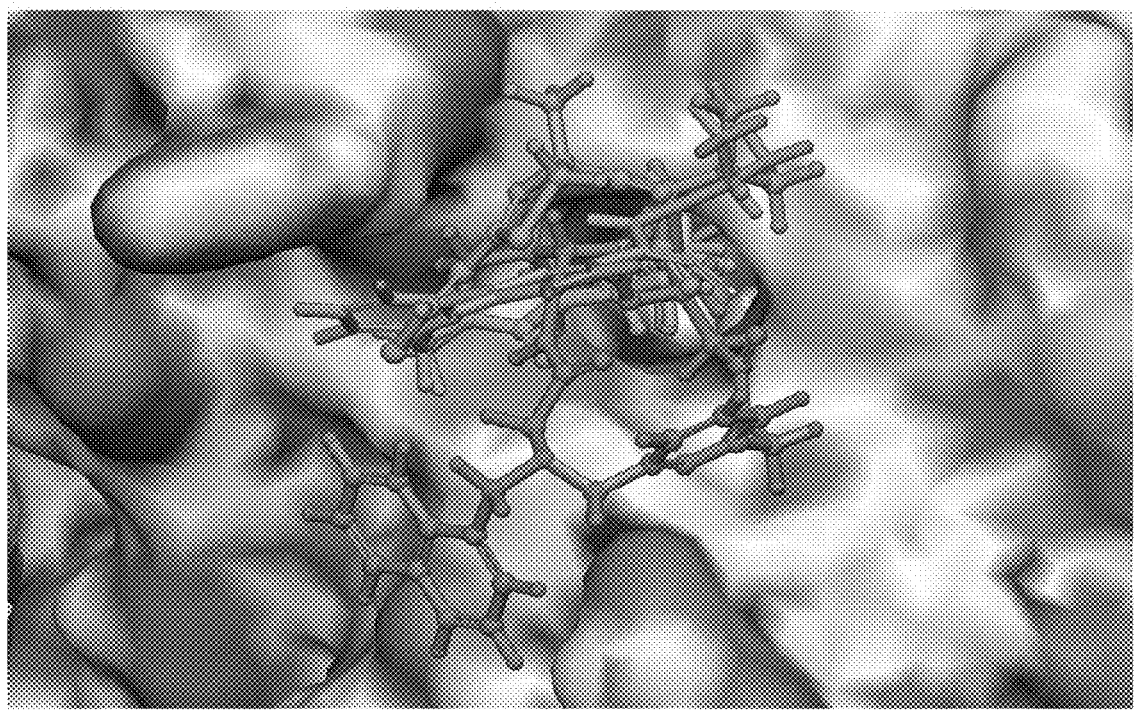
FIG. 30: Molecular modeling illustrating the surface binding of largazole (magna), JA2 (cyan), and AA2 (orange) to HDAC8.
Figure 31A:
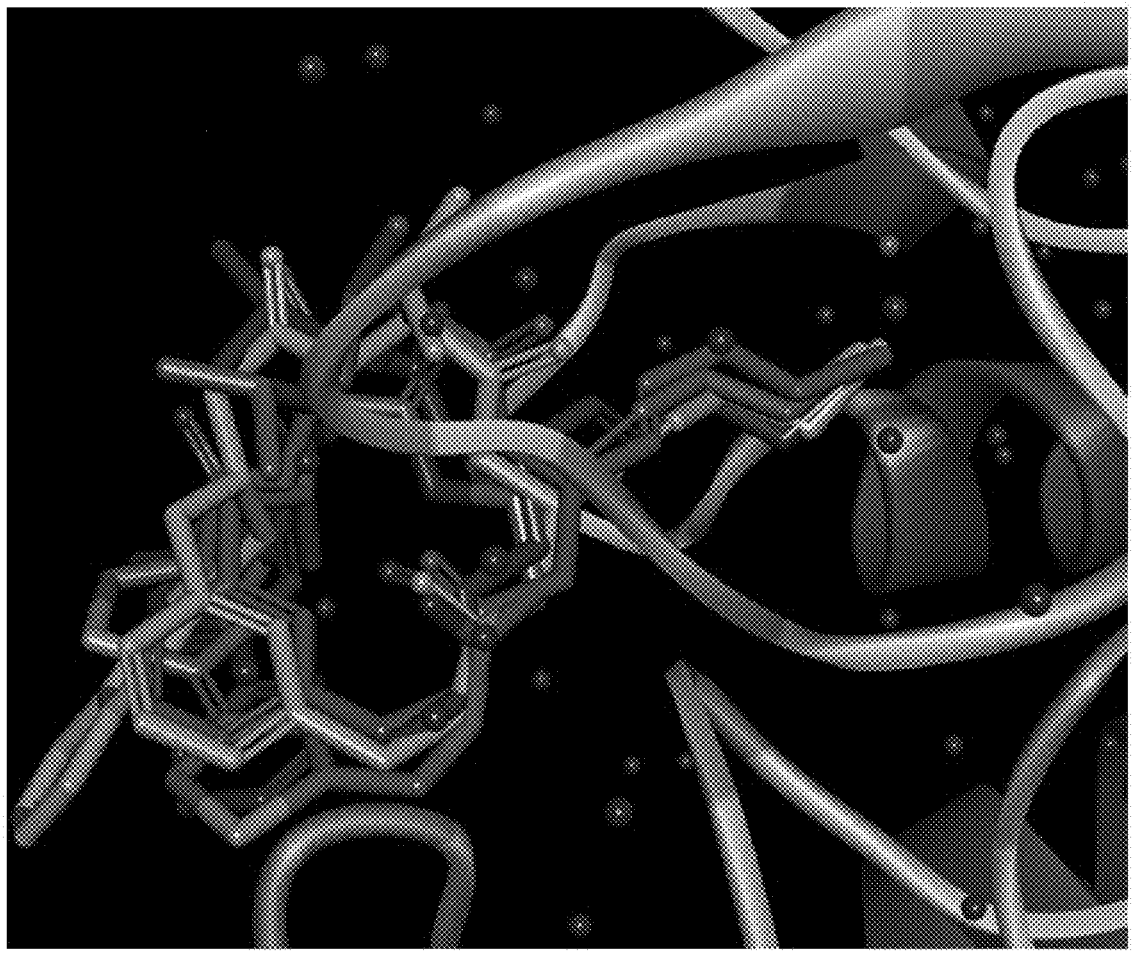
FIGS. 31A-31B: Molecular modeling illustrating a comparison of the largazole crystal structure (FIG. 31A) to the best-docked structures of JA2, AA1, and AA2 (FIG. 31B).
Figure 31B:
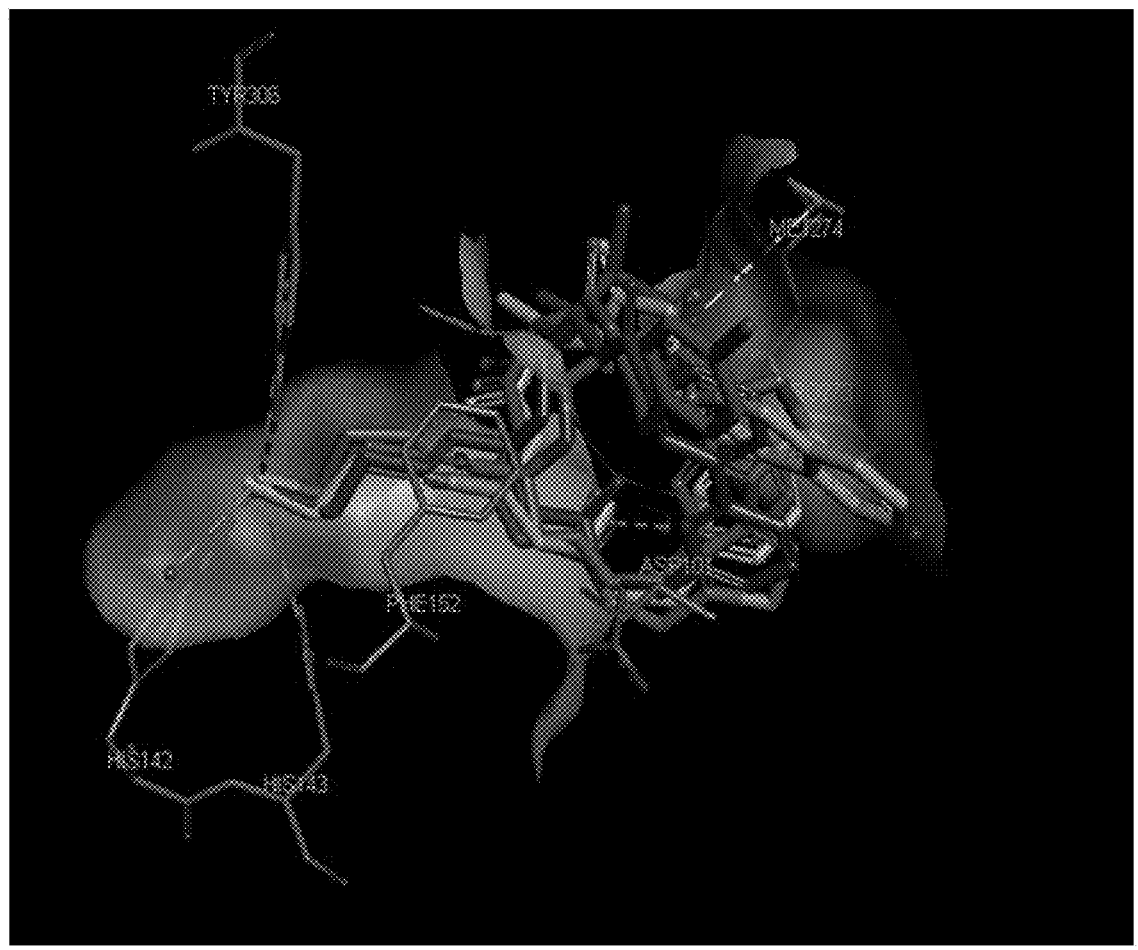

The binding modes of free JA2, AA1, and AA2 into the crystal structure of HDAC8 enzyme was investigated using AutoDock. FIG. 29 illustrates the binding of largazole, JA2, and AA2 to HDAC8, and FIG. 30 illustrates the surface binding of largazole, JA2, and AA2 to HDAC8. A comparative analysis was carried out in order to rationalize the activity and selectivity trends. The RMSD differences between the largazole crystal structure and JA2, AA1, and AA2 are 1.55, 0.95, and 1.86, respectively. FIGS. 31A-31B show a comparison of the largazole crystale structure to best-docked structures of JA2, AA1, and AA2.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound of Formula XV:

Formula XV

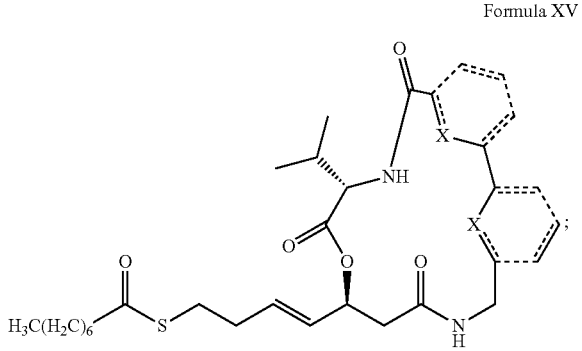

wherein:
dashed lines represent bonds that may be present or absent; and
each X is independently O, N, or $NR_1$, wherein $R_1$ is selected from the group consisting of: methyl, aryl, alkaryl, hydrogen, and ether;
and salts, stereoisomers, racemates, prodrugs, solvates, and hydrates thereof.

2. The compound of claim 1, wherein the compound is of Formula I:

Formula I

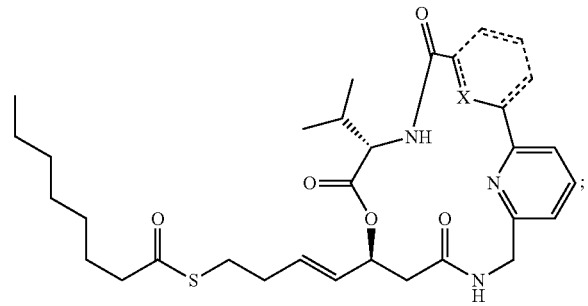

wherein:
dashed lines represent bonds that may be present or absent;
X is either N or $NR_1$; and
$R_1$ is selected from the group consisting of: methyl, aryl, alkaryl, hydrogen, and ether.

3. The compound of claim 2, wherein the compound is of Formula V:

Formula V

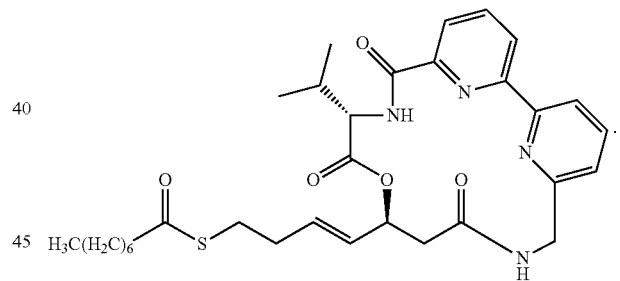

4. The compound of claim 2, wherein the compound is of Formula VII:

Formula VII

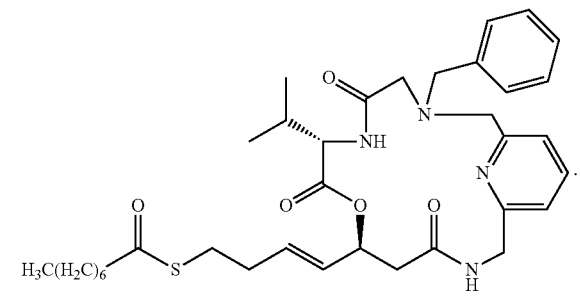

5. The compound of claim 2, wherein the compound is of Formula VIII:

Formula VIII

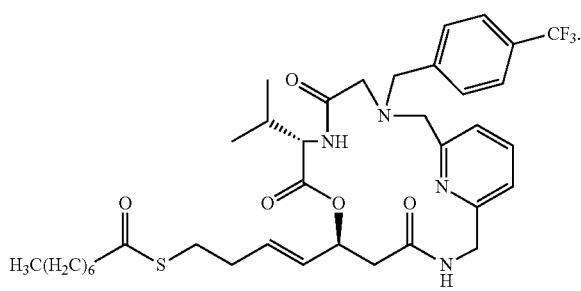

6. The compound of claim 2, wherein the compound is of Formula VIX:

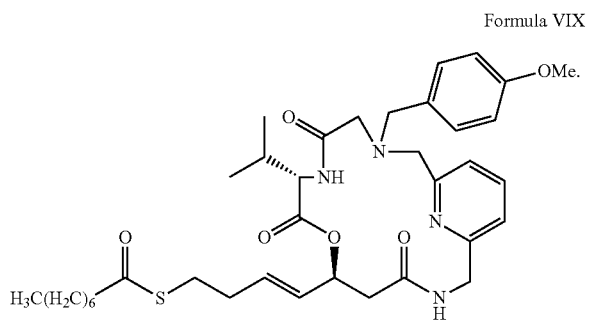

Formula VIX

7. The compound of claim 2, wherein the compound is the of Formula IV:

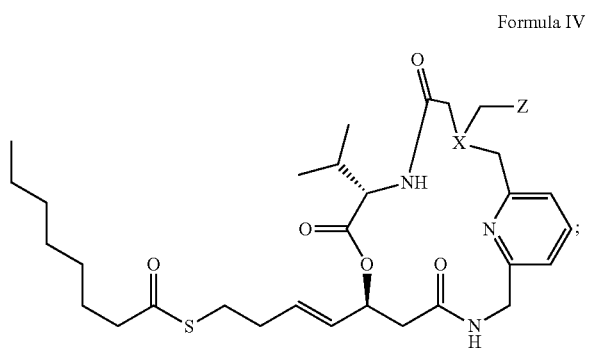

Formula IV wherein Z is selected from the group consisting of H, phenyl, 4-methoxyphenyl, 4-(trifluromethane)phenyl, 4-chlorophenyl, 1-napthyl, and 4-methylphenyl.

8. The compound of claim 2, wherein the compound is of Formula X:

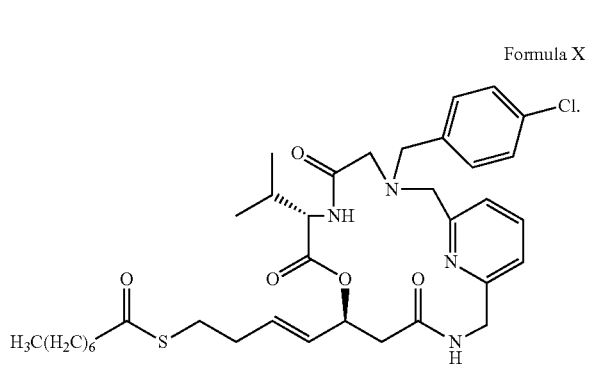

Formula X

9. The compound of claim 2, wherein the compound is of Formula XI:

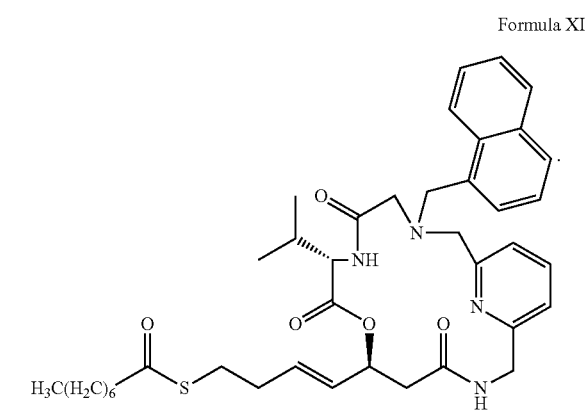

Formula XI

10. The compound of claim 2, wherein the compound is of Formula XII:

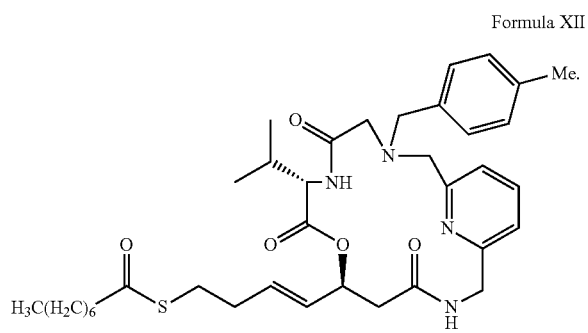

Formula XII

11. The compound of claim 2, wherein the dashed lines are present.

12. The compound of claim 2, wherein $NR_1$ is selected from the group consisting of methylamino-, benzylamino-, and 4-(trifluromethyl)benzylamino-.

13. The compound of claim 3, wherein the dashed lines are absent, and $NR_1$ is selected from the group consisting of benzylamino- and 4-(trifluoromethyl)benzylamino-.

14. A pharmaceutical composition comprising:
   an effective amount of the compound of claim 1; and
   a pharmaceutically acceptable excipient, diluent, or carrier.

15. The pharmaceutical composition of claim 14, wherein the compound is of Formula V:

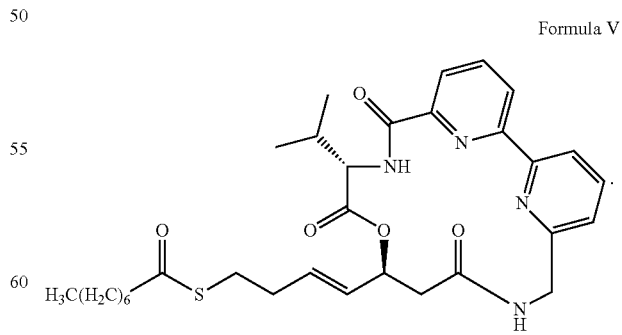

Formula V

16. The pharmaceutical composition of claim 14, wherein the effective amount is from about 5 μM to about 10 μM.

17. A method of inhibiting an HDAC enzymatic activity in cancer cells, the method comprising administering to cancer cells an effective amount of the compound of claim 1, wherein the cancer is selected from the group consisting of leukemia, non-small cell lung cancer, colon cancer, CNS cancer, melanoma, ovarian cancer, renal cancer, prostate cancer, and breast cancer.

18. The method of claim 17, wherein the cancer cells are human cells.

19. The method of claim 17, wherein the compound is of Formula V:

Formula V

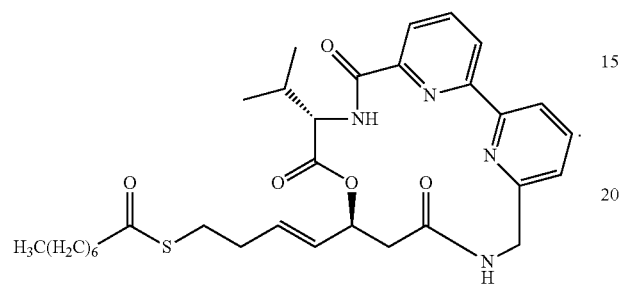

* * * * *